United States Patent
Selnick et al.

(10) Patent No.: US 7,144,899 B2
(45) Date of Patent: Dec. 5, 2006

(54) THROMBIN INHIBITORS

(75) Inventors: Harold G. Selnick, Ambler, PA (US); Mary Beth Young, Lansdale, PA (US); Philippe G. Nantermet, Lansdale, PA (US); James C. Barrow, Harleysville, PA (US); Peter D. Williams, Harleysville, PA (US); Terry A. Lyle, Lederach, PA (US); Donnette D. Staas, Harleysville, PA (US); Kenneth J. Stauffer, Souderton, PA (US); Philip E. Sanderson, Philadelphia, PA (US)

(73) Assignee: Merck & Co., Inc., Rahway, NJ (US)

( * ) Notice: Subject to any disclaimer, the term of this patent is extended or adjusted under 35 U.S.C. 154(b) by 324 days.

(21) Appl. No.: 10/467,439

(22) PCT Filed: Feb. 5, 2002

(86) PCT No.: PCT/US02/04658

§ 371 (c)(1),
(2), (4) Date: Aug. 5, 2003

(87) PCT Pub. No.: WO02/064559

PCT Pub. Date: Aug. 22, 2002

(65) Prior Publication Data

US 2004/0073025 A1   Apr. 15, 2004

Related U.S. Application Data

(60) Provisional application No. 60/267,808, filed on Feb. 9, 2001.

(51) Int. Cl.
*A61K 31/4439* (2006.01)
*C07D 401/12* (2006.01)

(52) U.S. Cl. ............ 514/340; 514/340; 514/361; 546/268.7; 546/269.1; 548/127; 548/131; 548/134

(58) Field of Classification Search ......... 548/127, 548/131, 134; 546/268.7, 269.1; 514/340, 514/361
See application file for complete search history.

(56) References Cited

U.S. PATENT DOCUMENTS

| | | | |
|---|---|---|---|
| 2,277,409 A | 3/1942 | Murray | |
| 4,346,078 A | 8/1982 | Bajusz et al. | |
| 4,703,036 A | 10/1987 | Bajusz et al. | |
| 4,804,743 A | 2/1989 | Kaltenbronn et al. | |
| 5,252,566 A | 10/1993 | Shuman | |
| 5,332,726 A | 7/1994 | Klein et al. | |
| 5,380,713 A | 1/1995 | Balasubramanian et al. | |
| 5,416,093 A | 5/1995 | Shuman | |
| 5,510,369 A | 4/1996 | Lumma et al. | |
| 5,691,356 A | 11/1997 | Das et al. | |
| 5,792,779 A | 8/1998 | Sanderson et al. | |
| 5,798,377 A | 8/1998 | Lumma et al. | |
| 5,866,573 A | 2/1999 | Sanderson et al. | |
| 5,869,487 A | 2/1999 | Coburn et al. | |
| 6,004,976 A | 12/1999 | Coburn | |
| 6,011,038 A | 1/2000 | Dorsey et al. | |
| 6,017,934 A | 1/2000 | Sanderson et al. | |
| 6,051,568 A * | 4/2000 | Gustafsson et al. ..... | 514/210.17 |
| 6,087,373 A | 7/2000 | Coburn et al. | |
| 6,147,078 A | 11/2000 | Sanderson et al. | |
| 6,239,132 B1 | 5/2001 | Coburn et al. | |
| 6,515,011 B1 | 2/2003 | Selnick et al. | |

FOREIGN PATENT DOCUMENTS

| | | |
|---|---|---|
| EP | 0 185 210 | 6/1986 |
| EP | 0185210 A2 * | 6/1986 |
| EP | 0 195 212 A2 | 9/1986 |
| EP | 0 363 284 A2 | 4/1990 |

(Continued)

OTHER PUBLICATIONS

D. B. Henriksen et al., "Peptide Amidation by Enzymatic Transacylation and Photolysis", 1993, vol. 41, pp. 169-180, Int. J. Peptide Protein Res.

(Continued)

*Primary Examiner*—Kamal A. Saeed
*Assistant Examiner*—Janet L. Coppins
(74) *Attorney, Agent, or Firm*—Richard S. Parr; Valerie J. Camara

(57) ABSTRACT

Compounds of the invention are useful in inhibiting thrombin and associated thrombotic occlusions having the following structure Formula (I): wherein u is CH or N; Q is 1)—$N(R^{25})CH(R^{30})$— wherein the nitrogen atom is attached to $R^1$, and $R^{25}$ and $R^{30}$ are independently selected from the group consisting of hydrogen, $C_{3-6}$cycloalkyl, and $C_{1-6}$alkyl, or 2) wherein the nitrogen atom is attached to $R^1$, and m is 0, 1, or 2

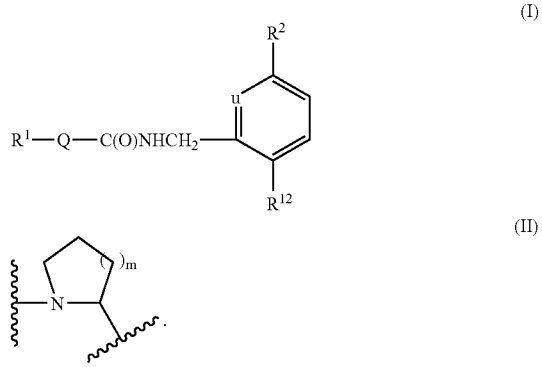

9 Claims, No Drawings

FOREIGN PATENT DOCUMENTS

| | | |
|---|---|---|
| EP | 0 471 651 A2 | 2/1992 |
| EP | 0 479 489 A2 | 4/1992 |
| EP | 0 601 459 A2 | 6/1994 |
| EP | 603112 A1 | 6/1994 |
| EP | 0 648 780 A1 | 4/1995 |
| EP | 0 672 658 A1 | 9/1995 |
| WO | WO 92/07869 | 5/1992 |
| WO | WO 92/14750 | 9/1992 |
| WO | WO 94/29336 | 12/1994 |
| WO | WO 96/31504 | 10/1996 |
| WO | WO 96/32110 | 10/1996 |
| WO | WO 97/15190 | 5/1997 |
| WO | WO 99/29664 | 6/1999 |
| WO | WO 00/35869 | 6/2000 |
| WO | WO 00/75134 A1 | 12/2000 |
| WO | WO 0138323 | 5/2001 |
| WO | WO 02/09711 A1 | 2/2002 |

OTHER PUBLICATIONS

S. Bajusz et al., "Highly Active and Selective Anticoagulants: D-Phe-Pro-ARg-H, a Free Tripeptide Aldehyde Prone to Spontaneous Inactivation, and It's Stable N-Methyl Derivative, D-MePhe-Pro-Arg-H", 1990, vol. 33, pp. 1729-1735, J. Med. Chem.

M. C. Berndt et al., "Platelet Membrane Proteins: Composition and Receptor Function", 1981, pp. 43-75, Gordon (ed) Platelets in Biology and Pathology-2.

B. M. Martin et al., "Platelet Stimulation by Thrombin and Other Proteases", 1975, vol. 14, No. 6, pp. 1308-1314, Biochemistry.

N. J. Greco et al., "PPPACK-Thrombin Inhibits Thrombin-Induced Platelet Aggregation and Cytoplasmic Acidifcation but does not Inhibit Platelet Shape Change", 1990, vol. 75, No. 10, pp. 1983-1990, Blood.

w. Bode et al., "The Refined 1.9 a Crystal Structure of Human alpha Thrombin: Interaction with D-Phe-Pro-Arg Chloromethylketone and Significance of the Tyr-Pro-Pro-Trp Insertion Segment", 1989, vol. 8, No. 11, pp. 3467-3475, The EMBO Journal.

E. F. Workman et al., "Structure-Function Relationships in the Interaction of the alpha-Thrombin with Blood Platelets", 1992, vol. 252, No. 20, pp.-7718-7123, The J. of Biol. Chemistry.

K. Y. Hui et al., "Minimal Sequence Requirement of Thrombin Receptor Agonist Peptide", 1992, vol. 184, No. 2, pp. 790-796, Biolchemical and Biophysical Research Communications.

R. M. Scarborough et al., "Tethered Ligand Agonist Peptides-Structural Requirements for Thrombin Receeptor Activation Reveal Mechanism of Proteolytic Unmasking of Agonist Function", 1992, vol. 267, No. 19, pp. 13146-13149, J. of Biol. Chemistry.

R. R. Vassallo, Jr. et al., "Structure-Function Relationships in the Activation of Platelet Thrombin Receptors by Receptor-Derived Peptides", 1992, vol. 267, No. 9, pp. 6081-6085, J. of Biol. Chemistry.

E. J. Iwanowicz et al., "Alpha-Hydroxy-and Alpha Ketoester Functionalized Thrombin Inhibitors", 1992, vol. 21 No. 12, pp. 1607-1612, Organic and Medicinal Chemistry Letters.

T. Okumura et al., "Platelet Glycocalicin-Interaction with Thrombin and Role as Thrombin Receptor of the Platelet Surface", 1978, vol. 263, No. 10, pp. 3435-3443, J. of Biol. Chemistry.

D. M. Tollefsen et al., "The binding of Thrombin to the Surface of Human Platelets", 1974, vol. 249, No. 8, pp. 2646-2651, J. of Biol. Chemistry.

Vu et al., "Molecular Cloning of a Functional Thrombin Receptor Reveals a Novel Proteolytic Mechanism of Receptor Activation", 1991, vol. 64, pp. 1057-1068, Cell.

R. S. Gronke et al., "Thrombin Interaction with Platelets-Influence of a Platelet Protease Nexin", 1987, vol. 262, No. 7, pp. 3030-3036, J. of Biological Chemistry.

Phillips, "Thrombin Interaction with Human Platelets Potentiation of Thrombin-Induced Aggregation and Release by Inactivated Thrombin", 1974, vol. 32, pp. 207-215, Thrombos, Diathes, Haemorrh (Stuttg).

N. Balasubramanian et al., "Active Site-Directed Synthetic Thrombin Inhibitors: Synthesis, in Vitro and in Vivo Activity Profile of BMY 44621 and Analogs. An Examination of the Role of the Amino Group in the D-Phe-Pro-Arg-H Series", 1993, vol. 36, pp. 300-303, J. Med. Chem.

C. Kettner et al., "The Selective Inhibition of Thrombin by Peptides of Boroarginine", 1990, vol. 265, No. 30, pp. 18289-18297, J. of Biological Chemistry.

R. T. Shuman et al., "Highly Selective Tripeptide Thrombin Inhibitors", 1993, vol. 36, No. 3, pp. 314-319, J. of Medicinal Chem.

M. A. Hussian et al., "Anticoagulant Activity of a Peptide Boronic Acid Thrombin Inhibitor by Various Routes of Administration in Rats", 1991, vol. 12, pp. 1153-1154, Peptides.

C. F. Vencill et al., 1986, vol. 103, Abstract No. 189000 Chemical Abstract.

P. D. Edwards et al., "Design, Synthesis, and Kinetic Evaluation of a Unique Class of Elastase Inhibitors, the Peptidyl alpha-ketobenzoxazoles, and the X-ray Crystal Structure of the Covalent Complex between Porcine Pancreatic Elastase and Ac-Ala-Pro-Val-2-Benzoxazole", 1992, vol. 114, pp. 1854-1863, J. Am. Chem. Soc.

D. Banner et al., "Serine Proteases: 3D Structures, Mechanisms of Action and Inhibitors", 1993, pp. 29-43, Chapter 3, *Persepct. Med. Chem..*

C. Tapparelli et al., "Synthetic Low-Molecular Weight Thrombin Inhibitors: Molecular Design and Pharmacological Profile", 1993, vol. 14, pp. 366-376, TIPS.

* cited by examiner

THROMBIN INHIBITORS

CROSS-REFERENCE TO APPLICATIONS

This application is related to PCT application PCT/US02/04658, filed Feb. 5, 2002, and to provisional application U.S. Ser. No. 60/267,808, filed Feb. 9, 2001.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., J. Amer. Chem. Soc., (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or aketo carboxyl derivatives.

R. J. Brown et al., J. Med. Chem., Vol. 37, pages 1259–1261 (1994) describes orally active, non-peptidic inhibitors of human leukocyte elastase which contain trifluoromethylketone and pyridinone moieties.

H. Mack et al., J. Enzyme Inhibition, Vol. 9, pages 73–86 (1995) describes rigid amidino-phenylalanine thrombin inhibitors which contain a pyridinone moiety as a central core structure.

The present invention concerns proline-based compounds having heterobiaryl substituents.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention are useful as thrombin inhibitors and have therapeutic value in for example, preventing coronary artery disease. The invention includes compounds having the following structure:

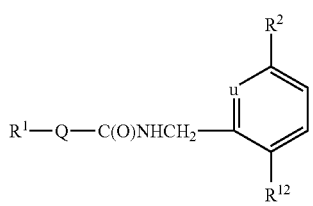

wherein
u is N or CH;
Q is
1) —N($R^{25}$)CH($R^{30}$)—
   wherein
      the nitrogen atom is attached to $R^1$, and
      $R^{25}$ and $R^{30}$ are independently selected from the group consisting of hydrogen, $C_{3-6}$cycloalkyl, and $C_{1-6}$alkyl, or

2)

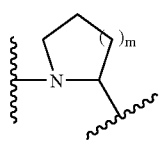

wherein
   the nitrogen atom is attached to $R^1$, and
   m is 0, 1, or 2;
$R^1$ is selected from the group consisting of

1)

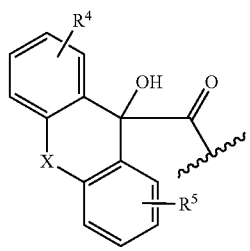

wherein
$R^4$ and $R^5$ are independently selected from the group consisting of hydrogen, halogen, $C^{1-4}$ alkoxy, $C^{1-4}$ alkyl, —OH, and cyano, and
X is a bond, O, $CH_2$, S or NH,

2)

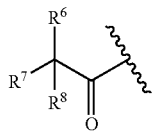

wherein
$R^6$ is selected from the group consisting of
  a) hydrogen,
  b) —OH, and
  c) —$NR^{19}R^{20}$, where $R^{19}$ and $R^{20}$ are independently selected from the group consisting of
    1) hydrogen, and
    2) $C_{1-6}$ alkyl, unsubstituted or substituted with one or more of —OH, —COOH, $C_{3-7}$ cycloalkyl, or $COOR^{17}$, where $R^{17}$ is $C_{1-4}$ alkyl,
    3) $C_{3-7}$ cycloalkyl,
    4) $C(O)OR^{18}$,
    5) $C(O)R^{18}$,
    6) $C(O)NHR^{18}$,
    7) $SO_2R^{18}$,
    8) $C(O)NH_2$, and
    9) CN,
      wherein $R^{18}$ is selected from the group consisting of $C_{1-4}$ alkyl, aryl, and $C_{3-7}$ cycloalkyl, and
$R^7$ and $R^8$ are independently selected from the group consisting of
  a) hydrogen,
  b) —$CF_3$,
  c) unsubstituted $C_{1-6}$ alkyl,
  d) a ring slected from the group consisting of

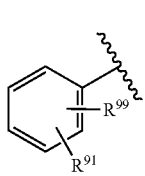 and 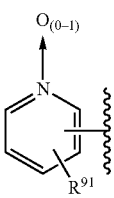

wherein $R^{91}$ and $R^{99}$ are independently selected from the group consisting of
    1) hydrogen,
    2) halogen,
    3) $C_{1-4}$ alkoxy,
    4) $C_{1-4}$ alkyl,
    5) hydroxy,
    6) $CF_3$, and
    7) cyano,
  e) $C_{3-6}$ cycloalkyl,
  f) $C_{1-6}$ alkyl substituted with one of the group consisting of
    1) $C_{3-6}$ cycloalkyl,
    2) —COOH,
    3) —OH,

4)

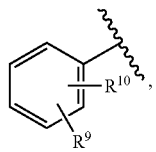

5)

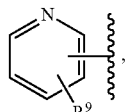

6)

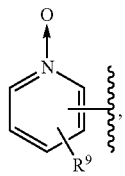

wherein $R^9$ and $R^{10}$ are independently selected from the group consisting of
  aa) hydrogen,
  bb) halogen,
  cc) $C_{1-4}$ alkoxy,
  dd) $C_{1-4}$ alkyl,
  ee) hydroxy,
  ff) $CF_3$ and
  gg) cyano, and

3)

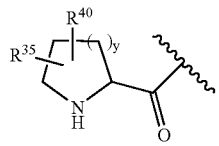

wherein
y is 0, 1 or 2, and
$R^{35}$ and $R^{40}$ are independently selected from the group consisting of hydrogen and $C_{1-6}$ alkyl;
$R^2$ is selected from the group consisting of
  1) hydrogen,
  2) halogen,
  3) $C_{1-4}$ alkyl,
  4) $C_{3-7}$ cycloalkyl,
  5) $CF_3$,
  6) $OCF_3$,
  7) $C_{1-4}$ alkoxy, and
  8) cyano; and
$R^{12}$ is
  1) a 5-membered heteroaryl ring having 2, 3, or 4 heteroatoms, provided that at least 2 heteroatoms are N, and at most 1 of the heteroatoms is S or O, said ring being unsubstituted or substituted, at any one ring atom, with $C_{1-6}$ alkyl or halogen, or
  2) a 6-membered heteroaryl ring with 1–2 nitrogen atoms, said ring being unsubstituted or substituted with with $C_{1-6}$ alkyl or halogen.

In a class of compounds of the invention, Q is selected from the group consisting of

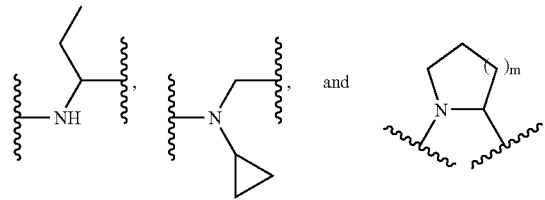

where the nitrogen atom is attached to $R^1$;
X is a bond;
$R^2$ is hydrogen, Cl or F;
y is 1 or 2.

In a subclass of the class of compounds, $R^{12}$ is independently selected from the group consisting of

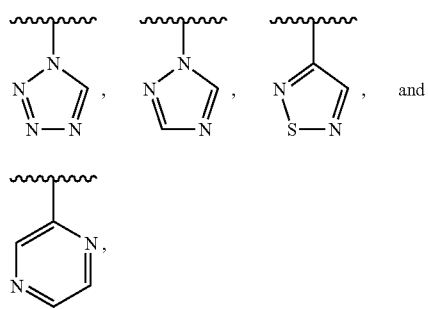

In a group of this subclass of compounds, $R^1$ is selected from the group consisting of

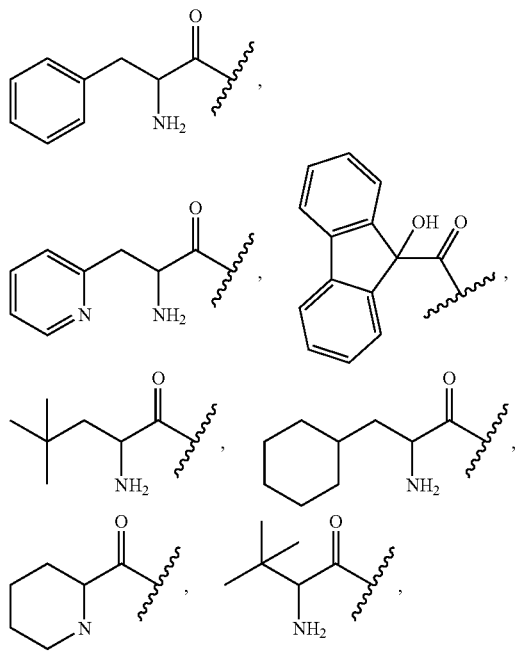

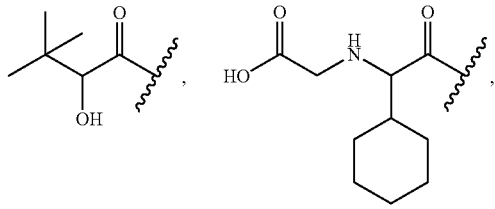

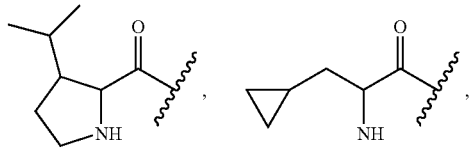

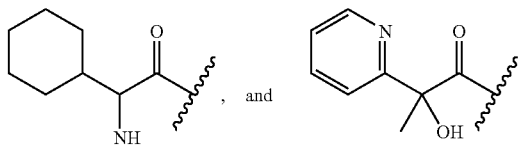

Examples of compounds of the invention include the following:

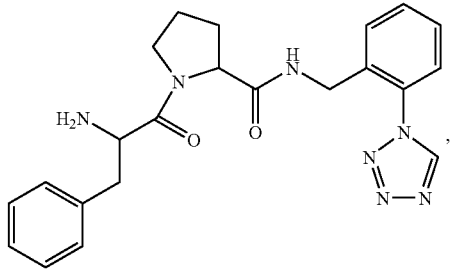

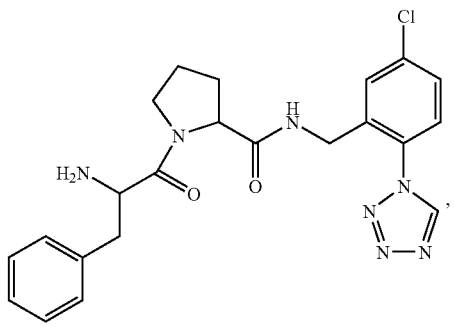

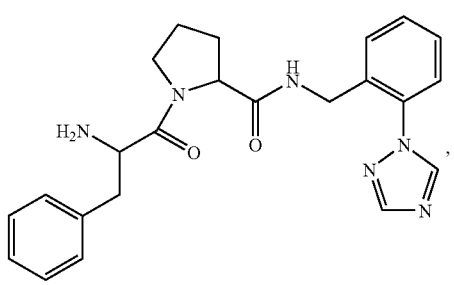

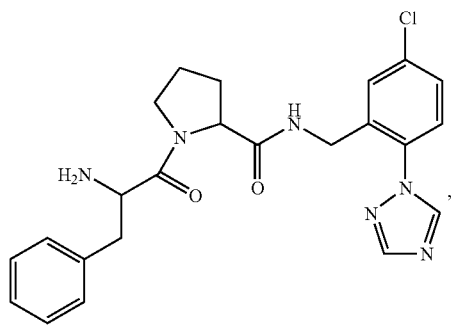,
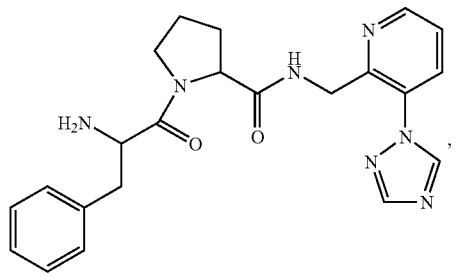,
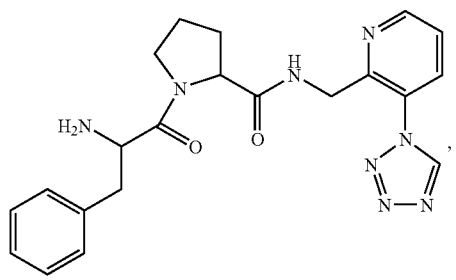,
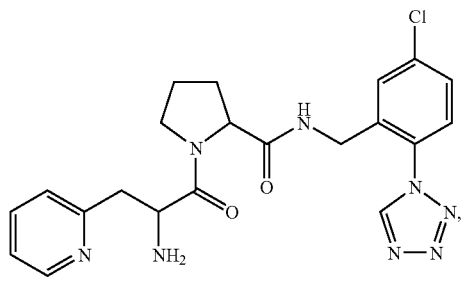,
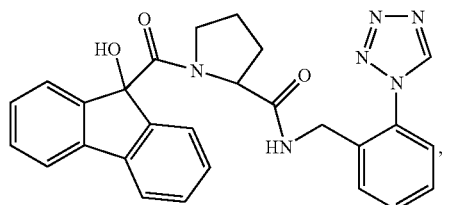,
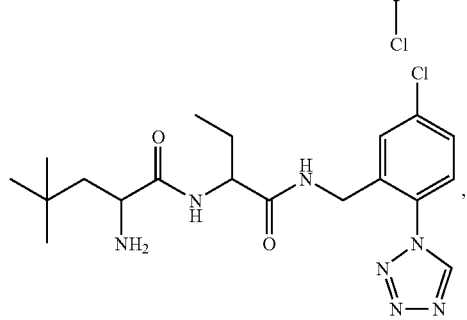,
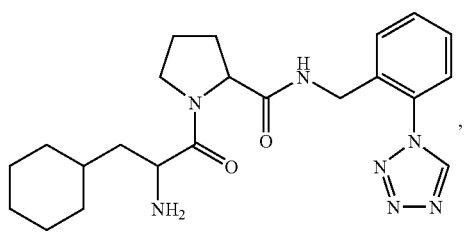,
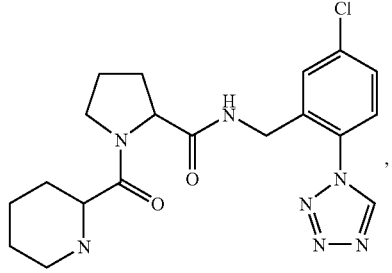,
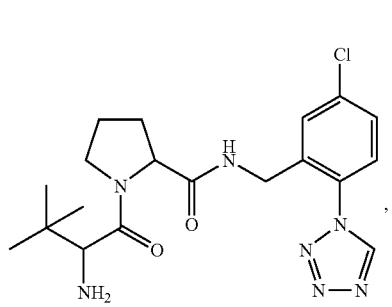,
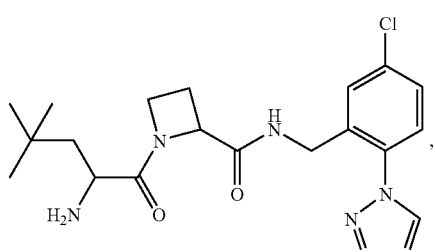,
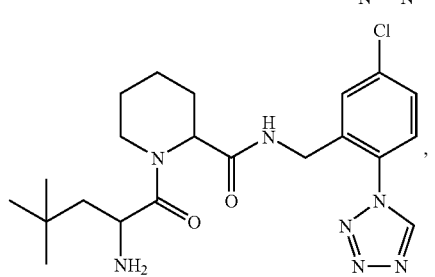,
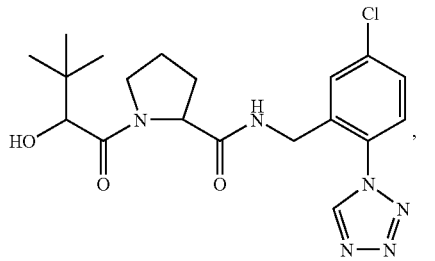, -continued

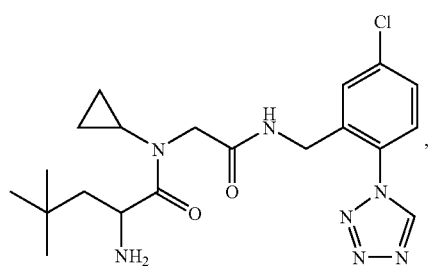

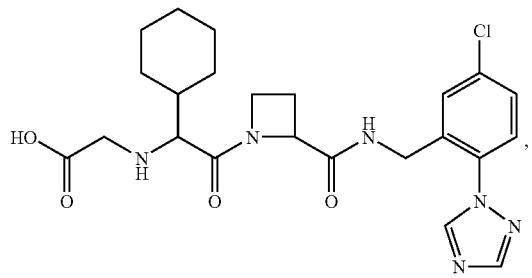

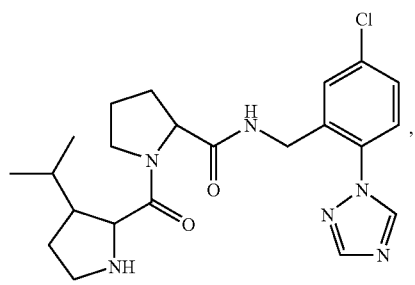

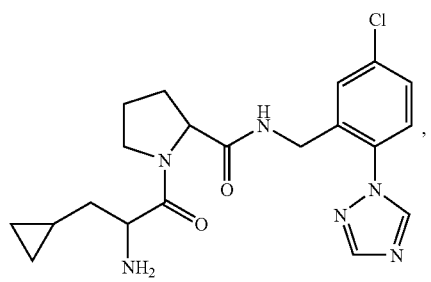

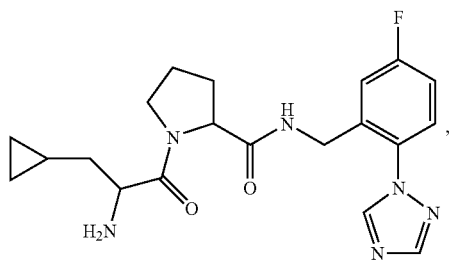

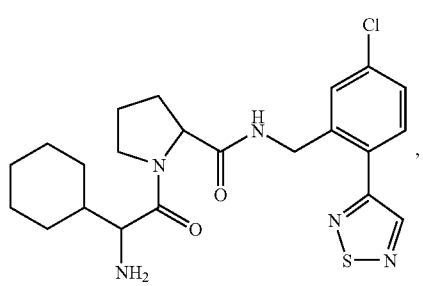

-continued

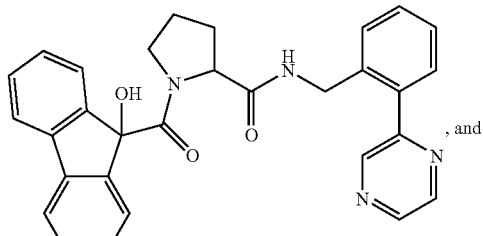

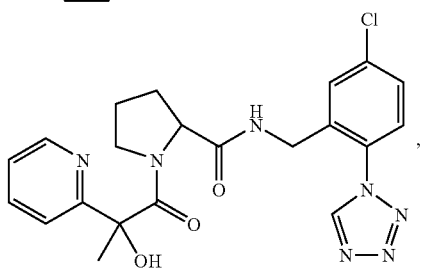

and pharmaceutically acceptable salts thereof.

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

Some abbreviations that may appear in this application are as follows:

| ABBREVIATIONS | |
|---|---|
| Designation | |
| BuLi | butyl lithium |
| CH$_2$Cl$_2$ | dichloromethane |
| DIEA | diisopropylethylamine |
| DMF | dimethylformamide |
| EDC | 1-ethyl-3-(3-dimethylaminopropyl)carbodiimide hydrochloride |
| EtOAc | ethyl acetate |
| EtOH | ethanol |
| HCl | hydrochloric acid |
| HATU | hexafluorophosphate |
| HOAT | 1-hydroxy-7-azabenzotriazole |
| LiCl | lithium chloride |
| LiOH | lithium hydroxide |
| MeOH | methanol |
| MgSO$_4$ | magnesium sulfate |
| NH$_4$OH | ammonium hydroxide |
| NaHCO$_3$ | sodium hydrogen carbonate |
| Na$_2$SO$_4$ | sodium sulfate |
| Pd-C | palladium on activated carbon catalyst |
| THF | tetrahydrofuran |

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "halogen", as used herein, means fluoro, chloro, bromo and iodo; and "counterion" is used to represent a small, single negatively-charged species, such as chloride, bromide, hydroxide, acetate, trifluoroacctate, perchlorate, nitrate, benzoate, maleate, sulfate, tartrate, hemitartrate, benzene sulfonate, and the like.

The term "cycloC$_{3-7}$alkyl" is intended to include cyclopropyl, cyclobutyl, cyclopentyl, cyclohexyl and cycloheptyl, and the like.

The term "aryl" as used herein except where noted, represents a stable 6- to 10-membered mono- or bicyclic ring system such as phenyl, or naphthyl. The aryl ring can be unsubstituted or substituted with one or more of C$_{1-4}$ lower alkyl; hydroxy; alkoxy; halogen; amino.

The pyridyl N-oxide portion of the compounds of the invention are structurally depicted using conventional representations

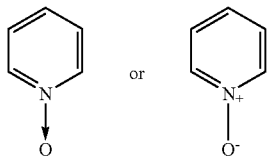

which have equivalent meanings.

In this specification methyl substituents may be represented by

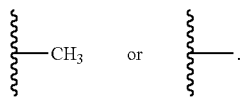

For example, the structures

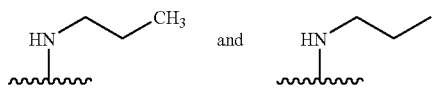

have equivalent meanings.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The invention also includes a method for treating an inflammatory disease in a patient which comprises treating the patient with a composition comprising a compound of the present invention. Such diseases include but are not limited to nephritis, systemic lupus erythematosus, rheumatoid arthritis, glomerulonephritis, and sacoidosis.

The invention is also a method for treating an inflammatory disease in a patient that comprises treating the patient with a combination comprising a compound of the invention and an NSAID, e.g., a COX-2 inhibitor. Such diseases include but are not limited to nephritis, systemic lupus, erythematosus, rheumatoid arthritis, glomerulonephritis, vasculitis and sacoidosis.

The present invention is a method for relieving pain, fever and inflammation of a variety of conditions including nephritis, systemic lupus erythematosus, rheumatoid arthritis, glomerulonephritis, sacoidosis, rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures in a patient by administering to the patient a therapeutically effective amount of a compound of the invention. Thrombin inhibitors may also be useful for the treatment of dementia including pre-senile and senile dementia, and in particular, dementia associated with Alzheimer Disease.

In inflammatory diseases wherein fibrin formation is prominent, the fibrin may be a determinant of the pathology. Fibrin serves as a matrix onto which inflammatory cells can migrate and adhere. (see Sherman et al., 1977 *J. Exp. Med.* 145:76–85; Altieri et al., 1986 *J. Clin. Invest.* 78:968–976; Wright et al., 1983 *Proc. Natl. Acad. Sci.* 85:7734–7738; Altieri et al., 1993 *J. Biol. Chem.* 268;1847–1853). Fibrin also enhances expression of the inflammatory cytokine IL-1beta and decreases expression of IL-1 receptor antagonist by human peripheral blood mononuclear cells (see Perez 1995 *J. Immunol.* 154:1879–1887). The anticoagulants warfarin and heparin attenuate delayed-type hypersensitivity reactions and experimental nephritis in animals. (see Jasain et al., Immunopathogenesis of Rheumatoid Arthritis Eds. G. S. Panayi et al., Surrey, UK, Reedbooks, Ltd. and Halpern et al., 1965 *Nature* 205:257–259). Enzymatic defibrination with ancrod diminishes the degree of experimental nephritis (Naish et al., 1972 *Clin. Sci.* 42:643–646), systemic lupus erythematosus (Cole et al., 1990 *Kidney Int.* 37:29–35, and rheumatoid arthritis (see Busso et al., 1998 *J. Clin. Invest.* 102:41–50) in animals, and glomerulonephritis in man (see Kim et al., 1988 *Q. J. Med.* 69:879–905). Additionally, intra articular injection of fibrin induces arthritis in rabbits immunized with fibrin Dumonde et al., 1961 *British Journal of Experimental Pathology* XLIII:373–383), and antigen-induced arthritis in mice is exacerbated in urokinase-deficient mice wherein fibrinolysis synovial fibrin is compromised (see Busso et al., 1998 *J. Clin. Invest.* 102:41–50).

In diseases where fibrin deposition is prominent such as, but not limited to, rheumatoid arthritis, systemic lupus erythematosus, glomerulonephritis, vasculitis and sacoidosis, lowering the steady state concentration of fibrin by administration of a compound of the invention will, according to the instant invention, diminish the pathological inflammatory responses associated with these diseases.

Similarly, compounds of the invention will be useful as a partial or complete substitute for conventional NSAIDs in preparations wherein they are presently co-administered with other agents or ingredients. Thus in further aspects, the invention encompasses pharmaceutical compositions for treating inflammatory diseases as defined above comprising a non-toxic therapeutically effective amount of a compound of the invention as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a diuretic; a sedating or non-sedating antihistamine. In addition the invention encompasses a method of treating inflammatory diseases comprising administration to a patient in need of such treatment a non-toxic therapeutically effect amount of a compound of the invention, optionally co-administered with one or more of such ingredients as listed immediately above.

The instant invention also involves a novel combination therapy comprising the administration of a therapeutically effective amount of an NSAID such as a COX-2 inhibitor in combination with a therapeutically effective amount of a compound of the invention to a mammal, and more particularly, to a human. The combination therapy is used to treat inflammatory diseases.

The instant pharmaceutical combinations comprising a compound of the invention in combination with an NSAID such as a COX-2 inhibitor include administration of a single pharmaceutical dosage formulation which contains both a compound of the invention and the NSAID, as well as administration of each active agent in its own separate pharmaceutical dosage formulation. Where separate dosage formulations are used, the compund of the invention and the NSAID can be administered at essentially the same time, i.e., concurrently, or at separately staggered times, i.e, sequentially. The "instant pharmaceutical combination" is understood to include all these regimens. Administration in these various ways are suitable for the present invention as long as the beneficial pharmaceutical effect of the compound of the invention and the NSAID are realized by the patient at substantially the same time. Such beneficial effect is preferably achieved when the target blood level concentrations of each active drug are maintained at substantially the same time. It is preferred that the compound of the invention and the NSAID be co-administered concurrently on a once-a-day dosing schedule; however, varying dosing schedules, such as the compound of the invention once per day and the NSAID once, twice or more times per day, or the NSAID once per day and the compound of the invention once, twice or more times per day, is also encompassed herein. A single oral dosage formulation comprised of both the compound of the invention and the NSAID is preferred. A single dosage formulation will provide convenience for the patient.

The instant invention also provides pharmaceutical compositions comprised of a therapeutically effective amount of an NSAID, or a pharmaceutically acceptable salt thereof, in combination with a therapeutically effective amount of a compound of the invention, or a pharmaceutically acceptable salt thereof, and a pharmaceutically acceptable carrier. One embodiment of the instant compositions is a single composition adapted for oral administration comprised of a therapeutically effective amount of a COX-2 inhibitor in combination with a therapeutically effective amount of a compound of the invention and a pharmaceutically acceptable carrier. The combination can also be administered in separate dosage forms, each having one of the active agents. If administered in separate dosage forms, the separate dosage forms are administered such that the beneficial effect of each active agent is realized by the patient at substantially the same time.

Common NSAIDs include salicylates such as aspirin, sodium salicylate, choline salicylate, salicylsalicylic acid, diflunisal, and salsalate; indoleacetic acids such as indomethacin and sulindac; pyrazoles such as phenylbutazone, oxyphenbutazone; pyrrolealkanoic acids such as tolmetin; phenylacetic acids such as ibuprofen, feroprofen, flurbiprofen, and ketoprofen; fenamates such as mefanamic acid, and meclofenamate; oxicams such as piroxicam; and naphthaleneacetic acids such as naproxen. Cyclo-oxygenase inhibitors such as COX-1 and COX-2 inhibitors are also NSAIDs.

Employing the human whole blood COX-1 assay and the human whole blood COX-2 assay described in C. Brideau et al, *Inflamm. Res.* 45: 68–74 (1996), herein incorporated by reference, preferably, the compounds have a cyclooxygenase-2 $IC_{50}$ of less than about 2 µM in the human whole blood COX-2 assay, yet have a cyclooxygenase-1 $IC_{50}$ of greater than about 5 µM in the human whole blood COX-1 assay. Also preferably, the compounds have a selectivity ratio of cyclooxygenase-2 inhibition over cyclooxygenase-1 inhibition of at least 10, and more preferably of at least 40. The resulting selectivity may indicate an ability to reduce the incidence of common NSAID-induced side effects.

The inhibitor of cyclooxygenase-2 may be administered at a dosage level up to conventional dosage levels for NSAIDs. Suitable dosage levels will depend upon the antiinflammatory effect of the chosen inhibitor of cyclooxygenase-2, but typically suitable levels will be about 0.001 to 50 mg/kg per day, preferably 0.005 to 30 mg/kg per day, and especially 0.05 to 10 mg/kg per day. The compound may be administered on a regimen of up to 6 times per day, preferably 1 to 4 times per day, and especially once per day.

The dosage regimen utilizing a compound of the invention in combination with the NSAID is selected in accordance with a variety of factors including type, species, age, weight, sex and medical condition of the patient; the severity of the condition to be treated; the route of administration; the renal and hepatic function of the patient; and the particular compound or salt or ester thereof employed. Since two different active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective dosage amounts needed to prevent, counter, or arrest the progress of the condition.

Administration of the drug combination to the patient includes both self-administration and administration to the patient by another person.

Additional active agents may be used in combination with the compound of the invention in a single dosage formulation, or may be administered to the patient in a separate dosage formulation, which allows for concurrent or sequential administration. Examples of additional active agents which may be employed include HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; LDL (low density lipoprotein) receptor inducers; vitamin $B_6$ (also known as pyridoxine) and the pharmaceutically acceptable salts thereof such as the HCl salt; vitamin $B_{12}$ (also known as cyanocobalamin); β-adrenergic receptor blockers; folic acid or a pharmaceutically acceptable salt or ester thereof such as the sodium salt and the methylglucamine salt; and anti-oxidant vitamins such as vitamin C and E and beta carotene.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including anti-hypercholesterolemics (e.g. HMG CoA reductase inhibitors such as lovastatin and simvastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

Unless otherwise stated, all NMR determinations were made using 400 MHz field strength.

Scheme 1
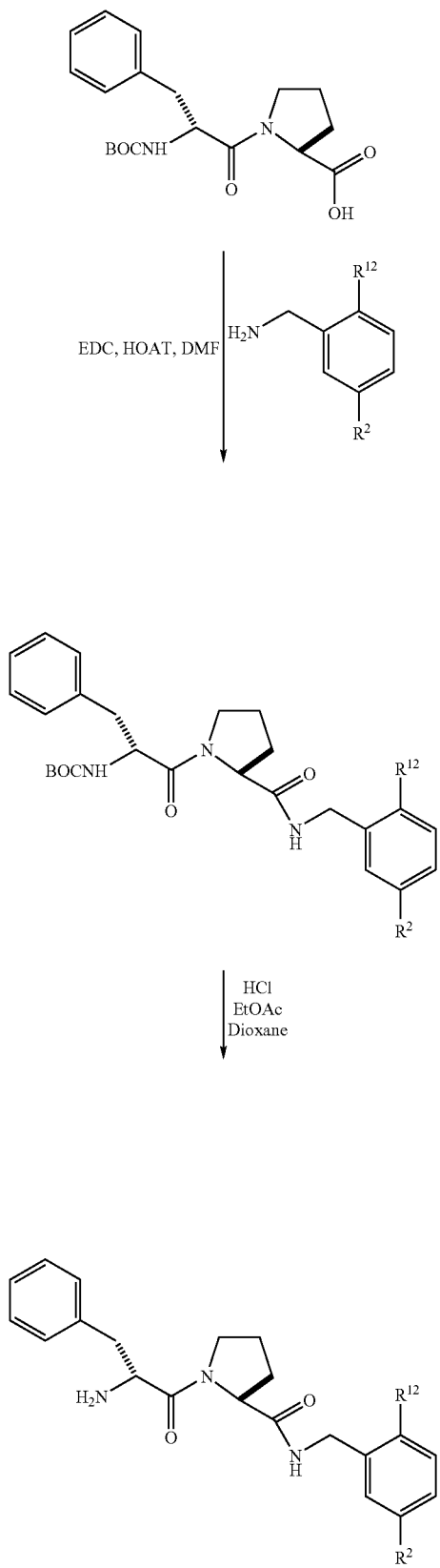
Scheme 2
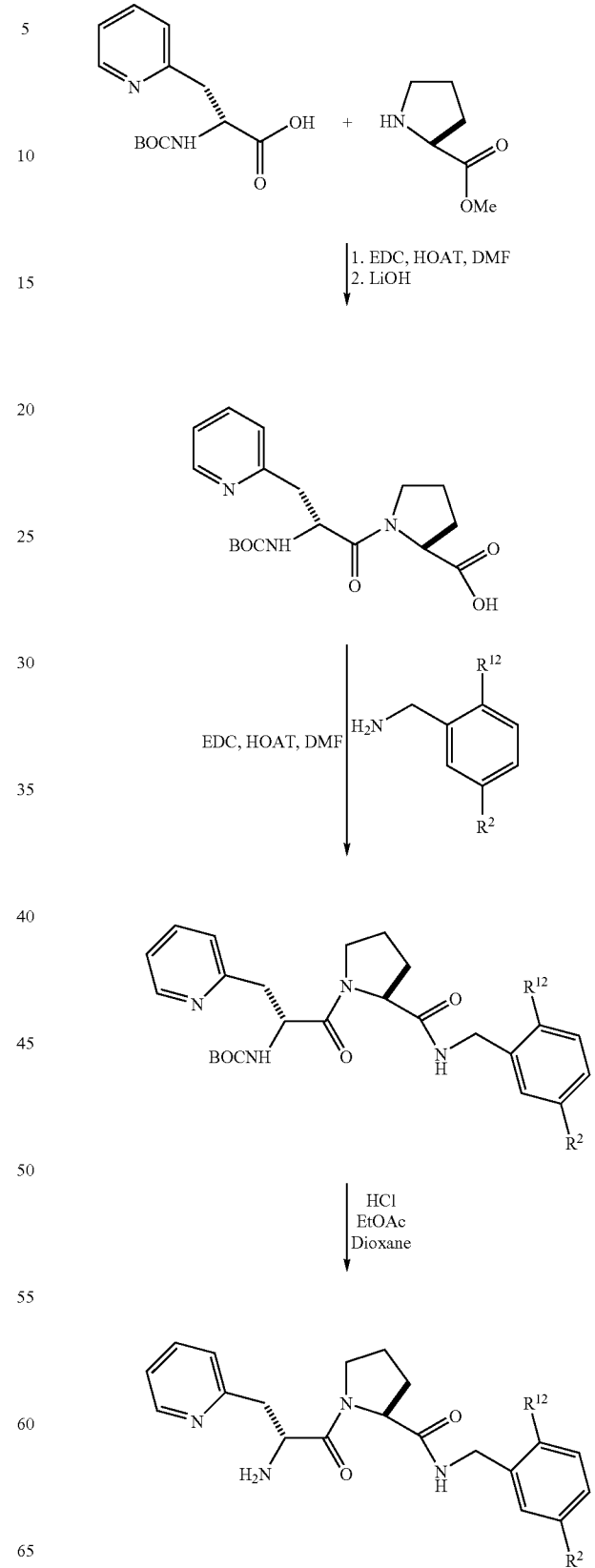

Scheme 3

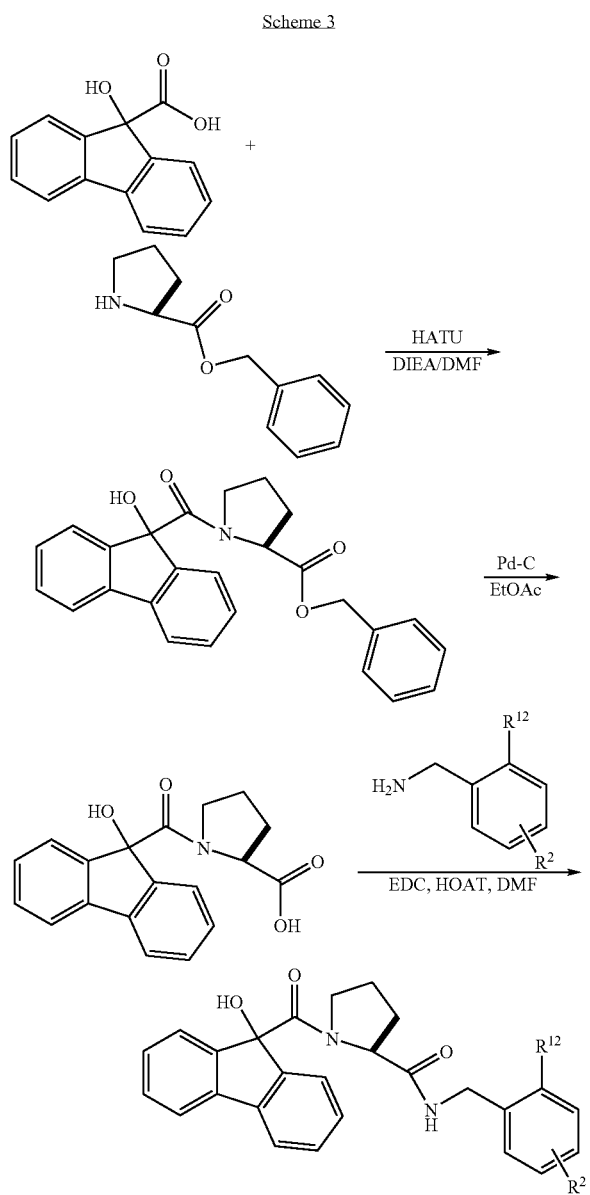

Intermediates useful for preparing compounds of the invention may be prepared as follows:

EXAMPLE I-1

2-[1,2,3]Thiadiazole4-yl-benzylamine

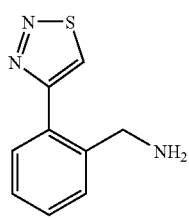

Step A

N'-(1-o-Tolyl-ethylidene)-hydrazinecarboxylic acid ethyl ester (I-1-1)

A solution of 2'-methylacetophenone (0.98 ml, 7.4 mmol), ethyl carbazate (0.81 g, 7.8 mmol) and p-toluenesulfonic acid monohydrate (70 mg, 0.37 mmol) in toluene (30 ml) was heated at reflux temperature with a Dean-Stark apparatus for 2 h. Solvent evaporation and flash chromatography (silica gel, hexane-ethyl acetate, 80:20) gave N'-(1-o-tolyl-ethylidene)-hydrazinecarboxylic acid ethyl ester; $^1$H NMR (CDCl$_3$, 400 MHz) δ 7.72 (bs, 1H), 7.21 (m, 4H), 4.31 (q, 2H, J=7.1 Hz), 2.37 (s, 3H), 2.17 (s, 3H), 1.34 (t, 3H, J=7.1 Hz).

Step B 4-o-Tolyl-[1,2,3]thiadiazole (I-1-2)

To thionyl chloride (1 ml), cooled to 0° C. was added N'-(1-o-tolyl-ethylidene)-hydrazinecarboxylic acid ethyl ester. The reaction mixture was heated to 60° C. for 1 h. Solvent evaporation gave 4-o-tolyl-[1,2,3]thiadiazole; $^1$H NMR (CDCl$_3$, 400 MHz) δ 8.51 (s, 1H), 7.65 (d, 1H, J=7.3 Hz), 7.36 (m, 3H), 2.46 (s, 3H).

Step C 4-(2-Bromomethyl-phenyl)-[1,2,3]thiadiazole (I-1-3)

A solution of 4-o-tolyl-[1,2,3]thiadiazole (100 mg, 0.57 mmol), N-bromosuccinimide (100 mg, 0.57 mmol) and 2,2'-azobisisobutyronitrile (9.4 mg, 0.057 mmol) in chloroform (10 ml) was heated at reflux temperature for ~18 h. Additional chloroform was added and the mixture was washed with water, 5% sodium thiosulfate solution and brine. Drying and solvent evaporation gave 4-(2-bromomethyl-phenyl)-[1,2,3]thiadiazole; $^1$H NMR (CDCl$_3$, 300 MHz) δ 8.87 (s, 1H), 7.67–7.39 (m, 4H), 4.71 (s, 2H).

Step D 4-(2-Azidomethyl-phenyl)-[1,2,3]thiadiazole (I-1-4)

A solution of 4-(2-bromomethyl-phenyl)-[1,2,3]thiadiazole (7.0 g, 0.027 mol) and sodium azide (5.3 g, 0.081 mol) in N,N-dimethylformamide (200 ml) was stirred at room temperature overnight. Ethyl acetate was added and the reaction mixture was washed with water and brine. Drying and solvent evaporation gave an oil; flash chromatography (silica gel, hexane-ethyl acetate, 96:4) gave 4-(2-azidomethyl-phenyl)-[1,2,3]thiadiazole; $^1$H NMR (CDCl$_3$, 300 MHz) δ 8.74 (s, 1H), 7.76 (m, 1H), 7.53 (m, 3H), 4.54 (s, 2H).

Step E

2-[1,2,3]Thiadiazole-4-yl-benzylamine (I-1-5)

A solution of 4-(2-azidomethyl-phenyl)-[1,2,3]thiadiazole (1.0 g, 4.6 mmol), triphenylphosphine (1.4 g, 5.5 mmol) and water (0.12 ml, 6.9 mmol) in tetrahydrofuran (20 ml) was stirred at room temperature overnight. Solvent evaporation and flash chromatography (silica gel, chloroform-2-propanol, 95:5–92:8) gave 2-[1,2,3]thiadiazole-4-yl-benzylamine; $^1$H NMR (CDCl$_3$, 300 MHz) δ 8.87 (s, 1H), 7.67 (d, 1H, J=8 Hz), 7.45 (m, 3H), 3.88 (s, 2H).

EXAMPLE I-2

2-Pyrazol-1-yl-benzylamine trifluoroacetic acid salt

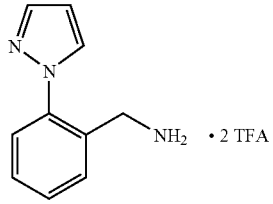

Step A

2-Pyrazol-1-yl-benzoic acid (I-2-1)

To a vigorously stirred mixture of 2-hydrazinobenzoic acid hydrochloride (50 g, 0.27 mol) and malonaldehyde bis-dimethylacetal (43 ml, 0.27 mol) in water (630 ml) was gradually added conc. HCl (30 ml). The reaction mixture was refluxed for 2 h and methanol was evaporated. The inorganic layer was treated with charcoal until colorless, cooled, left for 2 h and filtered. The residue was washed with cold water and dried in the air to give 2-pyrazol-1-yl-benzoic acid; MS (ES+) M+1 189.4 for $C_{10}H_8N_2O_2$.

Step B

2-Pyrazol-1-yl-benzamide (I-2-2)

A solution of 2-pyrazol-1-yl-benzoic acid (50 mg, 0.26 mmol), ammonium chloride (28 mg, 0.52 mmol), 1-(3-dimethylaminopropyl)-3-ethylcarbodiimide hydrochloride (100 mg, 0.52 mmol), 1-hydroxy-7-azabenzotriazole (71 mg, 0.52 mmol) and diisopropylethylamine (0.17 ml, 1.0 mmol) in N,N-dimethylformamide (0.75 ml) was stirred at room temperature for 5 h. Water was added and the reaction mixture was extracted with ethyl acetate. Drying and solvent evaporation gave 2-pyrazol-1-yl-benzamide; $^1$H NMR (CD$_3$OD, 400 MHz) δ 7.92 (d, 1H, J=2.4 Hz), 7.70–7.48 (m, 5H), 6.49 (m, 1H).

Step C

2-Pyrazol-1-yl-benzylamine trifluoroacetic acid salt (I-2-3)

A solution of 2-pyrazol-1-yl-benzamide (68 mg) and borane-tetrahydrofuran complex (1M solution in tetrahydrofuran, 1.4 ml, 1.4 mmol) in tetrahydrofuran (2 ml) was heated at reflux temperature for 2 h. Hydrochloric acid (1M solution in water, 2.8 ml) was added and the reaction mixture was heated at reflux temperature for 30 minutes. The solution was neutralized with 1N sodium hydroxide, concentrated to remove tetrahydrofuran and extracted with chloroform. Drying and solvent evaporation gave an oil; purification by reverse phase preparative HPLC (5% to 95% CH$_3$CN in water containing 0.1% TFA, C18 PRO YMC 20×150 mm) gave 2-pyrazol-1-yl-benzylamine trifluoroacetic acid salt; $^1$H NMR (CDCl$_3$, 400 MHz) δ 8.80 (bs, 2H), 7.80 (m, 2H), 7.62–7.37 (m, 4H), 6.56 (t, 1H, J=2.2 Hz), 4.07 (s, 2H).

EXAMPLE I-3

2-(1H-Imidazol-2-yl)-benzylamine

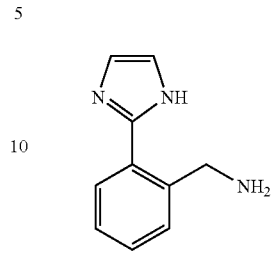

Step A

2-Cyano-benzimidic acid ethyl ester hydrochloride (I-3-1)

A suspension of phthalonitrile (70 g, 0.55 mol) in ethanol (100 ml) and chloroform (200 ml) was warmed and then cooled to 0° C. The reaction mixture was saturated with HCl (g) and then aged at 0° C. for 2 weeks. The resultant precipitate was filtered and washed with chloroform. Dilution of the filtrate with ether produced additional 2-cyano-benzimidic acid ethyl ester hydrochloride.

Step B 2-(1H-Imidazol-2-yl)-benzonitrile hydrochloride (I-3-2)

A solution of 2-cyano-benzimidic acid ethyl ester hydrochloride (43 g, 0.20 mol) and 2,2-diethoxy-ethylamine (30 ml, 0.21 mol) in methanol (430 ml) was aged at room temperature for 1 h. The reaction mixture was concentrated to remove methanol and conc. sulfuric acid (110 ml) was added. After heating on a steam bath for 1.5 h, the reaction mixture was diluted with water (700 ml) and extracted with chloroform. The aqueous phase was made strongly basic with sodium hydroxide and extracted with chloroform. Hydrochloric acid (12N) was added to give pH 3-4, tar was filtered and the filtrate was concentrated. The resultant brown solid was sublimed at 200–220° C. The purified solid was dissolved in hydrochloric acid solution (6N, 110 ml), byproducts filtered and the filtrate concentrated. The residue was diluted with ethanol (100–120 ml) containing hydrochloric acid (12N, 1 ml), boiled briefly and filtered. Further concentration and cooling of the filtrate gave 2-(1H-imidazol-2-yl)-benzonitrile hydrochloride (1.5 g). The filtrate was concentrated further and diluted with acetone. Filtration gave 2-(1H-imidazol-2-yl)-benzoic acid hydrochloride (7.3 g). Dilution of the filtrate with acetone and filtration of the resultant solid gave additional 2-(1H-imidazol-2-yl)-benzonitrile hydrochloride; mp 200–204° C.; IR 4.5μ.

Step C 2-(1H-Imidazol-2-yl)-benzonitrile (I-3-3)

To a solution of 2-(1H-imidazol-2-yl)-benzonitrile hydrochloride (3 g, 0.014 mol) in water (20 ml) was added sodium hydroxide solution (2.5 N, 5 ml). Filtration of the resultant precipitate and recrystallization from ethyl acetate gave 2-(1H-imidazol-2-yl)-benzonitrile; Anal. Calcd. For $C_{10}H_7N_3$: C, 70.99; H, 4.17; N, 24.84. Found: C, 70.74; H, 4.08; N, 25.24.

Step D 2-(1H-Imidazol-2-yl)-benzylamine (I-3-4)

A solution of 2-(1H-imidazol-2-yl)-benzonitrile (50 mg, 0.30 mmol) in ethanol saturated with ammonia (5 ml) was stirred in the presence of Raney nickel (50% slurry in water, washed with ethanol, catalytic amount) under a hydrogen atmosphere for 2 h. The reaction mixture was filtered over celite and concentrated to give 2-(1H-imidazol-2-yl)-benzylamine; ¹H NMR (CDCl₃, 400 MHz) δ 8.13 (d, 1H, J=7.5 Hz), 7.42 (m, 1H), 7.28 (m, 2H), 7.18 (bs, 2H), 3.96 (s, 2H).

EXAMPLE I-4

2-(1H-Pyrazol-3-yl)-benzylamine hydrochloride salt

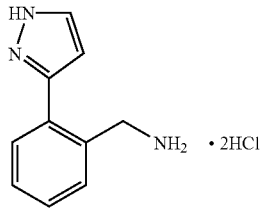

Step A 1-(Tetrahydro-pyran-2-yl)1H-pyrazole (I4-1)

To pyrazole (14.3 g, 0.21 mol) was added 3,4-dihydro-2H-pyran (29 ml, 0.315 mol) and, after complete dissolving, trifluoroacetic acid (0.1 ml, 0.0013 mol) was added to the obtained solution. The reaction mixture was refluxed for 5 h, sodium hydride (0.2 g, 0.008 mol) was added, and the mixture was distilled to give 1-(tetrahydro-pyran-2-yl)1H-pyrazole; b.p. ~60–65° C./0.5–1 torr.

Step B

1H-Pyrazol-3-ylboronic acid (I-4-2)

To a solution of 1-(tetrahydro-pyran-2-yl)1H-pyrazole (7.61 g, 0.0525 mol) in dry THF (50 ml), a 1.6M hexane solution of BuLi (33 ml) was added dropwise at −70° C. A white bulky precipitate formed immediately. Triisopropyl borate (12.7 ml, 0.055 mol) was added over 10 min at the same temperature (−70° C.), and kept at this temperature for 1 h. Then the mixture was decomposed with 2 eq. of 2M HCl under intensive stirring to give a white bulky precipitate. During decomposition, the temperature rose from −70° C. to 20° C. The precipitate was filtered off, washed with water and benzene (until the disappearance of a typical smell) to give 1H-pyrazol-3-ylboronic acid; ¹H NMR (D₂O) δ 7.47 (d, 1H), 6.20 (d, 1H).

Step C tert-Butyl-2-bromobenzylcarbamate (I4-3)

To a solution of 2-bromobenzylamine hydrochloride (11.12 g, 0.05 mol) in dimethylformamide (50 ml) was added di-tert-butyl dicarbonate (10.91 g, 0.05 mol) and triethylamine (3.66 ml, 0.05 mol). The reaction mixture was stirred at room temperature overnight. Saturated sodium carbonate solution was added and the mixture was extracted with ethyl acetate. The combined organic layers were washed with brine. Drying and solvent evaporation gave tert-butyl-2-bromobenzylcarbamate; MS (ES+) M+1 286.4 for C₁₂H₁₆BrNO₂.

Step D tert-Butyl-2-(1H-pyrazol-3-yl)benzylcarbamate (I-4-4)

To a solution of 1H-pyrazol-3-ylboronic acid (156 mg, 1.4 mmol), tetrakis(triphenylphosphine)palladium(0) (242 mg, 0.21 mmol), and sodium carbonate (222 mg, 2.1 mmol) in dimethylformamide (2 ml), was added tert-butyl-2-bromobenzylcarbamate (200 mg, 0.699 mmol). The suspension was stirred at 100° C. for 2 h, cooled to room temperature, poured onto saturated sodium bicarbonate and extracted with ethyl acetate. The combined organic layers were washed with saturated sodium chloride, dried with magnesium sulfate and concentrated in vacuo. The crude material was passed through silica (ISCO, 0–30% ethyl acetate/hexane) to give tert-butyl 2-(1H-pyrazol-3-yl)benzylcarbamate; MS (ES+) M+1 274.1 for C₁₅H₁₉N₃O₂.

Step E 2-(1H-Pyrazol-3-yl)-benzylamine hydrochloride salt (I-4-5)

Hydrogen chloride gas was bubbled through a 0° C. solution of tert-butyl 2-(1H-pyrazol-3-yl)benzylcarbamate (60 mg, 0.220 mmol) in ethyl acetate (5 ml) for 2 min and stirred for 40 min. A precipitate formed, and the suspension was concentrated in vacuo to give 2-(1H-pyrazol-3-yl)-benzylamine hydrochloride salt; MS (ES+) M+1 174.1 for C₁₀H₁₁N₃.

EXAMPLE I-5

2-Imidazol-1-yl-benzylamine

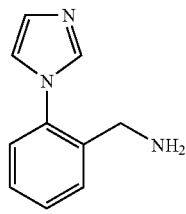

Step A

2-Imidazol-1-yl-benzonitrile (I-5-1)

To a solution of 1H-imidazole (0.61 g, 9.0 mmol) in dimethylformamide (8 ml) was added sodium hydride (60% in oil, 0.36 g, 9.0 mmol) and the reaction mixture was stirred at room temperature for 40 min. 2-Fluoro-benzonitrile (0.9 ml, 8.2 mmol) was added and the reaction was stirred at room temperature for 45 min, heated to 60° C. for 45 min and then stirred at room temperature overnight. Ethyl acetate was added and the mixture was washed with water and brine. Drying and solvent evaporation gave 2-imidazol-1-yl-benzonitrile; ¹H NMR (CDCl₃, 400 MHz) δ 7.86 (bs, 1H), 7.84 (m, 1H), 7.75 (m, 1H), 7.54 (m, 1H), 7.47 (dd, 1H, J=8.1 Hz, J=1 Hz), 7.36 (m, 1H), 7.27 (m, 1H).

Step B

2-Imidazol-1-yl-benzylamine (I-5-2)

A solution of 2-imidazol-1-yl-benzonitrile (200 mg, 1.2 mmol) in ethanol saturated with ammonia (20 ml) was stirred in the presence of Raney nickel (50% slurry in water, washed with ethanol, catalytic amount) under a hydrogen atmosphere for 4 h. The reaction mixture was filtered over celite and concentrated to give 2-Imidazol-1-yl-benzylamine; ¹H NMR (CDCl₃, 400 MHz) δ 7.69 (bs, 1H), 7.57 (m, 1H), 7.47 (m, 1H), 7.38 (m, 1H), 7.27 (m, 1H), 7.22 (bs, 1H), 7.16 (m, 1H), 3.73 (s, 2H).

EXAMPLE I-6

2-(1H-Tetrazol-5-yl)-benzylamine hydrochloride salt

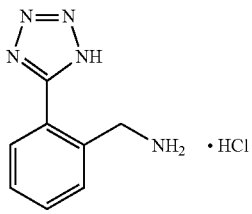

Step A

2-Azidomethyl-benzonitrile (I-6-1)

A solution of 2-bromomethyl-benzonitrile (1.0 g, 5.1 mmol) and sodium azide (0.40 g, 6.1 mmol) in dimethylformamide (10 ml) was stirred at room temperature for 2 h. Ethyl acetate was added and the reaction mixture was washed with water and brine. Drying and solvent evaporation gave 2-azidomethyl-benzonitrile; $^1$H NMR (CDCl$_3$, 400 MHz) δ 7.71 (d, 1H, J=7.7 Hz), 7.64 (m, 1H), 7.53 (d, 1H, J=7.8 Hz), 7.47 (t, 1H, J=7.6 Hz), 4.62 (s, 2H).

Step B (2-Cyano-benzyl)-carbamic acid tert-butyl ester (I-6-2)

A solution of 2-azidomethyl-benzonitrile (0.59 g, 3.7 mmol), tin (II) chloride (1.0 g, 5.5 mmol) and di-tert-butyl dicarbonate (1.2 g, 5.5 mmol) in methanol (16 ml) and tetrahydrofuran (8 ml) was stirred at room temperature for 1 h. Concentration and flash chromatography (silica gel, hexane-ethyl acetate, 85:15) gave (2-cyano-benzyl)carbamic acid tert-butyl ester; $^1$H NMR (CDCl$_3$, 400 MHz) δ 7.64 (d, 1H, J=7.8 Hz), 7.58 (m, 1H), 7.52 (m, 1H), 7.37 (m, 1H), 5.12 (bs, 1H), 4.50 (d, 2H, J=6 Hz), 1.45 (s, 9H).

Step C

[2-(1H-Tetrazol-5-yl)-benzyl]-carbamic acid tert-butyl ester (I-6-3)

A solution of (2-cyano-benzyl)-carbamic acid tert-butyl ester (35 mg, 0.15 mmol), sodium azide (49 mg, 0.75 mmol), ammonium chloride (40 mg, 0.75 mmol) in dimethylformamide (0.5 ml) was heated to 110° C. for 8 h. After cooling to room temperature, ethyl acetate was added and the resultant solid filtered. Concentration of the filtrate gave [2-(1H-tetrazol-5-yl)-benzyl]-carbamic acid tert-butyl ester; $^1$H NMR (CD$_3$OD, 400 MHz) δ 7.71(d, 1H, J=7.5 Hz), 7.58 (m, 2H), 7.48 (m, 1H), 4.44 (s, 2H), 1.42 (s, 9H).

Step D 2-(1H-Tetrazol-5-yl)-benzylamine hydrochloride salt (I-6-4)

Through a solution of [2-(1H-tetrazol-5-yl)-benzyl]-carbamic acid tert-butyl ester (33 mg) in ethyl acetate (15 ml), cooled to 0° C. was bubbled HCl (g) for 5 min. The reaction was stirred at room temperature for 0.5 h. Nitrogen was bubbled through the reaction mixture and ether was added. Filtration gave 2-(1H-tetrazol-5-yl)-benzylamine hydrochloride salt; $^1$H NMR (CD$_3$OD, 400 MHz) δ 7.86 (d, 1H, J=7.7 Hz), 7.79 (m, 1H), 7.69 (m, 1H), 7.63 (m, 1H), 4.36 (s, 2H).

EXAMPLE I-7

2-(1-Methyl-1H-tetrazol-5-yl)-benzylamine hydrochloride salt

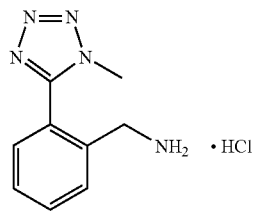

Step A

[2-(1-Methyl-1H-tetrazol-5-yl)-benzyl]-carbamic acid tert-butyl ester (I-7-1)

A solution of [2-(1H-tetrazol-5-yl)-benzyl]-carbamic acid tert-butyl ester (0.23 g, 0.84 mmol, preparation described in example I-6, Step C), crushed potassium carbonate (0.58 g, 4.2 mmol) and iodomethane (0.26 ml, 4.2 mmol) in dimethylformamide (4.7 ml) was stirred at room temperature for 1 h. Water was added and the reaction mixture was extracted with chloroform. Drying and solvent evaporation gave a mixture of regioisomers; separation and purification by reverse phase preparative HPLC (5% to 95% CH$_3$CN in water containing 0.1% TFA, C18 PRO YMC 20×150 mm) gave [2-(1-methyl-1H-tetrazol-5-yl)-benzyl]-carbamic acid tert-butyl ester; $^1$H NMR (CDCl$_3$, 400 MHz) δ 7.66 (d, 1H, J=7.4 Hz), 7.58 (m, 1H), 7.46 (m, 1H), 7.33 (d, 1H, J=7.6 Hz), 4.17 (d, 2H, J=6.3 Hz), 4.05 (s, 3H), 1.41 (s, 9H) and [2-(2-methyl-2H-tetrazol-5-yl)-benzyl]-carbamic acid tert-butyl ester; $^1$H NMR (CDCl$_3$, 400 MHz) δ 8.06 (d, 1H, J=7.4 Hz), 7.61 (d, 1H, J=7 Hz), 7.44 (m, 2H), 5.82 (bs, 1H), 4.52 (d, 2H, J=6.5 Hz), 4.44 (s, 3H), 1.43 (s, 9H).

Step B 2-(1-Methyl-1H-tetrazol-5-yl)-benzylamine hydrochloride salt (I-7-2)

Through a solution of [2-(1-methyl-1H-tetrazol-5-yl)-benzyl]-carbamic acid tert-butyl ester (10 mg) in ethyl acetate (5 ml), cooled to 0° C. was bubbled HCl (g) for 5 min. The reaction was stirred at room temperature for 0.5 h. Nitrogen was bubbled through the reaction mixture. Concentration from ethyl acetate gave 2-(1-methyl-1H-tetrazol-5-yl)-benzylamine hydrochloride salt; $^1$H NMR (CD$_3$OD, 400 MHz) δ 7.75 (m, 4H), 4.18 (s, 3H), 4.11 (m, 2H).

EXAMPLE I-8

2-(2-Methyl-2H-tetrazol-5-yl)-benzylamine hydrochloride salt

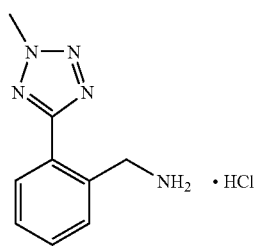

Step A 2-(2-Methyl-2H-tetrazol-5-yl)-benzylamine hydrochloride salt (I-8-1)

Through a solution of [2-(2-methyl-2H-tetrazol-5-yl)-benzyl]-carbamic acid tert-butyl ester (15 mg, preparation described in example I-7, Step A) in ethyl acetate (5 ml), cooled to 0° C. was bubbled HCl (g) for 5 min. The reaction was stirred at room temperature for 0.5 h. Nitrogen was bubbled through the reaction mixture. Concentration from ethyl acetate gave 2-(2-methyl-2H-tetrazol-5-yl)-benzylamine hydrochloride salt; $^1$H NMR (CD$_3$OD, 400 MHz) δ 8.24 (m, 1H), 7.63 (m, 3H) 4.48 (s, 3H), 4.47 (m, 2H).

EXAMPLE 1

2-Tetrazol-1-yl-benzylamine

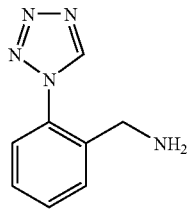

Step A. 2-Tetrazol-1-yl-benzoic acid

A suspension of 2-aminobenzoic acid (6.0 g, 0.044 mol), trimethyl orthoformate (14.2 ml, 0.13 mol) and sodium azide (8.4 g, 0.13 mol) in glacial acetic acid (150 ml) was stirred at room temperature for 2 h. Filtration and concentration from toluene gave 2-Tetrazol-1-yl-benzoic acid; $^1$H NMR (CD$_3$OD, 400 MHz) δ 9.47 (s, 1H), 8.19 (dd, 1H, J=7.7 Hz, J=1.6 Hz), 7.79 (m, 2H), 7.61 (dd, 1H, J=7.7 Hz, J=1.5 Hz).

Step B. 2-Tetrazol-1-yl-benzamide

A solution of 2-Tetrazol-1-yl-benzoic acid (1.0 g, 5.2 mmol), ammonium chloride (0.56 g, 10.4 mmol), 1-(3-dimethylaminopropyl)-3-ethylcarbodiimide hydrochloride (2.0 g, 10.4 mmol), 1-hydroxy-7-azabenzotriazole (1.4 g, 10.4 mmol) and diisopropylethylamine (3.6 ml, 20.8 mmol) in N,N-dimethylformamide (15 ml) was stirred at room temperature overnight. Water was added and the reaction mixture was extracted with ethyl acetate. The combined organic layers were washed with brine. Drying and solvent evaporation gave 2-Tetrazol-1-yl-benzamide; $^1$H NMR (CD$_3$OD, 400 MHz) δ 9.44 (s, 1H), 7.72 (m, 4H).

Step C. 2-Tetrazol-1-yl-benzonitrile

To a solution of 2-Tetrazol-1-yl-benzamide (1.5 g, 7.9 mmol) in tetrahydrofuran (50 ml) was added (methoxycarbonylsulfamoyl)ammonium hydroxide, inner salt (2.8 g, 11.8 mmol) in three portions over 1.5 h. Water was added and the reaction mixture was extracted with ethyl acetate. The combined organic layers were washed with brine. Drying and solvent evaporation gave 2-Tetrazol-1-yl-benzonitrile; $^1$H NMR (CDCl$_3$, 400 MHz) δ 9.27 (s, 1H), 7.90 (m, 3H), 7.72 (m, 1H).

Step D. 2-Tetrazol-1-yl-benzylamine

A solution of 2-Tetrazol-1-yl-benzonitrile (1.3 g, 7.6 mmol) in ethanol saturated with ammonia (125 ml) was stirred in the presence of Raney nickel (50% slurry in water, washed with ethanol, catalytic amount) under a hydrogen atmosphere overnight. The reaction mixture was filtered over celite and concentrated to give 2-Tetrazol-1-yl-benzylamine; $^1$H NMR (CDCl$_3$, 400 MHz) δ 9.28 (s, 1H), 7.59 (m, 2H), 7.47 (m, 2H), 3.70 (s, 2H).

EXAMPLE 2

5-Chloro-2-tetrazol-1-yl-benzylamine

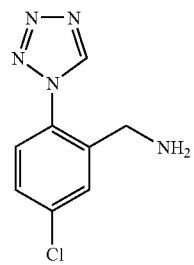

Step A: 5-Chloro-2-(1H-tetraazol-1-yl)benzoic acid

A suspension of 2-amino-5-chloro-benzoic acid (5.0 g, 0.029 mol), trimethyl orthoformate (9.5 mL, 0.087 mol) and sodium azide (5.6 g, 0.087 mol) in glacial acetic acid (105 mL) was stirred at room temperature for 2 h. Filtration and concentration from toluene gave 5-chloro-2-(1H-tetraazol-1-yl)benzoic acid (4.0 g, 62%); $^1$H NMR (400 MHz, CD$_3$OD): δ 9.47 (s, 1H), 8.16 (d, J=2.5 Hz, 1H), 7.83 (dd, J=2.5, 8.5 Hz, 1H), 7.62 (d, J=8.5 Hz, 1H).

Step B: 5-Chloro-2-(1H-tetraazol-1-yl)benzamide

A solution of 5-chloro-2-(1H-tetraazol-1-yl)benzoic acid (2.0 g, 8.9 mmol), ammonium chloride (0.95 g, 17.8 mmol), 1-(3-dimethylaminopropyl)-3-ethylcarbodiimide hydrochloride (3.4 g, 17.8 mmol), HOAt (2.4 g, 17.8 mmol) and DIEA (6.2 mL, 35.6 mmol) in DMF (26 mL) was stirred at room temperature overnight. Water was added and the reaction mixture was extracted with ethyl acetate. The combined organic layers were washed with brine. Drying and solvent evaporation gave 5-chloro-2-(1H-tetraazol-1-yl)benzamide (2.3 g); $^1$H NMR (400 MHz, CD$_3$OD): δ 9.44 (s, 1H), 7.82 (d, J=2.3 Hz, 1H), 7.75 (dd, J=2.3, 8.5 Hz, 1H), 7.66 (d, J=8.5 Hz, 1H).

Step C: 5-Chloro-2-(1H-tetraazol-1-yl)benzonitrile

To a solution of 5-chloro-2-(1H-tetraazol-1-yl)benzamide (1.0 g, 4.5 mmol) in THF (29 mL) was added (methoxycarbonylsulfamoyl)ammonium hydroxide, inner salt (2.1 g, 8.8 mmol) in five portions over 5 h. Water was added and the reaction mixture was extracted with ethyl acetate. The combined organic layers were washed with brine. Drying and solvent evaporation gave 5-chloro-2-tetrazol-1-yl-benzonitrile (0.83 g, 90%); $^1$H NMR (400 MHz, CDCl$_3$): δ 9.26 (s, 1H), 7.90 (d, J=1.0 Hz, 1H,), 7.85 (m, 2H).

Step D: 5-Chloro-2-tetrazol-1-yl-benzylamine

A solution of 5-chloro-2-(1H-tetraazol-1-yl)benzonitrile (113 mg, 0.55 mmol) in ethanol saturated with ammonia (20 mL) was stirred in the presence of Raney nickel (50% slurry in water, washed with ethanol, catalytic amount) under a hydrogen atmosphere for 1 h. The reaction mixture was filtered through Celite and concentrated to give 5-chloro-2-tetrazol-1-yl-benzylamine (58 mg, 50%); $^1$H NMR (400 MHz, CDCl$_3$): δ 9.24 (s, 1H), 7.64 (d, J=2.2 Hz, 1H), 7.46 (m, 1H), 7.38 (m, 1H), 3.68 (s, 2H).

EXAMPLE 3

C-(3-[1,2,4]Triazol-1-yl-pyridin-2-yl)-methylamine di hydrochloride

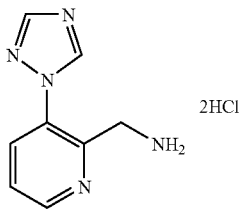

Step A. 3-[1,2,4]Triazol-1-yl-pyridine-2-carbonitrile

To a solution of 2-cyano-3-fluoro-pyridine (2.99 g, 24.49 mmol, preparation described in case 20443, filed Jun. 4, 1999) in DMF (30 ml) is added cesium carbonate (2.03 g, 29.39 mmol) and 1,2,4-triazole (2.03 g, 29.39 mmol) and the reaction mixture is stirred at 65° C. for 4 h. After cooling to room temperature, the mixture is diluted with water and extracted with EtOAc 3 times. The aqueous layer is saturated with LiCl and further extracted with EtOAc. The combined organic layer is dried on sodium sulfate, concentrated in vacuo. The crude product is purified by flash chromatography (silica gel, 2% MeOH containing 10% NH$_4$OH in CH$_2$Cl$_2$ to 6%) to give 3-[1,2,4]Triazol-1-yl-pyridine-2-carbonitrile. $^1$H NMR (CDCl$_3$, 400 MHz) δ 8.95 (s, 1H); 8.8 (d, J=4 Hz, 1 H); 8.24 (s, 1H); 8.22 (d, J=8.5 Hz, 1 H); 7.75 (dd, J=4, 8.5 Hz, 1 H).

Step B. (3-[1,2,4]Triazol-1-yl-pyridin-2-ylmethyl)-carbamic acid tert-butyl ester To a suspension of Raney Nickel (ca. 3 pipets of suspension in water, washed/decanted with EtOH several times) in MeOH saturated with NH$_3$ (200 ml) was added 3-[1,2,4]Triazol-1-yl-pyridine-2-carbonitrile (3.745 g, 21.88 mmol). The mixture was hydrogenated at 55 Psi for 18 h. The reaction mixture was filtered on celite under a flow of argon and the filtrate was concentrated in vacuo. To a solution of the crude material in CH$_2$Cl$_2$ (100 ml) and MeOH (10 ml) was added di-tert-butyl dicarbonate (6.2 g, 28.4 mmol) and the reaction mixture was stirred at room temperature for 30 min. The crude product obtained by concentration in vacuo is purified by flash chromatography (silica gel, 2% MeOH containing 10% NH$_4$OH in CH$_2$Cl$_2$ to 6%) to give (3-[1,2,4]Triazol-1-yl-pyridin-2-ylmethyl)-carbamic acid tert-butyl ester. $^1$H NMR (CDCl$_3$, 400 MHz) δ 8.72 (d, J=4.8 Hz, 1 H); 8.42 (s, 1H); 8.18 (s, 1H); 7.70 (d, J=7.6 Hz, 1 H); 7.40 (dd, J=4.8, 7.6 Hz, 1 H); 5.85 (bs, 1 H); 4.43 (d, J=5.4 Hz, 2 H); 1.45 (s,9 H).

Step C. C-(3-[1,2,4]Triazol-1-yl-pyridin-2-yl)-methylamine di hydrochloride

Through a solution of (3-[1,2,4]Triazol-1-yl-pyridin-2-ylmethyl)-carbamic acid tert-butyl ester (4.08 g) in CH$_2$Cl$_2$ (100 ml) and MeOH (20 ml) cooled to 0° C. is bubbled HCl (g) for 10 min. The flask is sealed and the reaction mixture is stirred at room temperature for 18 h. Nitrogen is bubbled through the reaction mixture for 5 min and the reaction mixture is concentrated to give C-(3-[1,2,4]Triazol-1-yl-pyridin-2-yl)-methylamine di hydrochloride as a white solid. $^1$H NMR (CD$_3$OD, 400 MHz) δ 9.67 (s, 1H); 8.85 (d, J=5.3 Hz, 1 H); 8.72 (s, 1H); 8.18 (d, J=8 Hz, 1 H); 7.7 (dd, J=5.3, 8 Hz, 1 H); 4.45 (s, 2 H).

EXAMPLE 4

5-Chloro-2-[1,2,4]triazol-1-yl-benzylamine

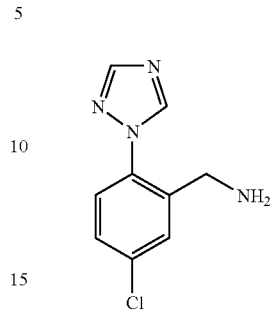

Step A. 5-Chloro-2-[1,2,4]triazol-1-yl-benzonitrile

To a solution of 2,5-dichlorobenzonitrile (10 g, 58.1 mmol) in DMF (100 ml) is added cesium carbonate (22.7 g, 69.8 mmol) and 1,2,4-triazole (4.8 g, 69.8 mmol) and the reaction mixture is stirred at 65° C. for 5.5 h, at 75° C. for 16 h, at 85° C. for 7 h. More 1,2,4-triazole (5 g) is added and the reaction mixture is stirred at 85° C. for 18 h and at 100° C. for 4 h. After cooling to room temperature, the mixture is diluted with water and extracted with EtOAc 3 times. The combined organic layer is washed with aqueous LiCl, dried on sodium sulfate, concentrated in vacuo to give 5-Chloro-2-[1,2,4]triazol-1-yl-benzonitrile as a white solid which is used in the next step without further purification.

Step B. 5-Chloro-2-[1,2,4]triazol-1-yl-benzylamine

To a suspension of 5-Chloro-2-[1,2,4]triazol-1-yl-benzonitrile (11.87 g, 58 mmol) in EtOH saturated with NH$_3$ (500 ml) was added Raney Nickel (ca. 5 pipets of suspension in water, washed/decanted with EtOH several times). The mixture was hydrogenated at 1 atm for 26 h. The reaction mixture was filtered on celite under a flow of argon and the filtrate was concentrated in vacuo. The crude product was purified by flash chromatography (silica gel, 5% MeOH containing 10% NH$_4$OH in CH$_2$Cl$_2$ to 10%) to give 5-Chloro-2-[1,2,4]triazol-1-yl-benzylamine as a white solid. $^1$H NMR (CDCl$_3$, 400 MHz) δ 8.47 (s, 1H); 8.14 (s, 1H); 7.58 (d, J=2.3 Hz, 1 H); 7.38 (dd, J=2.3, 7.9 Hz, 1 H); 7.30 (d, J=7.9 Hz, 1 H); 3.70 (s, 2 H). 8.72 (d, J=4.8 Hz, 1 H); 8.42 (s, 1H); 8.18 (s, 1H); 7.70 (d, J=7.6 Hz, 1 H); 7.40 (dd, J=4.8, 7.6 Hz, 1 H); 5.85 (bs, 1 H); 4.43 (d, J=5.4 Hz, 2 H); 1.45 (s, 9 H).

EXAMPLE 5

2-(1,2,4-Triazol-1-yl)benzylamine

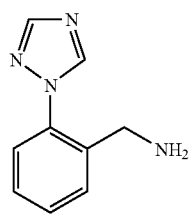

Step A. 2-(1,2,4-triazol-4-yl)cyanobenzene

To a stirred solution of 2-fluorocyanobenzene (5.0 g, 41 mmol) in DMF (75 mL) was added 1,2,4-triazole (3.0 g, 43 mmol) and cesium carbonate (14 g, 43 mmol). The mixture was warmed to 50° C. and stirred under inert atmosphere for 18 h. The mixture was cooled to ambient temperature, diluted with an equal volume of EtOAc, filtered, and the filtrate solvents were removed under reduced pressure. The residue was partitioned between ether (50 mL) and water (100 mL). The undissolved solid was collected by suction filtration and dried under reduced pressure to give 4.6 g of a 10:1 mixture of 2-(1,2,4-triazol-1-yl)cyanobenzene (hplc retention time=2.29 min, method X; TLC Rf=0.6, EtOAc) and 2-(1,2,4-triazol4-yl)cyanobenzene (hplc retention time=1.91 min, method X; TLC Rf=0.1, EtOAc). The mixture was separated by flash chromatography using a gradient elution of 0:100 to 5:95 MeOH:EtOAc to give 2-(1,2,4-triazol-1-yl)cyanobenzene ($^1$H NMR (DMSO-d$_6$) δ 9.19 (s, 1H), 8.37 (s, 1H), 8.10 (d, J=7.6 Hz, 1H), 7.96–7.87 (m, 2H), 7.71 (t, J=7.7 Hz, 1H); mass spec m/z=171 (M$^+$+H)) and 0.38 g of 2-(1,2,4-triazol4-yl)cyanobenzene ($^1$H NMR (DMSO-d$_6$) δ 9.03 (s, 2H), 8.13 (d, J=7.6 Hz, 1H), 7.93(t, J=7.8 Hz, 1H), 7.80 (d, J=7.8 Hz, 1H), 7.74 (t, J=7.7 Hz, 1H); mass spec m/z=171 (M$^+$+H)), both as white solids.

Step B. 2-(1,2,4-triazol-1-yl)-benzylamine

A solution of 2-(1,2,4-triazol-1-yl)cyanobenzene (508 mg, 2.99 mmol) and 25% by weight of palladium on carbon, 10% catalyst (134 mg) in ethanol (75 ml) was placed on a PARR Hydrogenation Apparatus under a hydrogen atmosphere at 55 psi. overnight. The mixture was filtered through celite and concentrated to give 2-(1,2,4-triazol-1-yl)-benzylamine; $^1$H NMR (CD3OD) δ 8.80 (s, 1H), 8.22 (s, 1H), 7.64–7.43 (m, 4H), 3.66 (s, 2H).

EXAMPLE 6

2-(1,2,4-Triazol-4-yl)benzylamine

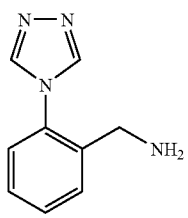

2-(1,2,4-Triazol-4-yl)cyanobenzene (0.3 g; 1.76 mmol) from step A of example 5 was combined with 30% by weight of palladium on carbon, 10% catalyst (100 mg) in ethanol (75 ml) and placed on a PARR Hydrogenation apparatus under a hydrogen atmosphere at 55 psi. for 48 hours. The mixture was filtered through celite and concentrated to give 2-(1,2,4-triazol4-yl)benzylamine; $^1$H NMR (CD3OD) δ 8.77 (s, 2H), 7.69–7.59 (m, 4H), 3.61 (s, 2H).

EXAMPLE 7

3-(Tetrazol-1-yl)-2-aminomethylpyridine

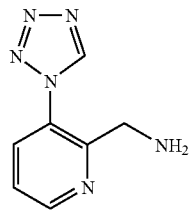

Step A. 3-(tetrazol-1-yl)cyanopyridine

To a stirred solution of tetrazole (1.0 g; 14 mmol) in DMF (150 mL) was added 40% aqueous tetrabutylammonium hydroxide (7.8 g; 12 mmol). The solvent was removed under reduced pressure. To ensure removal of all the water from the tetrabutylammonium hydroxide solution, the residue was redissolved in DMF and the solution was evaporated under reduced pressure. This procedure was repeated a total of three times. The residue was then dissolved in DMF (60 mL) and 3-fluoro-2-cyanopyridine (1.5 g; 12 mmol) was added. The reaction was stirred at ambient temperature under inert atmosphere for four days, at which time hplc analysis indicated about 65% conversion of the 3-fluoro-2-cyanopyridine to new products. The solvent was removed under reduced pressure and the residue was partitioned between EtOAc and water. The EtOAc layer was separated, dried over anhydrous MgSO$_4$, and filtered. The solvent was removed under reduced pressure and the residue was purified by flash chromatography using a gradient elution of 1:4 to 100:0 EtOAc:hexanes to give 3-(tetrazol-1-yl)cyanopyridine as a white crystalline solid (TLC Rf=0.5, 1:1 EtOAc-hexanes; hplc retention time=2.04 min, method X; $^1$H NMR (CDCl$_3$) δ 9.42 (s, 1H), 8.94 (dd, J=1.3, 4.6 Hz, 1H), 8.31 (dd, J=1.3, 8.4 Hz, 1H), 7.87 (dd, J=4.6, 8.4 Hz, 1H).

Step B. 3-(tetrazol-1-yl)-2-aminomethylpyridine

A solution of 3-(tetrazol-1-yl)cyanopyridine (250 mg, 1.45 mmol) and 45% by weight of palladium on carbon, 10% catalyst (110 mg) in ethanol (75 ml) was placed on a PARR Hydrogenation Apparatus under a hydrogen atmosphere at 55 psi. overnight. The mixture was filtered through celite and concentrated to give 3-(tetrazol-1-yl)-2-aminomethylpyridine; $^1$H NMR (CD3OD) δ 9.60 (s, 1H), 8.83–8.81 (m, 1H), 7.99–7.97 (m, 1H), 7.59–7.56 (m, 1H), 3.77 (s, 2H).

EXAMPLE 8

D-Phenylalanyl-N-[2-(1H-tetraazol-1-yl)benzyl]-L-prolinamide hydrochloride

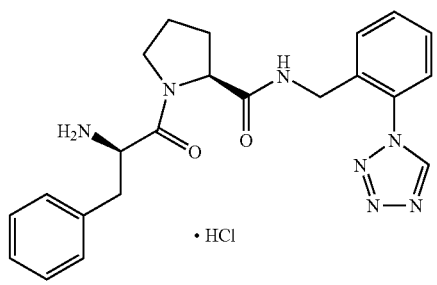

Step A: N-(tert-Butoxycarbonyl)-D-phenylalanyl-N-[2-(1H-tetraazol-1-yl)benzyl]-L-prolinamide trifluoroacetate To a solution of 1-[2-(1H-tetraazol-1-yl)phenyl]methanamine (0.18 mmol, 60 mg), EDC (0.25 mmol, 48 mg), and Boc-D-Phe-Pro-OH (available from Bachem) ((0.17 mmol, 60 mg), in 0.5 mL dimethylformamide, was added HOAT (0.18 mmol, 32 mg). The solution was stirred overnight and purified by prep HPLC to give N-(tert-butoxycarbonyl)-D-Phenylalanyl-N-[2-(1H-tetraazol-1-yl)benzyl]-L-prolinamide trifluoroacetate Mass Spec ES (M+1)=521.1.

Step B: D-Phenylalanyl-N-[2-(1H-tetraazol-1-yl)benzyl]-L-prolinamide hydrochloride Bubbled HCl gas through a 0° C. solution of N-(tert-Butoxycarbonyl)-D-phenylalanyl-N-[2-(1H-tetraazol-1-yl) benzyl]-L-prolinamide trifluoroacetate (0.16 mmol, 83 mg) in 0.500 mL ethylacetate for 2 min. Let stir 1 h and concentrated in vaccuo to give D-Phenylalanyl-N-[2-(1H-tetraazol-1-yl)benzyl]-L-prolinamide, HCl. Mass Spec ES (M+1)=420.1

The following compounds were prepared by procedures similar to those described for Example 8.

EXAMPLE 9

D-Phenylalanyl-N-[5-chloro-2-(1H-tetraazol-1-yl)benzyl]-L-prolinamide hydrochloride

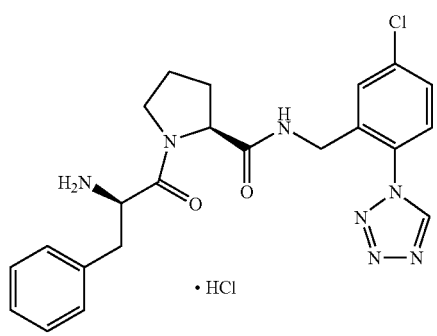

Mass Spec ES (M+1)=454.2

EXAMPLE 10

D-Phenylalanyl-N-[2-(1H-1,2,4-triazol-1-yl)benzyl]-L-prolinamide dihydrochloride

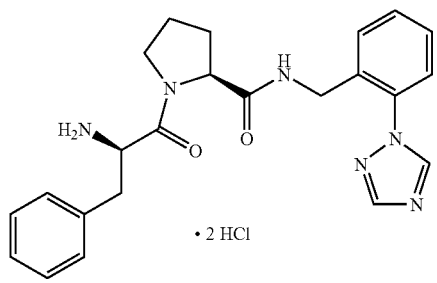

Mass Spec ES (M+1)=419.2

EXAMPLE 11

D-Phenylalanyl-N-[5-chloro-2-(1H-1,2,4-triazol-1-yl)benzyl]-L-prolinamide (bis)hydrochloride

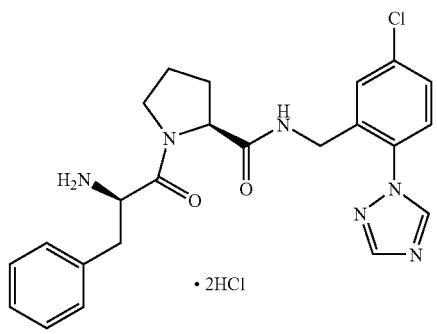

Mass Spec ES (M+1)=453.2

EXAMPLE 12

D-Phenylalanyl-N-{[3-(1H-1,2,4-triazol-1-yl)pyridinium-2-yl]methyl}-L-prolinamide bis(hydrochloride)

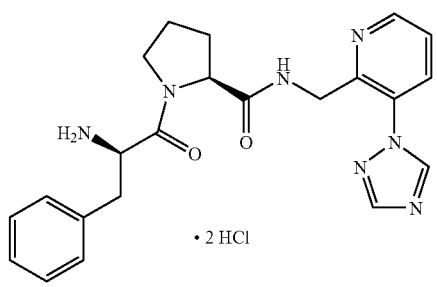

Mass Spec ES (M+1)=420.2

EXAMPLE 13

Phenylalanyl-N-[5-chloro-2-(1H-tetraazol-1-yl)benzyl]-L-prolinamide bis(hydrochloride)

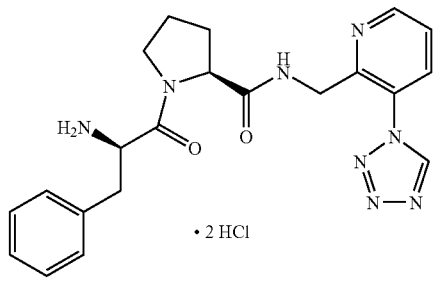

Mass Spec ES (M+1)=421.3

EXAMPLE 14

3-pyridinium-2-yl-D-alanyl-N-[5-chloro-2-(1H-1,2,4-triazol-4-ium-1-yl)benzyl]-L-prolinamide trichloride:

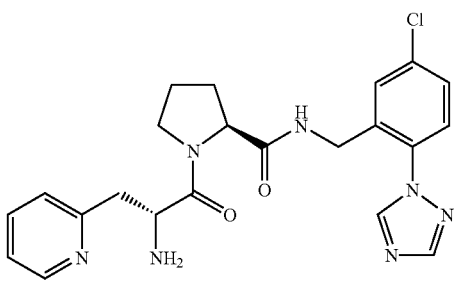

Step A.

N-(tert-butoxycarbonyl)-3-pyridin-2-yl-L-alanyl-L-proline

To a solution of 1.0 g (3.8 mmol) N-(tert-butoxycarbonyl)-3-pyridin-2-yl-L-alanine in 7 ml DMF was added 0.62 g (3.8 mmol) methyl L-prolinate hydrochloride, 0.52 mL (3.8 mmol) triethylamine, 0.51 g (0.38 mmol) HOAt, and 1.1 g (5.7 mmol) EDC. After 3 h at room temperature, the reaction mixture was diluted with 300 ml EtOAc, washed with 200 ml each of saturated NaHCO$_3$ solution, water, and ml brine. The organic layer was dried over Na$_2$SO$_4$, filtered and concentrated in vacuo. Purification by automated flash chromatography (ISCO combiflash, 70 g silica gel, linear gradient 50–100% EtOAc:hexane 30 min then 2–10% MeOH/EtOAc at 60 mL/min) afforded 0.9 g N-(tert-butoxycarbonyl)-3-pyridin-2-yl-L-alanyl-L-proline of which 0.44 g (1.2 mmol) was dissolved in 7 mL MeOH. To this was added 1.2 mL (1.2 mmol, 1M aqueous solution) LiOH and the reaction mixture stirred 6 hours, then another 0.12 ml (0.12 mmol, 1M aqueous solution) portion of LiOH was added and the reaction mixture stirred an additional 16 hrs before addition of 0.12 mL conc. HCl (1.44 mmol, 12M aqueous solution) was added and the reaction concentrated to a foam. $^1$H NMR (CD$_3$OD, 400 MHz) δ 8.47 (m, 1H); 7.78 (m, 1H); 7.34 (m, 2H,); 4.31 (dd, 1H, J=4.21, 8.8 Hz); 3.78 (br m, 1H); 3.54 (br m, 1H); 3.17 (dd, 1H, J=6.23 and 13.5 Hz); 3.02 (m, 2H); 2.3–1.8 (br m, 4H); 1.35 (s, 9H); electrospray mass spectrum 364.

Step B. 3-pyridinium-2-yl-D-alanyl-N-[5-chloro-2-(1H-1,2,4-triazol-4-ium-1-yl)benzyl]-L-prolinamide trichloride:

The title compound is prepared from N-(tert-butoxycarbonyl)-3-pyridin-2-yl-D-alanyl-L-proline and 3-Chloro-2-[1,2,4]triazol-1-yl-benzylamine using a similar procedure as that described above: $^1$H NMR (DMSO-d$_6$, 400 MHz): δ 8.95 (s, 1H), 8.66 (t, 1H, J=5.6 Hz), 8.61 (d, 1H, J=4.4 Hz ), 8.47 (br s, 3H), 8.27 (s, 1H), 7.92 (t, 1H, J=7.9 Hz), 7.55–7.43 (m, 5H), 4.56 (br s, 1H), 4.28–4.11 (m, 3H), 3.37–3.20 (m, 4H), 2.00–1.93 (br s, 1H), 1.88–1.72 (br m, 3H); HRMS (Electrospray): M+H Calcd for C$_{22}$H$_{25}$ClN$_7$O$_2$: 454.1753, Found: 454.1754; TLC: R$_f$=0.38 (80/10/1 of methylene chloride/methanol/concentrated ammonium hydroxide).

EXAMPLE 15

3-pyridinium-2-yl-D-alanyl-N-[5-chloro-2-(1H-tetraazol-1-yl)benzyl]-L-prolinamide dichloride:

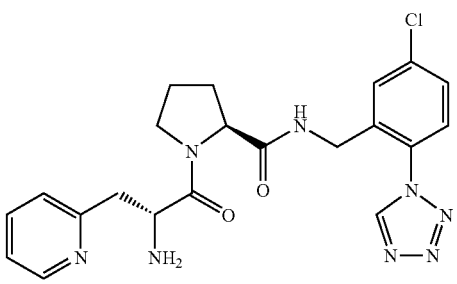

The title compound is prepared using a similar procedure as above from N-(tert-butoxycarbonyl)-3-pyridin-2-yl-D-alanyl-L-proline and 1-[5-chloro-2-(1H-tetraazol-1-yl)phenyl]methanamine. $^1$H NMR (DMSO-d$_6$, 400 MHz): δ 9.89 (s, 1H), 8.73 (t, 1H, J=5.6 Hz), 8.62 (d, 1H, J=4.0 Hz ), 8.59–8.48 (br m, 3H), 7.95 (t, 1H, J=9.5 Hz), 7.61 (br s, 2H), 7.51–7.43 (br m, 3H), 4.55 (br s, 1H), 4.20 (d, 1H, J=7.7 Hz), 4.15–3.97 (m, 2H), 3.41–3.20 (m, 4H), 2.00–1.91 (br s, 1H), 1.83–1.71 (br m, 3H); HRMS (Electrospray): M+H Calcd for C$_{21}$H$_{24}$ClN$_8$O$_2$: 455.1705, Found: 455.1707; TLC: R$_f$=0.39 (80/10/1 of methylene chloride/methanol/concentrated ammonium hydroxide).

EXAMPLE 16

N-[5-chloro-2-(1H-tetraazol-1-yl)benzyl]-1-[(9-hydroxy-9H-fluoren-9-yl)carbonyl]-D-prolinamide

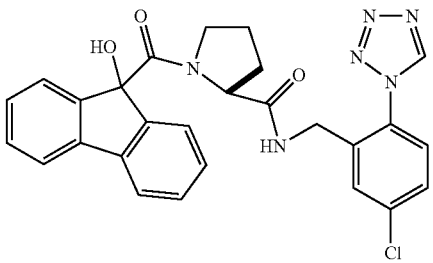

Step A.

9-hydroxy-9-fluorenylcarbonyl-L-proline benzyl ester

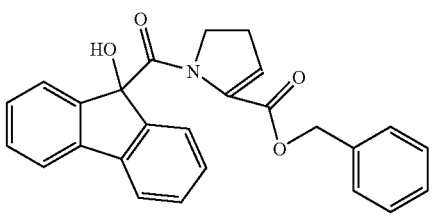

To a solution of 9-hydroxy-9-fluorene carboxylic acid (5.04 g, 22.3 mmol) in N,N-dimethylformamide (30 mL), cooled to 0° C. under nitrogen, was added (O-7-azabenzotriazol-1-y)-1,1,3,3-tetramethyluronium hexafluorophosphate (HATU), (9.32 g, 24.5 mmol), L-proline-benzyl ester hydrochloride (5.93 g, 24.5 mmol), and N,N-diisopropylethylamine (8.5 mL, 48.8 mmol). The mixture was stirred at 0° C. for 3 hours, then concentrated and purified on silica gel (ethyl acetate-hexane, 1:2) to give 9-hydroxy-9-fluorenylcarbonyl-L-proline benzyl ester. HPLC=96%, R.T.=3.7 min; Mass spec.(electrospray) M+1=414.1.

Step B.

9-hydroxy-9-fluorenylcarbonyl-L-proline

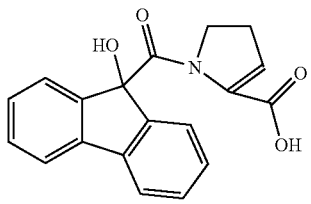

A mixture of 9-hydroxy-9-fluorenylcarbonyl-L-proline benzyl ester (3.8 g, 9.3 mmol) from step 1 above and 10% palladium on carbon (390 mg) in ethyl acetate (100 mL) was stirred under an atmosphere of hydrogen (balloon pressure) for 24 hours. The mixture was filtered through celite and concentrated in vacuo to give 9-hydroxy-9-fluorenylcarbonyl-L-proline. HPLC=90%, R.T.=2.97 min; M+1=324.1; $^1$H NMR (CD$_3$OD, 400 MHz) δ 7.78–7.75 (m, 2H), 7.47–7.32 (m, 6H), 4.49–4.45 (q, 1H 2.42–2.30 (m, 2H), 2.01–1.94 (m, 1H), 1.78–1.71 (m, 1H), 1.58–1.41 (m, 2H).

HPLC Method

Mobile Phase:

gradient: 95:5 to 0:100 A:B over 4.5 minutes; A=water with 0.1% TFA, B=acetonitrile with 0.1% TFA; flow rate: 3.0 mL/min.

Stationary Phase: Zorbax C8 column, 4.5 mm ID×7.5 cm; 3.5 micron

Step C.

N-[5-chloro-2-(1H-tetraazol-1-yl)benzyl]-1-[(9-hydroxy-9H-fluoren-9-yl)carbonyl]-D-prolinamide

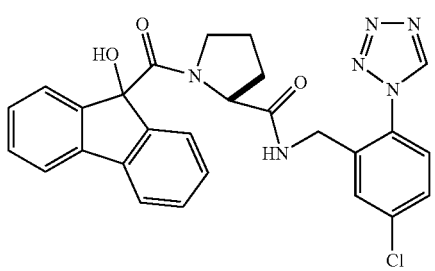

Prepared by procedures similar to that described above in Example 8 from 9-hydroxy-9-fluorenylcarbonyl-L-proline and 1-[5-chloro-2-(1H-tetraazol-1-yl)phenyl]methanamine.

Mass spec.(electrospray) M+1=515.2.

EXAMPLE 17

Preparation of N-[5-chloro-2-(1H-1,2,4-triazol-1-yl)benzyl]-1-[(9-hydroxy-9H-fluoren-9-yl)carbonyl]-L-prolinamide

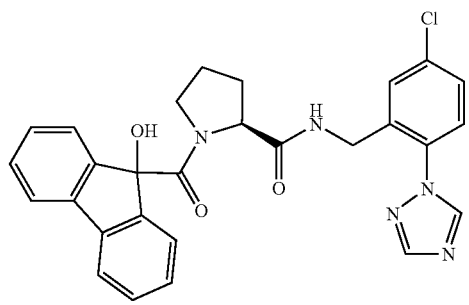

To a stirred solution of 1-[(9-hydroxy-9H-fluoren-9-yl)carbonyl]-L-proline (Example 16, Step B, 0.05 g, 0.16 mmol) in DMF (1 mL) was added 1-[5-chloro-2-(1H-1,2,4-triazol-1-yl)phenyl]methanamine (Example 4, 0.04 g, 0.2 mmol) and BOP reagent (0.09 g, 0.19 mmol) and the pH was adjusted to 8 with N-methylmorpholine. The reaction was complete in one hour, by the absence of starting material on HPLC, and was filtered and purified on a preparative HPLC. Pooled fractions were freeze-dried and lyophilized to yield the solid TFA salt of N-[5-chloro-2-(1H-1,2,4-triazol-1-yl)benzyl]-1-[(9-hydroxy-9H-fluoren-9-yl)carbonyl]-L-prolinamide (0.06 g, HPLC RT=3.17 min, Method A; LCMS m/z=514), $^1$H NMR (400 MHz, CDCl$_3$): δ 8.63 (s,1H), 8.27 (s, 1H), 7.67–7.65 (m, 3H), 7.52–7.44 (m, 1H), 7.42–7.37 (m, 2H), 7.35–7.29 (m, 3H), 7.24–7.22 (m, 1H), 7.16–7.14 (m, 1H), 4.58–4.56 (m, 1H), 4.37–4.29 (s, 2H), 2.35–2.24 (m, 2H), 2.11–1.97 (m, 1H), 1.76–1.59 ppm (m, 2H), 1.48–1.4 (m, 1H).

EXAMPLE 18

Preparation of 1-[(3-chlorophenyl)(hydroxy)pyridin-3-ylacetyl]-N-[2-(1H-tetraazol-1-yl)benzyl]-L-prolinamide

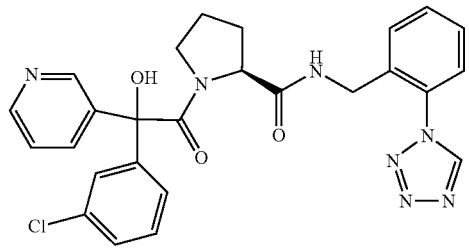

Step A: Ethyl-(3-chlorophenyl)(oxo)acetate

Diethyl oxalate (4.4 g, 30.2 mmol) was dissolved in dry ethyl ether (30 mL) and freshly distilled THF (30 mL) and cooled to −78° C. with stirring, under a nitrogen atmosphere. Then added 3-chlorophenylmagnesium bromide (0.5 M in THF, 72.5 mL, 36.2 mmol) dropwise, via an addition funnel, while keeping the temperature between −75 to −78° C. The addition took approximately 90 minutes. After 3 hours, the reaction was quenched by the dropwise addition of 2N sulfuric acid (50 mL, 91 mmol) at −78° C. and upon completion of the addition, the mixture was allowed to return to room temperature. The mixture was extracted with ethyl ether (3×) and the combined ether extracts were washed with brine (2×), dried over magnesium sulfate, filtered, evaporated in vacuo and vacuum-dried to yield ethyl-(3-chlorophenyl)(oxo)acetate (6.5 g, HPLC RT=3.46 min, Method A; LCMS m/z=213).

Step B: (3-Chlorophenyl)(oxo)acetic acid

To a stirred solution of ethyl-(3-chlorophenyl)(oxo)acetate (6.5 g, 30.5 mmol) in ethyl alcohol (80 mL) was added sodium hydroxide (50% solution, 1.94 mL, 36.6 mmol) and mixing was continued for 24 hours at room temperature. The mixture was then neutralized with concentrated hydrochloric acid, evaporated in vacuo, azeotroped with toluene and dried to yield 3-chlorophenyl)(oxo)acetic acid (7.3 g, Theoretical yield=5.6 g, balance is NaCl; HPLC RT=2.39 min, Method A).

Step C: tert-Butyl 1-[(3-chlorophenyl)(oxo)acetyl]-L-prolinate

To a stirred solution of 3-chlorophenyl)(oxo)acetic acid (30.2 mmol from Step B above) in DMF (55 mL) was added H-Pro-O-tert-butyl ester (6.5 g, 38.1 mmol), HOBt (4.9 g, 36.3 mmol), EDC (8.1 g, 42.3 mmol) and N-methylmorpholine to pH=6.5. The reaction was stirred at room temperature for 24 hours, evaporated in vacuo and partitioned between EtOAc and saturated sodium bicarbonate solution. The layers were separated and the organic layer was washed twice with water, evaporated in vacuo and vacuum dried and purified on silica gel using a 1:3 mixture of EtOAc to hexane as mobile phase. Pure fractions were combined and dried to yield tert-butyl 1-[(3-chlorophenyl)(oxo)acetyl]-L-prolinate (8.8 g, HPLC RT=3.65 min, Method A; LCMS m/z=282, without t-butyl group).

Step D: tert-Butyl 1-[(3-chlorophenyl)(hydroxy)pyridin-3-ylacetyl]-L-prolinate tert-Butyl 1-[(3-chlorophenyl)(oxo)acetyl]-L-prolinate (2.2 g, 6.46 mmol) was dissolved in THF (10 mL) and cooled to −78° C. under a nitrogen atmosphere (Vessel A). In a separate vessel containing 3-bromopyridine (0.68 mL, 7.1 mmol) in ethyl ether (50 mL) cooled to −78° C. was added n-BuLi (2.5M in hexanes, 3.1 mL, 7.7 mmol) and the mixture was stirred for one hour (Vessel B). The contents of Vessel B were added to Vessel A via cannula at −78° C. The temperature was increased to 0° C. and the mixture stirred for 2.5 hours. The mixture was then quenched with saturated ammonium chloride solution (40 mL) and extracted with EtOAc. The EtOAc was evaporated in vacuo, and the residue dried and purified on silica gel using a 1:1 then 2:1 mixture of EtOAc to hexane as mobile phase. Pooled fractions were dried to yield: Nonpolar isomer of tert-butyl 1-[(3-chlorophenyl)(hydroxy)pyridin-3-ylacetyl]-L-prolinate (0.43 g, HPLC RT=3.01 min, Method A; LCMS m/z=417). Polar isomer of ten-butyl 1-[(3-chlorophenyl)(hydroxy)pyridin-3-ylacetyl]-L-prolinate (0.12 g, HPLC RT=2.96 min, Method A; LCMS m/z=417).

Step E: 1-[(3-Chlorophenyl)(hydroxy)pyridin-3-ylacetyl]-L-proline

The nonpolar isomer tert-butyl 1-[(3-chlorophenyl)(hydroxy)pyridin-3-ylacetyl]-L-prolinate (0.087 g, 0.21 mmol) was dissolved in dichloromethane (4 mL) and trifluoroacetic acid (1 mL) and stirred at room temperature for 4 hours. Then the mixture was evaporated in vacuo and vacuum dried to yield the nonpolar isomer of 1-[(3-chlorophenyl)(hydroxy)pyridin-3-ylacetyl]-L-proline (0.04 g, HPLC RT=2.51 min, Method A; LCMS m/z=361).

The polar isomer of tert-butyl 1-[(3-chlorophenyl)(hydroxy)pyridin-3-ylacetyl]-L-prolinate (0.059 g, 0.14 mmol) was dissolved in THF (1 mL) and 6N hydrochloric acid (2 mL) and stirred for 24 hours at room temperature. The mixture was then evaporated in vacuo and vacuum dried to yield the polar isomer of 1-[(3-chlorophenyl)(hydroxy)pyridin-3-ylacetyl]-L-proline (0.051 g, HPLC RT=2.399 min, Method A; LCMS m/z=361).

Step F: 1-[(3-chlorophenyl)(hydroxy)pyridin-3-ylacetyl]-N-[2-(1H-tetraazol-1-yl)benzyl]-L-prolinamide To a stirred solution of the nonpolar isomer of 1-[(3-chlorophenyl)(hydroxy)pyridin-3-ylacetyl]-L-proline (0.04 g, 0.11 mmol) in isopropyl alcohol (1 mL) was added 1-[2-(1H-tetraazol-1-yl)phenyl]methanamine (0.027 g, 0.16 mmol), BOP reagent (0.063 g, 0.14 mmol), and N-methylmorpholine to pH=8. The reaction was followed to completion by HPLC and after 24 hours was evaporated in vacuo and purified on a Gilson Preparative HPLC to yield the TFA salt of the nonpolar isomer of 1-[(3-chlorophenyl)(hydroxy)pyridin-3-ylacetyl]-N-[2-(1H-tetraazol-1-yl)benzyl]-L-prolinamide (0.014 g, HPLC RT=2.71 min, Method A; LCMS m/z=518). $^1$H NMR (400 MHz, CDCl$_3$): δ 9.18 (s, 1H), 8.96 (s, 1H), 8.56 (d, 1H), 8.41–8.39 (d, 1H), 7.77–7.74 (m, 1H), 7.64–7.60 (m, 1H), 7.56 (s, 1H), 7.53 (s 1H), 7.47–7.37 (m, 2H), 7.35 (s, 2H), 7.23 (d, 1H), 4.81–4.48 (m, 1H), 4.23–4.12 (m, 2H), 3.86–3.79 (m, 1H), 3.41–3.29 (m, 1H), 2.15–2.09 (m, 1H), 1.96–1.87 (m, 2H), 1.63–1.55 (m, 1H).

To a stirred solution of the polar isomer of 1-[(3-chlorophenyl)(hydroxy)pyridin-3-ylacetyl]-L-proline (0.051 g, 0.14 mmol) in isopropyl alcohol (1.5 mL) was added 2-(tetrazole-1-yl)-benzylamine (0.025 g, 0.15 mmol), BOP reagent (0.055 g, 0.13 mmol), and N-methylmorpholine to pH=8. The reaction was followed to completion by HPLC and after 24 hours was evaporated in vacuo and purified on a Gilson Preparative HPLC to yield the TFA salt of the polar isomer of 1-[(3-chlorophenyl)(hydroxy)pyridin-3-ylacetyl]-N-[2-(1H-tetraazol-1-yl)benzyl]-L-prolinamide (0.013 g, HPLC RT=2.62 min, Method A; LCMS m/z=518). $^1$H NMR (400 MHz, CDCl$_3$): δ 9.15 (s, 1H), 8.94–8.90 (s, 1H), 8.47–8.44 (d, 1H), 8.42–8.40 (d, 1H), 7.68–7.60 (m, 2H), 7.58–7.51 (m, 2H), 7.49–7.40 (m, 2H), 7.38–7.30 (m, 2H), 7.28 (s, 1H), 4.39–4.28 (m, 1H), 4.27–4.24 (m, 2H), 3.82–3.61 (m, 1H), 3.05–2.90 (m, 1H), 2.03–1.95 (m, 1H), 1.94–1.82 (m, 2H), 1.80–1.70 (m,1H).

EXAMPLE 19

Preparation of 1-[(3-chlorophenyl)(hydroxy)(1-oxidopyridin-3-yl)acetyl]-N-[2-(1H-tetraazol-1-yl)benzyl]-L-prolinamide

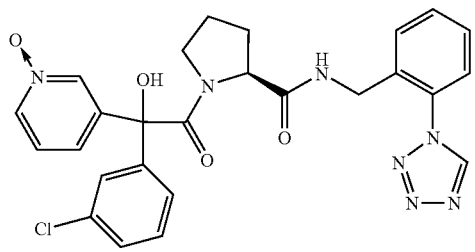

The TFA salt of the polar isomer of 1-[(3-chlorophenyl)(hydroxy)pyridin-3-ylacetyl]-N-[2-(1H-tetraazol-1-yl)benzyl]-L-prolinamide (0.01 g, 0.02 mmol) was partitioned between EtOAc and saturated sodium bicarbonate solution and extracted with EtOAc to retrieve the free base. To a stirred solution of the dried free base of 1-[(3-chlorophenyl)(hydroxy)pyridin-3-ylacetyl]-N-[2-(1H-tetraazol-1-yl)benzyl]-L-prolinamide (0.009 g, 0.017 mmol) in dichloromethane (1 mL), cooled to 0° C., was added 3-chloroperoxybenzoic acid 70% (0.006 g, 0.026 mmol). After 2 hours, the reaction was evaporated in vacuo and purified on a Gilson Preparative HPLC. Pure fractions were combined, freeze dried and lyophilized to yield the solid TFA salt of 1-[(3-chlorophenyl)(hydroxy)(1-oxidopyridin-3-yl)acetyl]-N-[2-(1H-tetraazol-1-yl)benzyl]-L-prolinamide (0.003 g, HPLC RT=2.70 min, Method A; LCMS m/z=534).

EXAMPLE 20

Preparation of 1-[(9-hydroxy-9H-fluoren-9-yl)carbonyl]-N-[2-(4H-1,2,4-triazol-4-yl)benzyl]-L-prolinamide

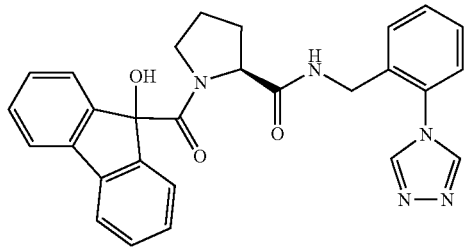

To a stirred solution of 1-[(9-hydroxy-9H-fluoren-9-yl)carbonyl]-L-proline (Example 16, Step B, 0.06 g, 0.19 mmol) in DMF (1 mL) was added 1-[2-(4H-1,2,4triazol-4-yl) phenyl]methanamine (Example 5, Step A, 0.05 g, 0.31 mmol), BOP Reagent (0.11 g, 0.24 mmol) and N-methylmorpholine to pH=8. The mixture was stirred at room temperature under a nitrogen atmosphere for 1 hour, filtered and purified on a Gilson Preparative HPLC to give the solid 1-[(9-hydroxy-9H-fluoren-9-yl)carbonyl]-N-[2-(4H-1,2,4-triazol-4-yl)benzyl]-L-prolinamide (0.065 g, HPLC RT=2.77 min, Method A; LCMS m/z=480). $^1$H NMR (400 MHz, CDCl$_3$): δ 8.75 (s, 2H), 7.67–7.64 (m, 3H), 7.62–7.52 (m, 1H), 7.44–7.37 (m, 2H), 7.35–7.29 (m, 3H), 7.23–719 (m, 1H), 7.15 (s, 1H), 7.04 (d, 1H), 4.55–4.53 (m, 1H), 4.31–4.11 (m, 2H), 2.34–2.26 (m, 1H), 2.24–1.95 (m, 1H), 1.72–1.55 (m, 2H), 1.46–1.43 (m, 1H).

EXAMPLE 21

Preparation of 1-[(9-hydroxy-9H-fluoren-9-yl)carbonyl]-N-[2-(1H-imidazol-1-yl)benzyl]-L-prolinamide

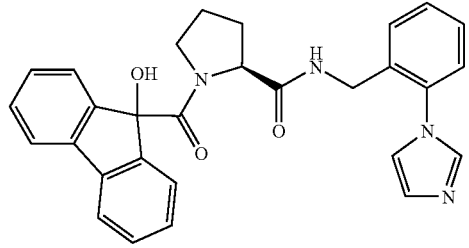

To a stirred solution of 1-[(9-hydroxy-9H-fluoren-9-yl)carbonyl]-L-proline (Example 16, Step B, 0.06 g, 0.19 mmol) in DMF (1 mL) was added 1-[2-(1H-imidazol-1-yl)phenyl]methanamine (Example I-5, 0.05 g, 0.30 mmol), BOP Reagent (0.11 g, 0.24 mmol) and N-methylmorpholine to pH=8. The mixture was stirred at room temperature under a nitrogen atmosphere for 3 hours, filtered and purified on a Gilson Preparative HPLC to afford the solid TFA salt of 1-[(9-hydroxy-9H-fluoren-9-yl)carbonyl]-N-[2-(1H-imidazol-1-yl)benzyl]-L-prolinamide (0.07 g, HPLC RT=2.64 min, Method A; LCMS m/z=479). $^1$H NMR (400 MHz, CDCl$_3$): δ 8.99 (s, 1H), 7.67 (s, 1H), 7.65–7.57 (s, 3H), 7.55 (s, 1H), 7.54–7.51 (m, 1H), 7.44–7.38 (m, 3H), 7.36–7.31 (m, 3H), 7.25–7.21 (m, 1H), 7.16–7.00 (d, 1H), 4.56–4.53 (m, 1H), 4.29–4.13 (m, 2H), 2.34–2.22 (m, 2H), 1.92–1.91 (m, 1H), 1.76–1.64 (m, 1H), 1.62–1.55 (m, 1H), 1.46–1.42 (m, 1H).

EXAMPLE 22

Preparation of 1-[(9-hydroxy-9H-fluoren-9-yl)carbonyl]-N-[2-(1H-imidazol-2-yl)benzyl]-L-prolinamide

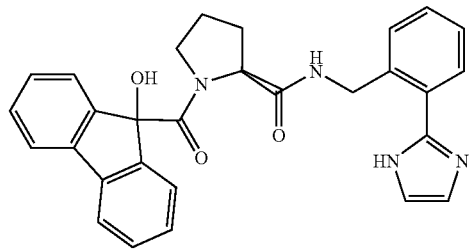

To a stirred solution of 1-[(9-hydroxy-9H-fluoren-9-yl)carbonyl]-L-proline (0.04 g, 0.12 mmol), (Example 16, Step B), in DMF (2 mL) was added 1-[2-(1H-imidazol-2-yl)phenyl]methanamine (Example I-3, 0.032 g, 0.18 mmol), BOP Reagent (0.075 g, 0.17 mmol) and N-methylmorpholine to pH=8. The mixture was stirred at room temperature under a nitrogen atmosphere for 2.5 hours, filtered and purified on a Gilson Preparative HPLC to give the solid TFA Salt of 1-[(9-hydroxy-9H-fluoren-9-yl)carbonyl]-N-[2-(1H-imidazol-2-yl)benzyl]-L-prolinamide (0.032 g, HPLC RT=2.73 min, Method A; LCMS m/z=479). $^1$H NMR (400 MHz, CDCl$_3$): δ 8.98–8.93 (s, 1H), 7.72–7.67 (d, 1H), 7.65–7.62 (d, 2H), 7.47–7.39 (s, 4H), 7.38–7.27 (m, 4H), 7.22–7.17 (m, 1H), 7.16–7.12 (d, 1H), 4.65–4.59 (m, 1H), 3.89–3.80 (s, 2H), 2.33–2.27 (m, 2H), 1.89–1.70 (m, 2H), 1.58–1.39 (m, 2H).

EXAMPLE 23

Preparation of 1-[(9-hydroxy-9H-fluoren-9-yl)carbonyl]-N-(2-pyrazin-2-ylbenzyl)-L-prolinamide

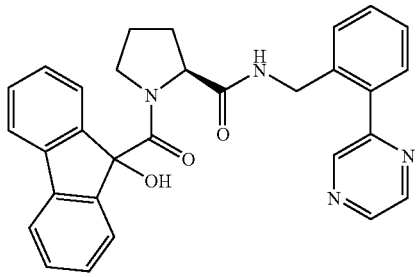

Step A: 2-Pyrazin-2-ylbenzaldehyde

A solution of Pd(PPh$_3$)$_4$ (330 mg, 0.28 mmol) and chloropyrazine (987 µL, 11.0 mmol) in anhydrous DME (60 mL) was stirred for 20 min at room temperature under N$_2$ atmosphere. The resulting red-orange mixture was treated with a solution of Na$_2$CO$_3$ (1.05 mg, 3.30 mmol) in H$_2$O (15 ml), followed by 2-formylbenzene boronic acid (1.50 mg, 9.90 mmol), resulting in a white precipitate. The mixture was heated to reflux for 1.5 h. The DME was then removed in vacuo and the residual suspension was extracted twice with CH$_2$Cl$_2$. The combined organic extracts were dried (anhydrous Na$_2$SO$_4$) and concentrated to give the title compound as a red-orange solid which was dried in vacuo for 16 h and used without further purification. LCMS (M+H): 185.02.

Step B: (2-Pyrazin-2-ylphenyl)methanol

To a stirred suspension of 2-pyrazin-2-ylbenzaldehyde (9.9 mmol from the previous step) in absolute MeOH (100 mL) at 0° C. was added sodium borohydride (420 mg, 11.1 mmol) in portions. The mixture was allowed to warm to room temperature and stirred under N$_2$ atmosphere for 2 h. The solvent was removed in vacuo and the residue was treated with saturated aqueous NH$_4$Cl. The mixture was extracted twice with EtOAc and the combined organic extracts were washed successively with H$_2$O and brine, dried (MgSO$_4$), filtered and concentrated to give a brown oil. Silica gel chromatography (70% EtOAc-hexanes) afforded the title compound as a pale brown oil. $^1$H NMR (400 MHz, CDCl$_3$): δ 8.96 (s, 1 H), 8.65–8.61 (m, 2 H), 7.62–7.46 (m, 4 H), 5.18 (t, J=7.2 Hz, 1 H), 4.49 (d, J=7.2 Hz, 2 H). LCMS (M+H): 186.9.

Step C: 2-[2-(Azidomethyl)phenyl]pyrazine

To a stirred solution of (2-pyrazin-2-ylphenyl)methanol (1.14 g, 6.13 mmol) in anhydrous THF (12.5 mL) at 0° C. was added DPPA (1.59 ml, 7.36 mmol) and DBU (1.01 mL, 6.75 mL). The resulting cloudy yellow mixture was allowed to warm to room temperature, and after 3.5 h was warmed to 80° C. for 3 h. The mixture was then cooled to room temperature and the THF was removed in vacuo. The residue was partitioned between EtOAc and H$_2$O. The layers were separated and the aqueous layer was further extracted with EtOAc. The combined organic extracts were washed successively with a 10% aqueous solution of citric acid, saturated aqueous NaHCO$_3$ and brine. The organic solution was dried (anhydrous Na$_2$SO$_4$), filtered and concentrated to a yellow-brown oil. Silica gel chromatography (40% EtOAc-hexanes) afforded the title compound as a pale yellow oil. $^1$H NMR (400 MHz, CDCl$_3$): δ 8.82 (d, J=1.6 Hz, 1 H), 8.67 (dd, J=1.6, 2.4 Hz, 1 H), 8.59 (d, J=2.4 Hz, 1 H), 7.55–7.48 (m, 4 H), 4.60 (s, 2 H). LCMS (M+H): 212.1.

Step D: 1-(2-Pyrazin-2-ylphenyl)methanamine hydrochloride

To a stirred solution of 2-[2-(azidomethyl)phenyl]pyrazine (1.01 g, 4.79 mmol) in THF (92 mL) at room temperature was added triphenylphosphine (2.51 g, 9.57 mmol). The solution was stirred for 10 min and was then treated with H$_2$O (1.8 mL). The clear solution was heated to 60° C. and stirred at this temperature for 16 h. The solvent was removed in vacuo. The residue was taken up in EtOAc (20 mL) and treated with cold, saturated HCl-EtOAc solution until no more precipitation was observed. The solid was collected by filtration, washed with EtOAc and Et$_2$O and dried in vacuo for 16 h to yield the title compound as a light yellow solid. $^1$H NMR (500 MHz, CD$_3$OD): δ 9.11 (d, J=1.5 Hz, 1 H), 8.88 (dd, J=1.5, 2.5 Hz, 1 H), 8.75 (d, J=3.0 Hz, 1 H), 7.85 (dd, J=1.5, 7.5 Hz, 1 H), 7.71–7.62 (m, 3 H), 4.17 (s, 2 H). LCMS (M+H): 186.0.

Step E: 1-[(9-Hydroxy-9H-fluoren-9-yl)carbonyl]-N-(2-pyrazin-2-ylbenzyl)-L-prolinamide A mixture of 1-(2-pyrazin-2-ylphenyl)methanamine hydrochloride (59 mg, 0.22 mmol), 1-[(9-hydroxy-9H-fluoren-9-yl)carbonyl]-L-proline (Example 16, Step B, 66 mg, 0.20 mmol), EDC (59 mg, 0.31 mmol), HOAt (14 mg, 0.10 mmol) and Et$_3$N (61 µL, 0.44 mmol) in DMF (1.1 mL) was stirred at room temperature for 5 h. H$_2$O was added dropwise to the mixture, resulting in precipitation. The pale yellow solid was collected by filtration, washed with H$_2$O and dried in vacuo. Silica gel chromatography (70% EtOAc-hexanes-100% EtOAc) afforded a white film which was dissolved in EtOAc and treated with a 1 M solution of HCl in Et$_2$O. The resulting precipitate was collected by filtration, washed with Et$_2$O and dried in vacuo to afford the title compound as a light yellow solid. $^1$H NMR (500 MHz, CD$_3$OD): δ 8.96 (s, 1 H), 8.85 (s, 1 H), 8.70 (m, 1H), 7.78–7.75 (m, 2 H), 7.65–7.23 (m, 10 H), 4.55 (d, J=15.0 Hz, 1 H), 4.50 (d, J=15.0 Hz, 1 H), 4.40–4.38 (m, 1 H), 2.37 (br m, 2 H 1.87–1.83 (m, 1 H), 1.60–1.52 (m, 2 H), 1.41–1.38 (m, 1 H). HRMS (APCI, M+H): 491.2076 (found); 491.2078 (calculated).

EXAMPLE 24

Preparation of ethyl({(1R)-2-[(2S-2-({[5-chloro-2-(1H-1,2,4-triazol-1-yl)benzyl]amino}carbonyl)azetidin-1-yl]-1-cyclohexyl-2-oxoethyl)amino)acetate

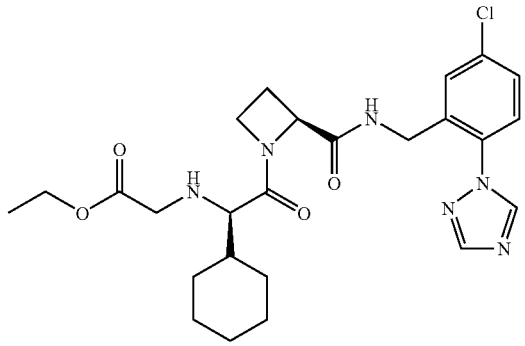

Step A: tert-Butyl(1R)-2-[(2S-2-({[5-chloro-2-(1H-1,2,4-triazol-1-yl)benzyl]amino}carbonyl)azetidin-1-yl]-1-cyclohexyl-2-oxoethylcarbamate A mixture of (2S-1-1{(2R)-2[(tert-butoxycarbonyl)amino]-2cyclohexylethanoyl}azetidine-2-carboxylic acid (preparation described in patent publication WO 9723499, 100 mg, 0.29 mmol), 1-[5-chloro-2-(1H-1,2,4-triazol-1-yl)

phenyl]methanamine (61 mg, 0.29 mmol), EDC (56 mg, 0.29 mmol), HOBt (40 mg, 0.029 mmol) and NMM (97 μL, 0.88 mmol) in DMF (2.0 mL) was stirred at ambient temperature for 16 h. The reaction mixture was diluted with 15 mL of EtOAc and washed with sat. NaHCO$_3$, water and brine. The organic layer was dried (MgSO4) filtered and concentrated to dryness. The residue was purified by silica gel chromatography(100% EtOAc to 15% MeOH/EtOAc) to afford 148 mg of the title compound. LCMS (M+H): 531.2

Step B: (2S-1-[(2R)-2-amino-2-cyclohexylethanoyl]-N-(5-chloro-2-(1H-1,2,4-triazol-1-yl)benzyl]azetidine-2-carboxamide hydrochloride HCl gas was bubbled through a cold (0° C.) solution of tert-butyl(1R)-2-[(2S-2-({[5-chloro-2-(1H-1,2,4-triazol-1-yl)benzyl]amino}carbonyl)azetidin-1-yl]-1-cyclohexyl-2-oxoethylcarbamate (140 mg, 0.26 mmol from the previous step) in EtOAc (10 mL) for 3 min. After stirring for 2 hr at room temperature the reaction mixture was concentrated to a solid. LCMS (M+H): 431.2

Step C: Ethyl({(1R)-2-[(2S-2-({[5-chloro-2-(1H-1,2,4-triazol-1-yl)benzyl]amino}carbonyl)azetidin-1-yl]-1-cyclohexyl-2-oxoethyl)amino)acetate A solution of (2S-1-[(2R)-2-amino-2-cyclohexylethanoyl]-N-(5-chloro-2-(1H-1,2,4-triazol-1-yl)benzyl]azetidine-2-carboxamide hydrochloride (50 mg, 0.11 mmol), ethyl bromoacetate (12 μL, 0.11 mmol) and K$_2$CO$_3$ (44 mg, 0.32 mmol) in 1:1 THF/DMF was stirred for 16 h at room temperature. An additional 0.02 equivalents of ethyl bromoacetate and K$_2$CO$_3$ were added and the mixture stirred for an additional 6 h to drive the reaction to completion. Silica gel chromatography (100% EtOAc to 10% MeOH/EtOAc) afforded the title compound. LCMS (M+H): 517.2. $^1$H NMR (400 MHz, CDCl$_3$): δ 8.42 (m, 2H), 8.13 (s, 1H), 7.58 (s, 1H), 7.36 (m, 1H), 7.2 (m, 1H), 4.87 (m, 1H), 4.35 (m, 2H), 4.13 (m, 4H), 3.28 (m, 2H), 2.87 (m, 1H), 2.61–2.51 (m, 2H), 2.05–1.97 (m, 1H), 1.75–1.55 (m, 6H), 1.28–1.01 (m, 7H).

EXAMPLE 25

Preparation of ({(1R)-2-[(2S)-2-({[5-chloro-2-(1H-1,2,4-triazol-1-yl)benzyl]amino}carbonyl)azetidin-1-yl]-1-cyclohexyl-2-oxoethyl}amino)acetic acid

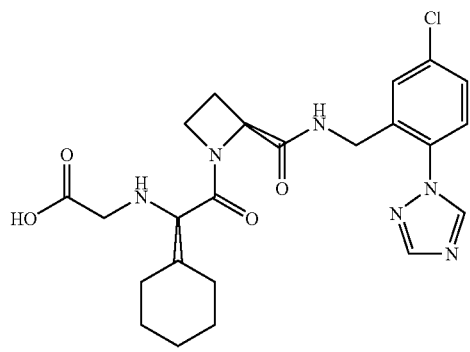

Step A: tert-Butyl({(1R)-2-[(2S)-2-([5-chloro-2-(1H-1,2,4-triazol-1-yl)benzyl]amino}carbonyl)azetidin-1-yl]-1-cyclohexyl-2-oxoethyl}amino)acetate A mixture of (2S-1-[(2R)-2-amino-2-cyclohexylethanoyl]-N-(5-chloro-2-(1H-1,2,4-triazol-1benzyl]azetidine-2-carboxamide hydrochloride (Example 24, Step B, 25 mg, 0.05 mmol), t-butyl bromoacetate (9 μL, 0.06 mmol) and K$_2$CO$_3$ (37 mg, 0.27 mmol) in THF was stirred for 16 h at room temperature. An additional 0.02 equivalents each of t-butyl bromoacetate and K$_2$CO$_3$ were added and the mixture stirred for 3 h to drive the reaction to completion. Silica gel chromatography (100% EtOAc to 15% MeOH/EtOAc) afforded the title compound. LCMS (M+H): 545.3

Step B: ({(1R)-2-[(2S)-2-({[5-chloro-2-(1H-1,2,4-triazol-1-yl)benzyl]amino}carbonyl)azetidin-1-yl]-1-cyclohexyl-2-oxoethyl}amino)acetic acid TFA (5 mL) was added to a solution of tert-butyl({(1R)-2-[(2S)-2-({[5-chloro-2-(1H-1,2,4-triazol-1-yl)benzyl]amino}carbonyl)azetidin-1-yl]-1-cyclohexyl-2-oxoethyl}amino)acetate (22 mg, 0.04 mmol) in CH2Cl2 (5 mL) at 0° C. After stirring for 16 h the reaction mixture was concentrated. The title compound was isolated by reverse phase HPLC. LCMS (M+H): 489.3. $^1$H NMR (400 MHz, CD$_3$OD): δ 8.80 (s, 1H), 8.22 (s, 1H), 7.67 s, 1H), 7.50 (m, 2H), 4.79 (m, 1H), 4.45–4.20 (m, 5H), 3.91 (m, 3H), 2.61 (m, 1H), 2.21 (m, 1H), 1.87–1.72 (m, 5H), 1.37–1.17 (m, 5H).

EXAMPLE 26

Preparation of 2-methylleucyl-N-[5-chloro-2-(1H-tetraazol-1-yl)benzyl]-L-prolinamide

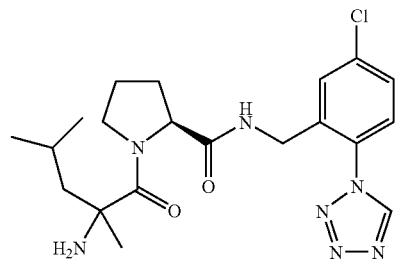

Step A: 2-tert-Butyloxycarbonylamino-2,4-dimethylpentanoic acid

To a stirred solution of D,L-alpha-methyl-leucine (1.0 g, 6.9 mmol) in dioxane (15 mL) was added aqueous NaOH (2.8 mL of a 2.5 molar solution, 7.0 mmol) and di-tert-butyl dicarbonate (1.6 g, 7.3 mmol). The mixture was stirred at ambient temperature. Two more portions of di-tert-butyl dicarbonate (0.8 g, 3.7 mmol each portion) were added at 24 h intervals. The resulting mixture was stirred at ambient temperature for 24 h after the final addition of di-tert-butyl dicarbonate. The solvent was removed in vacuo and the residue was partitioned between water (25 mL) and ether (20 mL). The aqueous layer was separated and stirred with CH$_2$Cl$_2$ (20 mL) while solid citric acid (2 g, 10 mmol) was added. The CH$_2$Cl$_2$ layer was separated and the aqueous layer was extracted with another portion of CH$_2$Cl$_2$ (20 mL). The combined CH$_2$Cl$_2$ layers were dried (MgSO$_4$), filtered, and the solvent was removed in vacuo to give the title compound as a waxy solid.

Step B : N-[5-chloro-2-(1H-tetraazol-1-yl)benzyl]-L-prolinamide

A mixture of 1-(tert-butoxycarbonyl)-L-proline (1.03 g, 4.77 mmol), 1-[5-chloro-2-(1H-tetraazol-1-yl)phenyl]methanamine (Example 2, 1.00 g, 4.77 mmol, 1.0 equiv), EDC (1.37 g, 7.16 mmol, 1.5 equiv) and HOAt (325 mg, 2.39 mmol, 0.5 equiv) in DMF (5 mL) was brought to pH 8 by dropwise addition of Hünig's Base and stirred at room temperature for 18 h. The reaction was diluted with water and extracted into EtOAc three times. The combined organic layers were dried (anhydrous Na$_2$SO$_4$) and concentrated. Silica gel chromatography (70% EtOAc-hexanes to EtOAc) afforded a white solid which was taken up in 4.0M HCl-ether (2 mL). Methanol was added dropwise to aid in solubility, and gaseous HCl was bubbled through the solution for 30 s. The solution was stirred for 1 h. The solvent was removed in vacuo and the residue was azeotroped twice with ether to afford the title compound as a hygroscopic yellow solid. $^1$H NMR (400 MHz, CD$_3$OD): δ 9.59 (s, 1 H), 8.83 (br s, 1 H), 7.69 (d, J=2.0 Hz, 1 H), 7.59 (dd, J=2.0, 8.4 Hz, 1 H), 7.52 (d, J=8.4 Hz, 1 H), 4.32 (m, 2 H), 4.27–4.24 (m, 1 H), 3.40–3.32 (m, 2 H), 2.44–2.36 (m, 1 H), 2.09–1.89 (m, 3 H). LCMS (M+H): 307.1.

Step C: N-(tert-butoxycarbonyl)-2-methylleucyl-N-[5-chloro-2-(1H-tetraazol-1-yl)benzyl]-L-prolinamide A mixture of 2-tert-butyloxycarbonylamino-2,4-dimethylpentanoic acid (120 mg, 0.49 mmol), N-[5-chloro-2-(1H-tetraazol-1-yl)benzyl]-L-prolinamide (150 mg, 0.49 mmol, 1.0 equiv), EDC (141 mg, 0.73 mmol, 1.5 equiv) and HOAt (33 mg, 0.24 mmol, 0.5 equiv) in DMF (1 ml) was brought to pH 8 by dropwise addition of Hünig's Base and stirred at room temperature for 18 h. The solvent was removed in vacuo, and the resulting oil was purified by silica gel chromatography (50% EtOAc-hexanes to 70% EtOAc-hexanes to EtOAc) to afford the two separate diastereomers as white solids. Diastereomer A (less polar): $^1$H NMR (300 MHz, CDCl$_3$): δ 9.32 (s, 1 H), 8.10 (t, J=5.4 Hz, 1 H), 7.72 (d, J=2.1 Hz, 1 H), 7.40 (dd, J=2.1, 8.1 Hz, 1 H), 7.27 (d, J=8.1 Hz, 1 H), 5.03 (s, 1 H), 4.55–4.50 (m, 1 H), 4.23 (dd, J=6.3, 15.3 Hz, 1 H), 4.01 (dd, J=5.1, 15.3 Hz, 1 H), 3.84–3.79 (m, 1 H), 3.55–3.52 (m, 1 H), 2.22–2.12 (m, 1 H), 1.95–1.68 (m, 5 H), 1.59 (s, 3 H), 1.51–1.45 (m, 1 H), 1.34 (s, 9 H), 0.98 (d, J=6.6 Hz, 3 H), 0.85 (d, J=6.3 Hz, 3 H). Diastereomer B (more polar): $^1$H NMR (300 MHz, CDCl$_3$): δ 9.29 (s, 1 H), 8.11–8.08 (m, 1 H), 7.70 (d, J=2.1 Hz, 1 H), 7.39 (dd, J=2.1, 8.4 Hz, 1 H), 7.26 (d, J=8.4 Hz, 1 H), 5.21 (s, 1 H), 4.59–4.54 (m, 1 H), 4.25 (dd, J=6.3, 15.3 Hz, 1 H), 4.00 (dd, J=4.8, 15.3 Hz, 1 H), 3.85–3.79 (m, 1 H), 3.53–3.49 (m, 1 H), 2.24–2.22 (m, 1 H), 1.97–1.83 (m, 5 H), 1.66–1.60 (m, 1 H), 1.39 (s, 3 H), 1.36 (s, 9 H), 0.97 (d, J=6.3 Hz, 3 H), 0.91 (d, J=6.6Hz, 3 H). Diastereomeric mixture: LCMS (M+H): 534.0.

Step D: 2-Methylleucyl-N-[5-chloro-2-(1H-tetraazol-1-yl)benzyl]-L-prolinamide

Each diastereomer of N-(tert-butoxycarbonyl)-2-methylleucyl-N-[5-chloro-2(1H-tetraazol-1-yl)benzyl]-L-prolinamide (A: 86 mg, 0.161 mmol; B: 84 mg, 0.158 mmol) was dissolved in a 2:1 solution of CH$_2$Cl$_2$/TFA (3 mL) and stirred for 1 h. Both reactions were then concentrated to oils. Purification by reverse phase chromatography [95:5 water (+0.1% TFA)/CH$_3$CN (+0.1% TFA) to 5:95 water (+0.1% TFA)/CH$_3$CN (+0.1% TFA)] afforded each diastereomer as a clear oil. Diastereomer A: $^1$H NMR (300 MHz, CDCl$_3$): δ 9.32 (s, 1 H), 8.08 (br s, 2 H), 7.78 (t, J=5.1 Hz, 1 H), 7.64 (d, J=2.4Hz, 1 H), 7.44 (dd, J=2.1, 8.7 Hz, 1 H), 7.29 (d, J=8.7 Hz, 1 H), 4.44–4.41 (m, 1 H), 4.23 (m, 2 H), 3.67–3.63 (m, 2 H), 2.28–2.24 (m, 1 H), 2.08–1.85 (m, 5 H), 1.78–1.71 (m, 1 H), 1.68 (s, 3 H), 0.86 (d, J=6.3 Hz, 3 H), 0.78 (d, J=6.6 Hz, 3 H). LCMS (M+H): 434.0. Diastereomer B: $^1$H NMR (300 MHz, CDCl$_3$): δ 9.17 (s, 1 H), 8.30 (br s, 2 H), 8.08–8.04 (m, 1 H), 7.55 (d, J=2.1 Hz, 1 H), 7.44 (dd, J=2.1, 8.7 Hz, 1 H), 7.30 (d, J=8.7 Hz, 1 H), 4.49–4.45 (m, 1 H), 4.26–4.21 (m, 2 H), 3.77–3.66 (m, 2 H), 2.16–1.80 (m, 6 H), 1.77 (s, 3 H), 1.72–1.66 (m, 1 H), 0.92 (d, J=6.6 Hz, 3 H), 0.79 (d, J=6.3 Hz, 3 H). LCMS (M+H): 434.0.

EXAMPLE 27

Preparation of 3-methyl-D-valyl-N-[5-chloro-2-(1H-1,2,4-triazol-1-yl)benzyl]-L-prolinamide

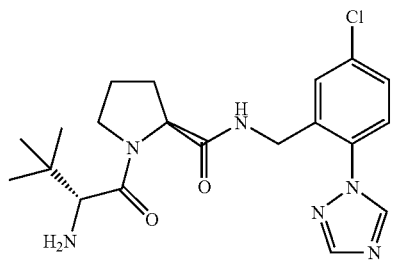

Step A: N-[5-chloro-2-(1H-1,2,4-triazol-1-yl)benzyl]-[(9H-fluoren-9-ylmethoxy)carbonyl]-L-prolinamide A mixture of [(9H-fluoren-9-ylmethoxy)carbonyl]-L-proline (3.23 g, 9.59 mmol), 1-[5-chloro-2-(1H-1,2,4-triazol-1-yl)phenyl]methanamine (Example 4, 2.00 g, 9.59 mmol, 1.0 equiv), EDC (2.76 g, 14.38 mmol, 1.5 equiv) and HOAt (652 mg, 4.79 mmol, 0.5 equiv) in DMF (5 mL) was brought to pH 6 by dropwise addition of Hünig's Base and stirred at room temperature for 18 h. The reaction was diluted with water and extracted into EtOAc three times. The combined organic layers were dried (anhydrous Na$_2$SO$_4$) and concentrated. The resulting oil was suspended and rigorously stirred in water to afford the title compound as white solid upon filtration. $^1$H NMR (400 MHz, CD$_3$OD): δ 8.77 (m, 1 H), 8.24–8.22 (m, 1 H), 7.81–7.75 (m, 2 H), 7.66–7.62 (m, 2 H), 7.54–7.50 (m, 1 H), 7.45–7.31 (m, 5 H), 7.25–7.19 (m, 1 H), 4.43–4.36 (m, 2 H), 4.30–4.20 (m, 3 H), 4.05–4.02 (m, 1 H), 3.55–3.40 (m, 2 H), 2.28–2.18 (m, 1 H), 1.91–1.88 (m, 3 H). LCMS (M+H): 528.0.

Step B: N-[5-chloro-2-(1H-1,2,4-triazol-1-yl)benzyl]-L-prolinamide

A solution of N-[5-chloro-2-(1H-1,2,4-triazol-1-yl)benzyl]-[(9H-fluoren-9-ylmethoxy)carbonyl]-L-prolinamide (5.06 g, 9.59 mmol) and piperidine (82 mg, 9.59 mmol, 1 equiv) in DMF (20 mL) was stirred for 3 h at room temperature then concentrated in vacuo. Silica gel chromatography (EtOAc to 8:1:1 EtOAc/MeOH/NH$_4$OH) afforded a sticky, yellow, solid which was dissolved in EtOAc and treated with gaseous HCl for 1 h at 0° C. Solvent was removed in vacuo, and the remaining residue was suspended in ether with vigorous stirring. The resulting precipitate was filtered and washed with ether to afford the title compound as an off-white, hygroscopic powder. $^1$H NMR (400 MHz, CD$_3$OD): δ 9.79 (s, 1 H), 8.95 (s, 1 H), 7.70 (d, J=1.6 Hz, 1 H), 7.61–7.60 (m, 2 H), 4.44–4.41 (m, 2 H), 4.30 (apparent t, J=7.6 Hz, 1 H), 3.39–3.31 (m, 2 H), 2.46–2.40 (m, 1 H), 2.18–1.92 (m, 3 H). LCMS (M+H): 306.0.

Step C: 3-Methyl-D-valyl-N-[5-chloro-2-(1H-1,2,4-triazol-1-yl)benzyl]-L-prolinamide A mixture of N-(tert-butoxycarbonyl)-3-methyl-D-valine (53 mg, 0.23 mmol), N-[5-chloro-2-(1H-1,2,4-triazol-1-yl)benzyl]-L-prolinamide (87 mg, 0.23 mmol, 1.0 equiv), EDC (66 mg, 0.34 mmol, 1.5 equiv), HOAt (16 mg, 0.11 mmol, 0.5 equiv) in DMF (1 mL) was brought to pH 6 by addition of Hünig's base and stirred at room temperature for 18 h. The solvent was removed in vacuo, and the resulting residue was dissolved in 2:1 $CH_2Cl_2$/TFA (3 mL) and stirred for 1 h. Solvent was again removed in vacuo, and purification by reverse phase chromatography [95:5 water (+0.1% TFA)/$CH_3CN$ (+0.1% TFA) to 50:50 water (+0.1% TFA)/$CH_3CN$ (+0.1% TFA)] afforded the title compound as a clear oil. $^1H$ NMR (400 MHz, $CDCl_3$): δ 8.93 (s, 1 H), 8.29 (s, 1 H), 8.00 (br s, 1 H), 7.55 (d, J=2.0 Hz, 1 H), 7.39 (dd, J=2.0, 8.4 Hz, 1 H), 7.25 (d, J=8.4 Hz, 1 H), 7.01 (br s, 2 H), 4.47–4.45 (m, 1 H), 4.35–4.30 (m, 2 H), 4.15 (dd, J=5.2, 15.2 Hz, 1 H), 3.80–3.71 (m, 1 H), 3.58–3.52 (m, 1 H), 2.15–2.12 (m, 2 H), 2.01–1.98 (m, 2 H), 1.10 (s, 9 H). HRMS (APCI) M+H: calculated for $(C_{20}H_{27}N_6O_2Cl)^+$ 419.1957, found 419.1935.

EXAMPLE 28

Preparation of 3-methyl-D-valyl-N-[5-chloro-2-(1H-tetraazol-1-yl)benzyl]-L-prolinamide

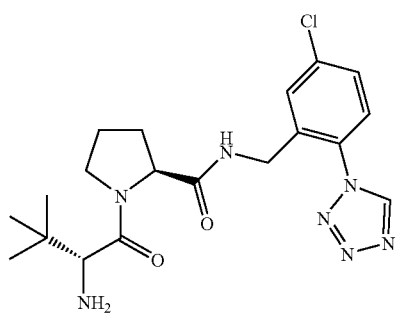

The title compound was prepared from N-(tert-butoxycarbonyl)-3-methyl-D-valine (53 mg, 0.23 mmol), N-[5-chloro-2-(1H-tetraazol-1-yl)benzyl]-L-prolinamide (Example 26, Step B, 87 mg, 0.23 mmol, 1.0 equiv), EDC (66 mg, 0.34 mmol, 1.5 equiv) and HOAt (16 mg, 0.11 mmol, 0.5 equiv) in DMF (1 mL) followed by deprotection in TFA-$CH_2Cl_2$ essentially according to the procedure described in Example 26, Step C. Purification by reverse phase chromatography [95:5 water (+0.1% TFA)/$CH_3CN$ (+0.1% TFA) to 50:50 water (+0.1% TFA)/$CH_3CN$ (+0.1% TFA)] followed by lyophilization of the fractions afforded the title compound as a white powder. $^1H$ NMR (300 MHz, $CDCl_3$): δ 9.22 (s, 1 H), 8.32–8.29 (m, 3 H), 7.85 (d, J=1.8 Hz, 1 H), 7.43 (dd, J=2.1, 8.4 Hz, 1 H), 7.15 (d, J=8.4 Hz, 1 H), 4.45 (app d, J=8.1 Hz, 1 H), 4.35–4.27 (m, 2 H), 3.95–3.79 (m, 2 H), 3.62–3.56 (m, 1 H), 2.31–2.25 (m, 1 H), 2.10–1.87 (m, 3 H), 1.18 (s, 9 H). HRMS (APCI) M+H: calculated for $(C_{19}H_{26}N_7O_2Cl)^+$ 420.1910, found 420.1915.

EXAMPLE 29

Preparation of 4-methyl-D-leucyl-N-[5-chloro-2-(1H-1,2,4-triazol-1-yl)benzyl]-L-prolinamide

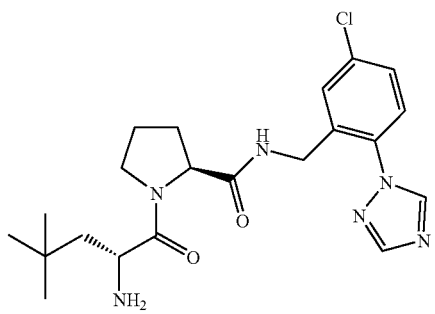

The title compound was prepared from N-(tert-butoxycarbonyl)-4-methyl-D-leucine (32 mg, 0.13 mmol), N-[5-chloro-2-(1H-1,2,4-triazol-1-yl)benzyl]-L-prolinamide (Example 27, Step B, 50 mg, 0.21 mmol, 1.0 equiv), EDC (38 mg, 0.20 mmol, 1.5 equiv) and HOAt (9 mg, 0.07 mmol, 0.5 equiv) in DMF (1 mL) followed by deprotection in TFA-$CH_2Cl_2$ essentially according to the procedure described in Example 27, Step C. Purification by reverse phase chromatography [95:5 water (+0.1% TFA)/$CH_3CN$ (+0.1% TFA) to 50:50 water (+0.1% TFA)/$CH_3CN$ (+0.1% TFA)] followed by lyophilization of the fractions afforded the title compound as a white powder. $^1H$ NMR (400 MHz, $CDCl_3$): δ 8.81 (s, 1 H), 8.35 (br s, 2 H), 8.23 (s, 1 H), 8.09 (t, J=5.6Hz, 1 H), 7.50 (d, J=2.0 Hz, 1 H), 7.35 (dd, J=2.0, 8.4 Hz, 1 H), 7.24 (d, J=8.4 Hz, 1 H), 4.41–4.38 (m, 1 H), 4.29 (dd, J=5.6, 15.6 Hz, 1 H), 4.20–4.12 (m, 2 H), 3.87–3.83 (m, 1 H), 3.50–3.45 (m, 1 H), 2.12–2.02 (m, 3 H), 1.85–1.72 (m, 3 H), 0.96 (s, 9 H). HRMS (APCI) M+H: calculated for $(C_{21}H_{29}N_6O_2Cl)^+$ 433.2113, found 433.2104.

EXAMPLE 30

Preparation of 4-methyl-D-leucyl-N-[5-chloro-2-(1H-tetraazol-1-yl)benzyl]-L-prolinamide

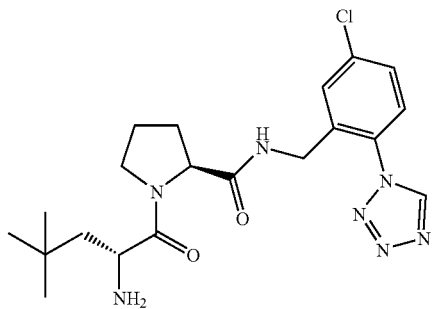

The title compound was prepared from N-(tert-butoxycarbonyl)-4-methyl-D-leucine (32 mg, 0.13 mmol), N-[5-chloro-2-(1H-1,2,4-tetraazol-1-yl)benzyl]-L-prolinamide (Example 26, Step B, 50 mg, 0.21 mmol, 1.0 equiv), EDC (38 mg, 0.20 mmol, 1.5 equiv) and HOAt (9 mg, 0.07 mmol, 0.5 equiv) in DMF (1 mL) followed by deprotection in TFA-$CH_2Cl_2$ essentially according to the procedure described in Example 27, Step C. Purification by reverse phase chromatography [95:5 water (+0.1% TFA)/CH$_3$CN (+0.1% TFA) to 50:50 water (+0.1% TFA)/CH$_3$CN (+0.1% TFA)] followed by lyophilization of the fractions afforded the title compound as a white powder. $^1$H NMR (400 MHz, CDCl$_3$): δ 9.18 (s, 1 H), 8.45 (br s, 2 H), 8.00 (t, J=5.2 Hz, 1 H), 7.73 (d, J=2.0 Hz, 1 H), 7.41 (dd, J=2.0, 8.4 Hz, 1 H), 7.19 (d, J=8.4 Hz, 1 H), 4.41–4.34 (m, 2 H), 4.25 (dd, J=4.8, 14.8 Hz, 1 H), 4.00–3.94 (m, 1 H), 3.89–3.85 (m, 1 H), 3.53–3.46 (m, 1 H), 2.25–2.22 (m, 1 H), 2.09–1.85 (m, 5 H), 1.00 (s, 9 H). HRMS (APCI) M+H: calculated for $(C^{20}H_{28}N_7O_2Cl)^+$ 434.2066, found 434.2065.

EXAMPLE 31

Preparation of 3-cyclopropyl-D-alanyl-N-[5-chloro-2-(1H-1,2,3-triazol-1-yl)benzyl]-L-prolinamide

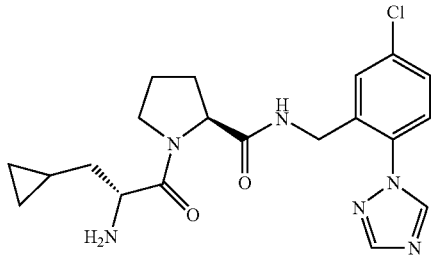

Step A: (2R)-2-[(tert-Butoxycarbonyl)amino]pent-4-enoic acid.

To a cold (0° C.) stirred solution of (2R)-2-aminopent-4-enoic acid (3.7 g, 32.1 mmol) in 1M NaOH (34 mL, 34 mmol) was added dropwise a solution of BOC anhydride (7.72 g, 35.4 mmol) in dioxane (11 mL). Shortly after the start of the addition, the cold bath was removed. The progress of the reaction was monitored by removing aliquots, concentrating at reduced pressure and analyzing by NMR. After 4 h, additional BOC anhydride (770 mg, 3.54 mmol) and 1M NaOH (3.2 mL, 3.2 mmol) was added and stirring continued for 2.5 h. The dioxane was removed at reduced pressure, the residue cooled by the addition of ice, and acidified by the addition of 2M HCl (25 mL). The resulting mixture was extracted with two portions of EtOAc and the combined organic extracts washed with water, brine, dried over Na$_2$SO$_4$ and concentrated at reduced pressure to give the title compound as slightly colored oil (4.27 g): $^1$H NMR (300 MHz, CDCl$_3$) δ 9.15 (br s, 1H), 5.65–5.85 (m, 1H), 5.10–5.20 (m, 2H), 5.06 (d, J=8.1 Hz, 2H), 4.36–4.47 (m, 1H ), 2.40–2.68 (m, 2H), 1.45 (s, 9H).

Step B: Methyl N-(tert-butoxycarbonyl)-3-cyclopropyl-D-alaninate

To a stirred solution of (2R)-2-[(tert-butoxycarbonyl)amino]pent-4-enoic acid (2.15 g, 10.0 mmol) in CH$_2$Cl$_2$ (20 mL) and MeOH (1.5 mL) was added a 2.0 M solution of trimethylsilyldiazomethane in hexane (10 mL) dropwise. After the yellow color persisted and gas evolution ceased, the solution was stirred for 15 min, and then quenched with two drops of HOAc. The reaction mixture was washed with sat. NaHCO$_3$, the aqueous layer extracted with CH$_2$Cl$_2$, the combined organic layers dried over Na$_2$SO$_4$, treated with activated carbon and concentrated at reduced pressure to give 2.2 g of methyl (2R)-2-[(tert-butoxycarbonyl)amino]pent-4-enoate as a yellow oil. This material was dissolved in 20 mL ether, and treated with a solution of diazomethane (prepared by the portionwise treatment of a stirred mixture of 35 mL ether and 10 mL 25% KOH at 0° C. with 3.32 g (22.5 mmol) 1-methyl-3-nitro-1-nitrosoguanidine). The resulting cold (0° C.) stirred solution was treated with a very small portion of Pd(OAc)$_2$ which caused vigorous gas evolution. The cold bath was removed, and stirring continued for 1 h. The reaction mixture was filtered through a 1 cm pad of SiO$_2$ and eluted with ether. The filtrate was concentrated to give a yellow oil that was chromatographed on a 110 g Redi-Sep column using a 0–40% EtOAc-hexane gradient over 40 min, 40 mL/min. The pure fractions were combined and concentrated at reduced pressure to give 1.0 g of the title compound as a colorless oil: $^1$H NMR (300 MHz, CDCl$_3$): δ 5.10–5.20 (br d, J=6.1 Hz, 1H), 4.34–4.43 (m, 1H), 3.74 (s, 3H), 1.66 (t, J=6.5 Hz, 2H), 1.45 (s, 9H), 0.65–0.75 (m, 1H), 0.4–0.55 (m, 2H), 0.01–0.14 (m, 2H).

Step C: N-(tert-Butoxycarbonyl)-3-cyclopropyl-D-alanine

To a stirred solution of methyl N-(tert-butoxycarbonyl)-3-cyclopropyl-D-alaninate (1.0 g, 4.1 mmol) in MeOH (25 mL) at 0° C. was added 1M NaOH (5.0 mL, 5.0 mmol) dropwise. After 1 h, the cold bath was removed, and the reaction followed by HPLC. After 5.5 h, the methanol was removed at reduced pressure, and the residue diluted with 15 mL water and washed with ether. The aqueous layer was acidified with cold 2M HCl and extracted with three portions of EtOAc. The combined organic layers were washed with water, brine, dried over Na$_2$SO$_4$ and concentrated at reduced pressure to give the title compound as a colorless oil (929 mg): $^1$H NMR (300 MHz, CDCl$_3$): δ 5.10–5.22 (br d, J=6.1 Hz, 1H), 4.35–4.46 (m, 1H), 1.72 (t, J=6.2 Hz, 2H), 1.39 (s, 9H), 0.70–0.85 (m, 1H), 0.42–0.60 (m, 2H), 0.03–0.21 (m, 2H).

Step D: N-(tert-butoxycarbonyl)-3-cyclopropyl-D-alanyl-N-[5-chloro-2-(1H-1,2,4-triazol-1-yl)benzyl]-L-prolinamide To a stirred solution of N-[5-chloro-2-(1H1,2,4-triazol-1-yl)benzyl]-L-prolinamide (Example 27, Step B, 0.046 g, 0.121 mmol), N-(tert-butoxycarbonyl)-3-cyclopropyl-D-alanine (30 mg, 0.121 mmol), and HOBt hydrate (20 mg, 0.145 mmol) in DMF (3 mL) was added EDC (0.028 g, 0.145 mmol). Diisopropylethylamine (0.083 mL, 0.484 mmol) was added and the mixture was stirred at ambient temperature for 18 hours, at which time HPLC analysis indicated complete consumption of the proline starting material. The DMF was removed under reduced pressure and the residue was partitioned between EtOAc (50 mL) and 10% aqueous Na$_2$CO$_3$. The EtOAc layer was separated, washed with water and brine, dried over anhydrous MgSO$_4$, and filtered. The filtrate solvent was removed under reduced pressure to give N-(tert-butoxycarbonyl)-3-cyclopropyl-D-alanyl-N-[5-chloro-2-(1H-1,2,4-triazol-1-yl)benzyl]-L-prolinamide as a gum (0.058 g). HPLC RT=2.18 min, Method B; LCMS (M+H): 517, 519.

Step E: 3-cyclopropyl-D-alanyl-N-[5-chloro-2-(1H-1 2,4-triazol-1-yl)benzyl]-L-prolinamide N-(tert-butoxycarbonyl)-3-cyclopropyl-D-alanyl-N-[5-chloro-2-(1H-1,2,4-triazol-1-yl)benzyl]-L-prolinamide from the previous step (0.058 g, 0.112 mmol) was dissolved in EtOAc (2 mL) and cooled with stirring to 0° C. HCl/EtOAc (3.55M, 1.5 mL) was added. The bath was removed and the mixture stirred for 2 hours. HPLC analysis indicated completion and the solvent was removed under reduced pressure. The residue was triturated with EtOAc and filtered to give the hydrochloride salt of 3-cyclopropyl-D-alanyl-N-[5-chloro-2-(1H-1,2,4-triazol-1-yl)benzyl]-L-prolinamide as a solid. (0.045 g). HPLC RT=1.04 min, Method B; LCMS (M+H): 417, 419; $^1$H NMR (400 MHz, DMSO-d$_6$): δ 8.96, (s, 1H), 8.67 (t, J=6 Hz, 1H), 8.27–8.33 (m, 3H), 7.50–7.56 (m, 3H), 4.32 (dd, J=2, 9 Hz, 1H), 4.10–4.25 (m, 2H), 3.78–3.86 (m, 1H), 3.54–3.60 (m, 1H), 2.06–2.11 (m, 1H), 1.81–1.93 (m, 3H), 1.68–1.75 (m, 1H, 154–1.60 (m, 1H), 0.77–0.85 (m, 1H), 0.44–0.48 (m, 2H), 0.07–0.16 (m, 2H).

EXAMPLE 32

Preparation of N-[5-chloro-2-(1H-tetraazol-1-yl) benzyl]-1-[(2R)-2-hydroxy-3,3-dimethylbutanoyl]-L-prolinamide

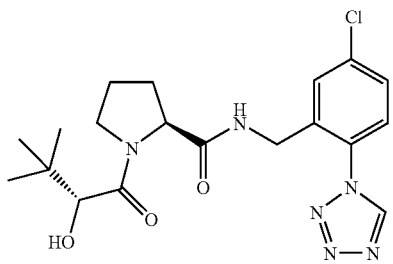

Step A: 2R-hydroxy-3,3-dimethylbutyric acid

To a stirred solution of 2R-amino-3,3-dimethylbutyric acid (5.0 g, 38.1 mmol) in 80 mL of 1N sulfuric acid at −10° C. was added slowly dropwise a solution of sodium nitrite (5.26 g, 76.2 mmol) in water (25 mL). After addition, the reaction was allowed to slowly equilibrate to ambient temperature over 20 h. Sodium chloride (10 g) was added and the solution was extracted with diethyl ether (2×100 mL). The combined organic extracts were dried over anhydrous sodium sulfate and filtered. The filtrate solvent was removed under reduced pressure. The residue was purified by preparative HPLC using a chiralpak AD column (5 cm×50 cm) using 5% ethanol in 95% hexanes with 0.2% TFA as the mobile phase at a flow rate of 80 mL/min. The product-containing fractions were concentrated in vacuo. 2R-hydroxy-3,3-dimethylbutyric acid was obtained as an oil that crystallizes on standing (2.2 g). $^1$H NMR (400 MHz, CDCl$_3$): δ8.0–6.8 (br s, 2H), 3.9 (s, 1H), 1.0 (s, 9H)).

Step B N-[5-chloro-2-(1H-tetraazol-1-yl)benzyl]-1-[(2R)-2-hydroxy-3,3-dimethylbutanoyl]-L-prolinamide The title compound was prepared from N-[5-chloro-2-(1H-tetraazol-1-yl)benzyl]-L-prolinamide (hydrochloride salt, Example 26, Step B, 55 mg, 0.16mmol) and (2R)-hydroxy-3,3-dimethylbutyric acid (22 mg, 0.16 mmol) essentially according to the EDC coupling procedure described in Example 27, Step C (without the deprotection step). The mixture was stirred for 18 h at ambient temperature and was then concentrated in vacuo. The residue was purified directly by semi-preparative HPLC using a Waters Xterra RP8 column (1.9 cm×30 cm) using a 30 minute gradient of 95/5-water/MeCN to 100% MeCN with 0.1% TFA as the mobile phase at a flow rate of 20 mL/min. The product-containing fractions were concentrated in vacuo to afford the title compound as a white crystalline solid (62 mg). HPLC RT=2.86 min (Method A); LCMS m/z=421.3; $^1$H NMR (400 MHz, CDCl$_3$): δ 9.15 (s, 1H), 7.62 (d, J=2.2 Hz, 1H), 7.51 (br m, 1H), 7.44 (dd, J=2.2, 8.4 Hz, 1H), 7.25 (d, J=8.6 Hz, 1H), 4.5 (dd, J=3.8, 8.6 Hz, 1H) 4.25 (d, J=5.3 Hz, 1H), 4.2 (m, 1H), 4.15 (s, 1H) 3.69 (m, 1H), 3.57 (m, 1H), 2.73 (br s, 1H), 1.8–2.1 (m, 4H), 1.0 (s, 9H)).

EXAMPLE 33

Preparation of 3-cyclohexyl-D-alanyl-N-[5-chloro-2-(1H-tetraazol-1-yl)benzyl]-L-prolinamide

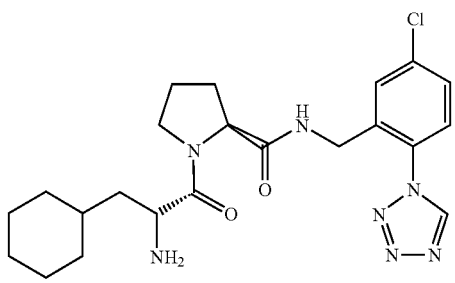

Step A: N$^1$-tert-butoxycarbonyl-3-cyclohexyl-D-alanyl-N$^2$-[5-chloro-2-(1H-tetraazol-1-yl)benzyl]-L-prolinamide The title compound was prepared from Boc-D-cyclohexyl-Ala (54 mg, 0.20 mmol) and N-[5-chloro-2-(1H-tetraazol-1-yl)benzyl]-L-prolinamide (Example 26, Step B, 76 mg, 0.02 mmol) essentially according to the EDC coupling procedure described in Example 27, Step C (omitting the deprotection step). The solvent was removed in vacuo. Silica gel chromatography (5% MeOH/CHCl$_3$) afforded a colorless gum. LCMS (M+H): 560.7.

Step B: 3-cyclohexyl-D-alanyl-N-[5-chloro-2-(1H-tetraazol-1-yl)benzyl]-L-prolinamide To a solution of N$^1$-tert-butoxycarbonyl-3-cyclohexyl-D-alanyl-N$^2$-[5-chloro-2-(1H-tetraazol-1-yl)benzyl]-L-prolinamide (from Step A above) in CH$_2$Cl$_2$ (2.0 mL) was added excess TFA (0.5 mL). The solvent was removed in vacuo and the residual oil was purified by reverse phase HPLC to give the TFA salt of the title compound as a foamy white solid. LCMS (M+H): 460.2. $^1$H NMR (CD$_3$OD, 400 MHz): δ 9.57 (s, 1 H), 8.64 (m, 1 H), 7.74 (d, J=2.0 Hz, 1 H), 7.57 (dd, J=2.0 Hz, 8.4 Hz, 1 H), 7.49 (d, J=8.4 Hz, 1 H), 4.33–4.29 (m, 2 H), 4.21–4.11 (m, 2 H), 3.75–3.70 (m, 1 H), 3.57–3.48 (m, 1 H), 2.26–2.16 (m, 1 H), 2.12–1.97 (m, 2 H), 1.92–1.63 (m, 6 H), 1.42 (m, 1 H), 1.37–1.16 (m, 4 H), 1.09–0.88 (m, 3 H).

EXAMPLE 34

Preparation of 3-cyclohexyl-D-alanyl-N-[5-chloro-2-(1H-triazol-1-yl)benzyl]-L-prolinamide

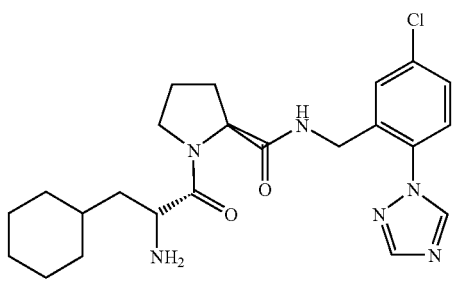

The title compound was prepared from Boc-D-cyclohexyl-Ala (22 mg, 0.08 mmol) and N-[5-chloro-2-(1H-1,2, 4-triazol-1-yl)benzyl)-L-prolinamide (Example 27, Step B, 27 mg, 0.08 mmol) essentially according to the procedures described in Example 33 above and was isolated as a foamy white solid. LCMS (M+H): 459.2.

$^1$H NM (CD$_3$OD, 400 MHz): δ 8.79 (s, 1 H), 8.22 (s, 1 H), 7.67 (d, J=2.0, 1 H), 7.50 (dd, J=2.0 Hz, 8.4 Hz, 1 H), 7.45 (d, J=8.4 Hz, 1 H), 4.41–4.34 (m, 2 H), 4.25–4.19 (m, 2 H), 3.75–3.71 (m, 1 H), 3.55–3.48 (m, 1 H), 2.25–2.18 (m, 1 H), 2.09–1.99 (m, 2 H), 1.93–1.87 (m, 2 H), 1.76–1.66 (m, 7 H), 1.43 (m, 1 H), 1.34–1.20 (m, 2 H), 1.06–0.96 (m, 2 H).

EXAMPLE 35

Preparation of 3-Cyclohexyl-D-alanyl-N-[2-(1H-tetraazol-1-yl)benzyl]-L-prolinamide

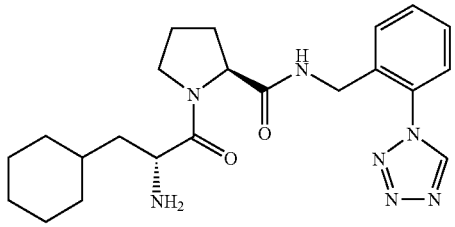

Step A: N-[2-(1H-tetraazol-1-yl)benzyl]-L-prolinamide

The title compound was prepared essentially according to the EDC coupling procedure described in Example 26 using 1-[2-(1H-tetraazol-1-yl)phenyl]methanamine (Example 1, 55 mg, 0.31 mmol) and Boc-L-proline (67 mg, 0.31 mmol) followed by purification of the intermediate (silica gel chromatography, 50%–70% EtOAc/hexanes) and deprotection using 4.0 M HCl in dioxane. The hydrochloride salt of the title compound was isolated as a colorless gum: LCMS (M+H): 273.1. $^1$H NMR (CD$_3$OD, 400 MHz): δ 9.58 (s, 1 H), 7.66–7.65 (m, 2 H), 7.59–7.55 (m, 1 H), 7.51–7.49 (m, 1 H), 4.39–4.26 (m, 2 H), 4.16 (m, 1 H), 3.31–3.28 (m, 2 H), 2.36–2.33 (m, 1 H), 1.98–1.87 (m, 3 H).

Step B: N$^1$-(tert-butoxycarbonyl)-3-cyclohexyl-D-alanyl-N$^2$-[2-(1H-tetraazol-1-yl)benzyl]-L-prolinamide The title compound was prepared from N-[2-(1H-tetraazol-1-yl)benzyl]-L-prolinamide hydrochloride (25 mg, 0.08 mmol) and Boc-D-cyclohexyl-Ala (22 mg, 0.08 mmol) essentially according to the EDC coupling procedure described in Example 27, Step C (omitting the deprotection step). The crude product was carried on directly to deprotection. LCMS (M+H): 526.2.

Step C: 3-Cyclohexyl-D-alanyl-N-[2-(1H-tetraazol-1-yl)benzyl]-L-prolinamide

N$^1$-(tert-butoxycarbonyl)-3-cyclohexyl-D-alanyl-N$^2$-[2-(1H-tetraazol-1-yl)benzyl]-L-prolinamide (42 mg, 0.08 mmol) was deprotected using TFA as described in Example 33, Step B to afford the title compound as a pale yellow solid. LCMS (M+H): 426.2. $^1$H NMR (CD$_3$OD, 400 MHz): δ 9.53 (s, 1 H), 8.60 (m, 1 H), 7.71–7.62 (m, 2 H), 7.58–7.54 (m, 1 H), 7.50–7.48 (m, 1 H), 4.32–4.28 (m, 2 H), 4.26–4.25 (m, 1 H), 4.21–4.18 (m, 1 H), 3.75–3.70 (m, 1 H), 3.54–3.48 (m, 1 H), 2.22–2.15 (m, 1 H), 2.08–1.96 (m, 2 H), 1.92–1.86 (m, 2 H), 1.76–1.63 (m, 6 H), 1.41–1.16 (br m,4 H), 1.09–0.96 (m,2 H).

EXAMPLE 36

Preparation of N-[5-chloro-2-(1H-tetraazol-1-yl)benzyl]-1-(2-hydroxy-2-pyridin-2-ylpropanoyl)-L-prolinamide

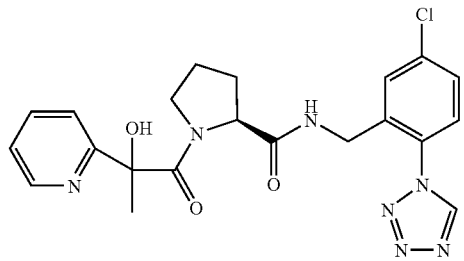

Step A: Ethyl 2-hydroxy-2-(2-pyridyl)acetate

A stirred solution of ethyl 2-oxo-(pyridin-2-yl)acetate (1.0 g, 5.6 mmol) in THF (15 mL) was cooled to −78° C. under an atmosphere of nitrogen. To this solution was added methyl magnesium bromide in THF (6.2 mL of a 1.0 M solution, 6.2 mmol) dropwise over 5 min. The cooling bath was removed and the stirred mixture was allowed to warm to ambient temperature over 2 h. Water (30 mL) was added and the mixture was extracted with EtOAc (50 mL). The organic phase was washed with brine, dried over anhydrous MgSO$_4$, filtered, and the solvent was removed under reduced pressure. The residue was purified by pressurized silica gel column chromatography using 1:2 EtOAc:hexanes as eluant. Product-containing fractions were combined and the solvents were removed under reduced pressure to give ethyl 2-hydroxy-2-(2-pyridyl)acetate as a colorless liquid (0.90 g, 83%; HPLC RT=1.46 min, method A; TLC R$_f$=0.3 (1:2 EtOAc:hex); LCMS m/z=196; $^1$H NMR (400 MHz, CDCl$_3$): δ 8.55 (dd, J=0.9, 4.8 Hz, 1H), 7.74 (dt, J$_d$=1.1 Hz, J$_t$=8.0 Hz, 1H), 7.57 (d, J=8.0 Hz, 1H), 7.26 (dd, J=4.5, 8.0 Hz, 1H), 5.45 (s, 1H), 4.19 (q, J=7.0 Hz, 2H), 1.82 (s, 3H), 1.23 (t, J=7.0 Hz, 3H)).

Step B: 2-Hydroxy-2-(2-pyridyl)acetic acid

To a stirred solution of ethyl 2-hydroxy-2-(2-pyridyl)acetate (0.5 g, 2.56 mmol) in ethanol (5 mL) was added 2.0 M NaOH in water (1.4 mL, 2.8 mmol). The resulting solution was stirred at ambient temperature for 18 h. TLC analysis indicated complete consumption of starting ester. 6.0 M HCl in water (0.46 mL, 2.8 mmol) was added and the solvents were removed under reduced pressure and the resulting solid was dried in vacuo for 18 h to give 2-hydroxy-2-(2-pyridyl)acetic acid as a mixture with sodium chloride.

Step C: N-[5-Chloro-2-(1H-tetraazol-1-yl)benzyl]-1-(2-hydroxy-2-pyridin-2-ylpropanoyl)-L-prolinamide To a solution of 2-hydroxy-2-(2-pyridyl)acetic acid from the previous step (160 mg as a 1:1 mixture with NaCl, 0.71 mmol), N-[5-chloro-2-(1H-tetraazol-1-yl)benzyl]-L-prolinamide (215 mg, 0.71 mmol, HPLC RT=2.25 min, method A), and HOBt hydrate (110 mg, 0.71 mmol) in DMF (5 mL) was added EDC (175 mg, 0.92 mmol). Diisopropylethylamine was then added slowly in portions (~0.1 mL total) to bring the pH of the solution to 6–7 as measured on wetted E. Merck pH indicator strips. The mixture was stirred at ambient temperature for 18 h, and the solvent was removed under reduced pressure. The residue was partitioned between EtOAc (75 mL) and saturated aqueous NaHCO$_3$ (20 mL). The EtOAc layer was separated, dried over anhydrous MgSO$_4$, and filtered. The filtrate solvent was removed under reduced pressure and the residue was purified by pressurized silica gel column chromatography using a gradient elution of 2%, 3%, 4%, 5%, 6% MeOH in dichloromethane. Product-containing fractions were combined and the solvent was removed under reduced pressure to give two diastereomers of the title compound, both as amorphous solids (first eluting diastereomer: 96 mg; TLC $R_f$=0.3 (96:4 CH$_2$Cl$_2$:MeOH); HPLC RT=2.32 min, method A; LC-MS m/z=456; second eluting diastereomer: TLC $R_f$=0.2 (96:4 CH$_2$Cl$_2$:MeOH); HPLC RT=2.33 min, method A; LCMS m/z=456).

EXAMPLE 37

Preparation of N-[5-chloro-2-(1H-tetraazol-1-yl)benzyl]-1-[(2R)-2-hydroxy-2-phenylethanoyl]-L-prolinamide

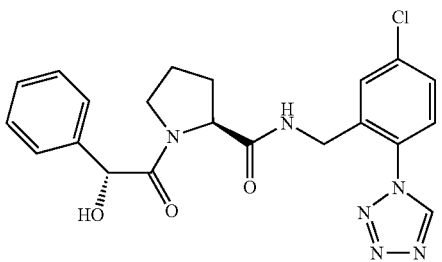

To a solution of R-mandelic acid (60 mg, 0.39 mmol), N-[5-chloro-2-(1H-tetraazol-1-yl)benzyl]-L-prolinamide (Example 26, Step B, 120 mg, 0.39 mmol, HPLC RT=2.25 min, method A), and HOBt hydrate (60 mg, 0.39 mmol) in DMF (3 mL) was added EDC (98 mg, 0.51 mmol). Diisopropylethylamine was then added slowly in portions (~0.05 mL total) to bring the pH of the solution to 6–7 as measured on wetted E. Merck pH indicator strips. The mixture was stirred at ambient temperature for 18 h, and the solvent was removed under reduced pressure. The residue was partitioned between EtOAc (50 mL) and saturated aqueous NaHCO$_3$ (10 mL). The EtOAc layer was separated, dried over anhydrous MgSO$_4$, and filtered. The filtrate solvent was removed under reduced pressure and the residue was purified by pressurized silica gel column chromatography using EtOAc as eluant. Product-containing fractions were combined and the solvent was removed under reduced pressure to give the title compound as an amorphous solid (TLC $R_f$=0.6 (EtOAc); HPLC RT=2.82 min, method A; LCMS m/z=441).

EXAMPLE 38

Preparation of N-[5-chloro-2-(1H-tetraazol-1-yl)benzyl]-1-[(3S)-3-hydroxyleucyl]-L-prolinamide

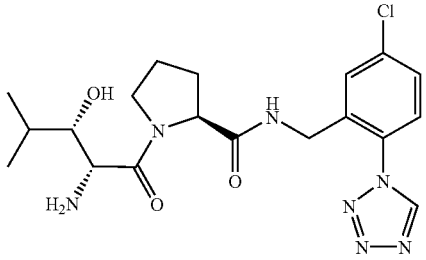

Step A: N-Boc-(3S)-3-hydroxy-D-leucine

To a stirred solution of (3S)-3-hydroxy-D-leucine (0.25 g, 1.7 mmol) in dioxane (10 mL) was added aqueous NaOH (0.90 mL of a 2.0 molar solution, 1.8 mmol) and di-tert-butyl dicarbonate (0.44 g, 2.0 mmol). The mixture was stirred at ambient temperature for 24 h. The solvent was removed in vacuo and the residue was partitioned between water (20 mL) and ether (20 mL). The aqueous layer was separated and stirred with CH$_2$Cl$_2$ (20 mL) while solid citric acid (0.96 g, 5 mmol) was added. The CH$_2$Cl$_2$ layer was separated and the aqueous layer was extracted with another portion of CH$_2$Cl$_2$ (20 mL). The combined CH$_2$Cl$_2$ layers were dried (MgSO$_4$), filtered, and the solvent was removed in vacuo to give N-Boc-(3S)-hydroxy-D-leucine as a foam (0.30 g). HPLC RT=2.67 min, Method A; $^1$H NMR (400 MHz, CDCl$_3$): δ 5.51 (d, J=9 Hz, 1H), 5.0 (br s, 2H), 4.44 (d, J=8 Hz, 2H), 3.79 (d, J=9 Hz, 1H), 1.78 (m, 1H), 1.46 (s, 9H), 1.03 (d, J=7 Hz, 3H), 0.94 (d, J=7 Hz, 3H).

Step B: 1-(2R, 3S-2-tert-butyloxycarbonylamino-3-hydroxy-4-methylpentanoyl)-N-[5-chloro-2-(1H-tetraazol-1-yl)benzyl]-L-prolinamide To a solution of N-Boc-(3S)-3-hydroxy-D-leucine from the previous step (170 mg, 0.68 mmol), N-[5-chloro-2-(1H-tetraazol-1-yl)benzyl]-L-prolinamide (Example 26, Step B, 200 mg, 0.66 mmol, HPLC RT=2.25 min, method A), and HOBt hydrate (110 mg, 0.78 mmol) in DMF (6 mL) was added EDC (177 mg, 0.92 mmol). Diisopropylethylamine was then added in portions (~0.1 mL total) to bring the pH of the solution to 6–7 as measured on wetted E. Merck pH indicator strips. The mixture was stirred at ambient temperature for 2 h, and the solvent was removed under reduced pressure. The residue was partitioned between EtOAc (75 ml) and saturated aqueous NaHCO$_3$ (20 mL). The EtOAc layer was separated, dried over anhydrous MgSO$_4$, and filtered. The filtrate solvent was removed under reduced pressure and the residue was purified by pressurized silica gel column chromatography using EtOAc as eluent. Product-containing fractions were combined and the solvent was removed under reduced pressure to give 1-(2R, 3S-2-tert-butyloxycarbonylamino-3-hydroxy-4-methylpentanoyl)-N-[5-chloro-2-(1H-tetraazol-1-yl)benzyl]-L-prolinamide (240 mg, 71%; TLC $R_f$=0.5 (EtOAc); HPLC RT=3.17 min, Method A; LC-MS m/z=536).

Step C: 1-(2R, 3S-2-Amino-3-hydroxy-4-methypentanoyl)-N-[5-chloro-2-(1H-tetraazol-1-yl)benzyl]-L-prolinamide Into a solution of 1-(2R, 3S-2-tert-butyloxycarbonylamino-3-hydroxy-4-methylpentanoyl)-N-[5-chloro-2-(1H-tetraazol-1-yl)benzyl]-L-prolinamide from the previous step (240 mg, 0.45 mmol) in EtOAc (30mL) at 0° C. was bubbled HCl gas for 5 minutes. The solution was stirred for 15 minutes at 0° C. and concentrated in vacuo to give 1-(2R, 3S-2-Amino-3-hydroxy-4-methylpentanoyl)-N-[5-chloro-2-(1H-tetraazol-1-yl)benzyl]-L-prolinamide as a white powder (0.21 g). HPLC RT=2.42 min, Method A; LC-MS m/z=436.3; $^1$H NMR (400 MHz, CD$_3$OD): δ 9.55 (s, 1H), 7.73 (d, J=2.2 Hz, 1H), 7.57 (dd, J=2.2, 8.42 Hz, 1H), 7.5 (d, J=8.42 Hz, 1H), 4.35 (dd, J=3.0, 8.7 Hz, 1H), 4.25 (app q, J=15.6 Hz, 2H), 4.22 (d, J=4.2 Hz, 1H), 3.78 (m, 1H), 3.63 (dd, J=4.3, 7.1 Hz, 1H), 3.55 (q, J=8.8 Hz, 1H), 2.2 (m, 1H) 2.05 (m, 2H), 1.9 (m, 1H), 1.7 (m, 1H), 1.05 (m, 6H).

EXAMPLE 39

Preparation of 3-isopropylprolyl-N-[5-chloro-2-(1H-1,2,4-triazol-1-yl)benzyl]-L-prolinamide

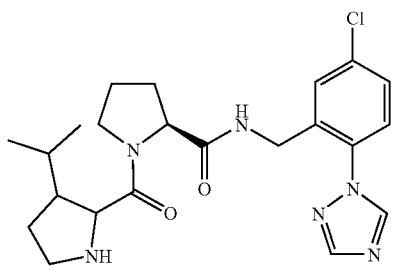

Step A: Diethyl-3-isopropylpyrrolidine-2,2-dicarboxylate

The title compound was prepared from 4-methyl-2-pentenal (1.03 mL, 8.82 mmol) essentially according to the procedure described in Morgan, B. A.; Schafer, D. J. U.S. Pat. No. 4,060,603, Nov. 29, 1977, for the preparation of 4-ethyl-5,5-dicarboethoxy-2-pyrroline, with the following exceptions: the intermediate diethyl-3-isopropylpyrrolidine-2,2-dicarboxylate was carried on crude. LCMS (M+H): 256.1.

Step B: 3-Isopropyl-dl-proline

The title compound was prepared from diethyl-3-isopropylpyrrolidine-2,2-dicarboxylate (3.06 g, 12.0 mmol) essentially according to the basic hydrolysis procedure described in Morgan, B. A.; Schafer, D. J. U.S. Pat. No. 4,060,603, Nov. 29, 1977 for the preparation of 3-ethyl-dl-proline from 2,2-dicarboethoxy-3-ethylpyrrolidine. The product was isolated as a yellow solid. LCMS (M+H): 158.0. $^1$H NMR (CD$_3$OD, 400 MHz): δ 3.70 (d, J=6.4 Hz, 1 H), 3.31–3.27 (m, 1 H), 2.29–2.22 (m, 1 H), 2.08–1.99 (m, 1 H), 1.94–1.74 (m, 3 H), 1.05 (d, J=6.8 Hz), 0.97(d, J=6.8Hz, 3 H).

Step C: 1-(tert-Butoxycarbonyl)-3-isopropyl-dl-proline

To a stirred solution of trans-3-isopropyl-dl-proline (1.88 g, 12.0 mmol) in H$_2$O (12.0 mL), 1 N NaOH (13.0 mL), and dioxane (34.0 mL) at 0° C. was added BOC anhydride (2.88 g, 13.2 mmol) in portions. The reaction was allowed to warm to room temperature and stirred for 72 h. The solvent was removed in vacuo. The remaining residue was taken up in H$_2$O and acidified to pH 2 using 1 N HCl. The aqueous layer was extracted with EtOAc. The organic layer was washed with brine, dried (Na$_2$SO$_4$), and concentrated to a yellow oil. Silica gel chromatography (50%–100% EtOAc/hexanes) afforded the title compound as a yellow solid. LCMS (M+H-BOC): 157.9. $^1$H NMR (CD$_3$OD, 400 MHz): δ 4.01 and 3.92 (rotamers, d, J=5.1 Hz and 6.0 Hz, 1 H), 3.54–3.48 (m, 1 H), 3.42–3.32 (m, 1 H), 2.14–1.95 (m, 2 H), 1.80–1.66 (m, 2 H), 1.43 and 1.42 (BOC rotamers, s, 9 H), 1.00 (d, J=6.8 Hz, 3 H), 0.95 (d, J=6.8 Hz,3H).

Step D: 1-(tert-butoxycarbonyl)-3-isopropylprolyl-N-[5-chloro-2-(1H-1,2,4-triazol-1-yl)benzyl]-L-prolinamide A mixture of 1-(tert-butoxycarbonyl)-3-isopropyl-dl-proline, (77 mg, 0.30 mmol), N-[5-chloro-2-(1H1,2,4-triazol-1-yl)benzyl]-L-prolinamide (Example 27, Step B, 113 mg, 0.30 mmol), HOAt (20 mg, 0.15 mmol), EDC (86 mg, 0.45 mmol) and Et$_3$N (80 μL, 0.60 mmol) in 1.5 mL DMF was stirred at room temperature. The diastereomeric products were separated by reverse phase HPLC (30 min gradient elution with 95:5 H$_2$O/0.1% TFA:CH$_3$CN/0.1% TFA to 5:95 H$_2$O/0.1% TFA:CH$_3$CN/0.1% TFA) and carried on directly to deprotection.

Diastereomer A: LCMS (M+H): 545.5.
Diastereomer B: LCMS (M+H): 545.5.

Step E: 3-isopropylprolyl-N-[5-chloro-2-(1H-1,2,4-triazol-1-yl)benzyl]-L-prolinamide To a stirred solution of diastereomer A of 1-(tert-butoxycarbonyl)-3-isopropylprolyl-N-[5-chloro-2-(1H-1,2,4-triazol-1-yl)benzyl]-L-prolinamide (96 mg, 0.18 mmol) in dioxane (5.0 mL) was added 4.0 N HCl in dioxane in excess. After 1 h, the solvent was removed in vacuo to give the HCl salt of the title compound as a yellow solid. LCMS (M+H): 445.3. $^1$H NMR (CD$_3$OD, 400 MHz): δ 9.05 (s, 1 H), 8.38 (s, 1 H), 7.71 (s, 1 H), 7.51–7.45 (m, 2 H), 4.48–4.42 (m, 2 H), 4.39 (d, J=16.0 Hz, 1 H), 4.24 (d, J=16.4 Hz, 1 H), 3.79–3.48 (m, 3 H), 3.37–3.31 (m, 1 H), 2.44–2.39 (m, 1 H), 2.38–2.23 (m, 1 H), 2.16–2.11 (m, 1 H), 2.09–1.84 (m, 4 H), 1.79–1.71 (m, 1 H), 1.07 (d, J=6.8 Hz, 3 H), 1.01 (d, J=6.4 Hz, 3 H).

Diastereomer B (80 mg, 0.15 mmol) was deprotected in similar fashion to afford the HCl salt of the title compound as a yellow solid. LCMS (M+H): 445.4.

$^1$H NMR (CD$_3$OD, 400 MHz): δ 8.95–8.94 (m, 1 H), 8.32–8.31 (m, 1 H), 7.68–7.67 (m, 1 H), 7.53–7.46 (m, 2 H), 4.41–4.34 (m, 3 H), 4.23 (d, J=15.6 Hz, 1 H), 3.82–3.72 (m, 1 H), 3.63–3.57 (m, 1 H), 3.49–3.43 (m, 1 H), 3.40–3.35 (m, 1 H), 2.39–2.32 (m, 1 H) 2.28–1.89 (m, 5 H), 1.87–1.72 (m, 1 H), 1.04 (d, J=6.8 Hz, 3 H), 1.01 (d, J=6.4 Hz, 3 H).

EXAMPLE 40

Preparation of D-prolyl-N-[5-chloro-2-(1H-tetraazol-1-yl)benzyl]-L-prolinamide

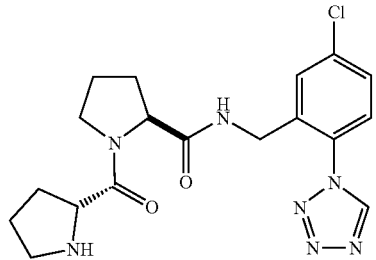

Step A: 1-(tert-Butoxycarbonyl)-D-prolyl-N-[5-chloro-2-(1H-tetraazol-1-yl)benzyl]-L-prolinamide The title compound was prepared from 1-(tert-butoxycarbonyl)-D-proline (49 mg, 0.23 mmol), N-[5-chloro-2-(1H-tetraazol-1-yl)benzyl]-L-prolinamide (Example 26, Step B, 70 mg, 0.23 mmol, 1.0 equiv), EDC (66 mg, 0.34 mmol, 1.5 equiv) and HOAt (16 mg, 0.11 mmol, 0.5 equiv) in DMF (500 μl) essentially according to the procedure described in Example 26, Step C. Preparative reverse phase HPLC [gradient elution with 95:5 water (+0.1% TFA)/CH$_3$CN (+0.1% TFA) to 5:95 water (+0.1% TFA)/CH$_3$CN (+0.1% TFA)] afforded the title compound as a clear oil. $^1$H NMR (400 MHz, CDCl$_3$): δ 9.17 (s, 1 H), 8.11 (br s, 1 H), 7.54 (d, J=2.0 Hz, 1 H), 7.40 (dd, J=2.0, 8.4 Hz, 1 H), 7.23 (d, J=8.4 Hz, 1 H), 4.69–4.66 (m, 1 H), 4.43–4.39 (m, 1 H), 4.18–4.16 (m, 2 H), 4.04–3.99 (m, 1 H), 3.55–3.48 (m, 3 H), 2.27–1.88 (m, 8 H), 1.30 (s, 9 H). LCMS (M+H): 504.3.

Step B: D-prolyl-N-[5-chloro-2-(1H-tetraazol-1-yl)benzyl]-D-prolinamide

The title compound was prepared from 1-(tert-butoxycarbonyl)-D-prolyl-N-[5-chloro-2-(1H-tetraazol-1-yl)benzyl]-L-prolinamide (120 mg, 0.23 mmol) essentially according to the deprotection procedure described in Example 27, Step C. Purification by reverse phase chromatography [95:5 water (+0.1% TFA)/CH$_3$CN (+0.1% TFA) to 5:95 water (+0.1% TFA)/CH$_3$CN (+0.1% TFA)] afforded the compound as a clear oil. $^1$H NMR (400 MHz, CDCl$_3$): δ 9.12 (s, 1 H), 8.06–8.03 (m, 1 H), 7.57 (app s, 1 H), 7.41 (dd, J=2.0, 8.4 Hz, 1 H), 7.23 (d, J=8.4 Hz, 1 H), 4.62 (br s, 1 H), 4.51 (app d, J=8.4 Hz, 1 H), 4.25 (dd, J=5.6, 15.2 Hz, 1 H), 4.06 (dd, J=4.8, 15.6 Hz, 1 H), 3.82–3.77 (m, 1 H), 3.55 (br s, 1 H), 3.49–3.40 (m, 2 H), 2.21–2.11 (m, 5 H), 2.09–1.91 (m, 4 H). LCMS (M+H): 404.3.

EXAMPLE 41

Preparation of N-[5-chloro-2-(1H-tetraazol-1-yl)benzyl]-1-[(2R)-piperidin-2-ylcarbonyl]-L-prolinamide

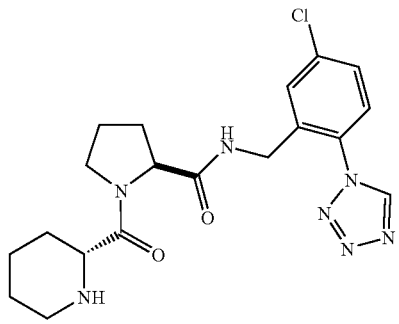

Step A: N-[5-chloro-2-(1H-tetraazol-1-yl)benzyl]-1-[1-(tert-butoxycarbonyl)-(2R)-piperidin-2-ylcarbonyl]-L-prolinamide The title compound was prepared from (2R)-1-(tert-butoxycarbonyl)piperidine-2-carboxylic acid (52 mg, 0.23 mmol), N-[5-chloro-2-(1H-tetraazol-1-yl)benzyl]-L-prolinamide (Example 26, Step B, 70 mg, 0.23 mmol, 1.0 equiv), EDC (66 mg, 0.34 mmol, 1.5 equiv) and HOAt (16 mg, 0.11 mmol, 0.5 equiv) in DMF (500 µl) essentially according to the procedure described in Example 26, Step C. Reverse phase HPLC [95:5 water (+0.1% TFA)/CH$_3$CN (+0.1% TFA) to 5:95 water (+0.1% TFA)/CH$_3$CN (+0.1% TFA)] afforded the title compound as a clear oil. $^1$H NMR (400 MHz, CDCl$_3$): δ 9.16 (s, 1 H), 7.90 (br s, 1 H), 7.59 (s, 1 H), 7.41 (d, J=8.4 Hz, 1 H), 7.24 (d, J =8.4 Hz, 1 H), 4.56 (br s, 1 H), 4.38 (br s, 1 H), 4.18–4.15 (m, 2 H), 3.80 (br s, 1 H), 3.58–3.52 (m, 3 H), 2.15–2.11 (m, 2 H), 2.05–1.98 (m, 2 H), 1.95–1.84 (m, 2 H), 1.70–1.68 (m, 2 H), 1.55 (br s, 2 H), 1.33 (s, 9 H). LCMS (M+H): 518.3.

Step B: N-[5-chloro-2-(1H-tetraazol-1-yl)benzyl]-1-[(2R)-piperidin-2-ylcarbonyl]-L-prolinamide The title compound was prepared from N-[5-chloro-2-(1H-tetraazol-1-yl)benzyl]-1-[1-(tert-butoxycarbonyl)-(2R)-piperidin-2-ylcarbonyl]-L-prolinamide (120 mg, 0.23 mmol) essentially according to the deprotection procedure described in Example 27, Step C. Purification by reverse phase chromatography [95:5 water (+0.1% TFA)/CH$_3$CN (+0.1% TFA) to 5:95 water (+0.1% TFA)/CH$_3$CN (+0.1% TFA)] afforded the compound as a clear oil. $^1$H NMR (400 MHz, CDCl$_3$): δ 9.16 (s, 1 H), 8.15 (br s, 1 H), 7.55 (app s, 1 H), 7.42 (dd, J=2.0, 8.4 Hz, 1 H), 7.27–7.26 (m, 1 H), 4.49 (br s, 1 H), 4.29–4.26 (m, 1 H), 4.11–3.99 (m, 3 H), 3.84 (br s, 1 H), 3.58–3.52 (m, 1 H), 3.43–3.41 (m, 1 H), 3.13 (br s, 1 H), 2.17 (br s, 1 H), 2.11–1.94 (m, 5 H), 1.85–1.62 (m, 4 H). LCMS (M+H): 418.4.

EXAMPLE 42

Preparation of 3-isopropylprolyl-N-[5-chloro-2-(1H-tetraazol-1-yl)benzyl]-L-prolinamide

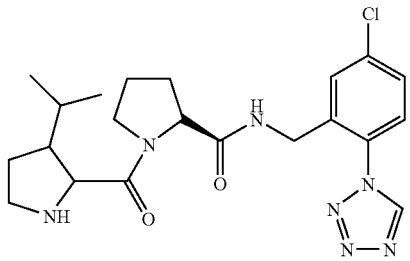

Step A: 3-Isopropylproline

A solution of diethyl-3-isopropylpyrrolidine-2,2-dicarboxylate (Example 39, Step A, 2.27 g, 8.81 mmol) in 6 M HCl (50 mL) was heated to reflux. The solution turned from pale yellow in color to orange with addition of acid, then to brown upon heating. The mixture was stirred overnight at 50° C. Solvent was removed in vacuo to afford the title compound (a mixture of four diastereomers) as a brown oil which was carried on crude. LCMS (M+H): 158.0.

Step B: 1-(tert-Butoxycarbonyl)-3-isopropylproline

The title compound was prepared from 3-isopropylproline (1.78 g, 11.32 mmol) according to the BOC protection procedure described in Example 39, Step C. Silica gel chromatography (70%-100% EtOAc/hexanes) afforded a yellow solid that was a 1:1.5 mixture of trans:cis isomers by $^1$H NMR (racemic at C2, so a total of four diastereomers present). The $^1$H NMR for the trans isomer is reported above in Example 39, Step C and that for the cis isomer is as follows: $^1$H NMR (400 MHz, CD$_3$OD): δ 4.28 and 4.24 (rotamers, d, J=7.6 Hz and 8.0 Hz, 1 H), 3.59 (dd, J=10.0 Hz, 19.6 Hz, 1 H), 3.31–3.22 (m, 1 H), 2.12–1.95 (m, 2 H), 1.81–1.68 (m, 2 H), 1.45 and 1.42 (BOC rotamers, s, 9 H), 1.10–1.08 (m, 3 H), 0.95 (d, J=6.8 Hz, 3 H).

Step C: 3-Isopropylprolyl-N-[5-chloro-2-(1H-tetraazol-1-yl)benzyl]-L-prolinamide 1-(tert-Butoxycarbonyl)-3-isopropylprolyl-N-[5-chloro-2-(1H-tetraazol-1-yl)benzyl]-L-prolinamide was prepared from 1-(tert-butoxycarbonyl)-3-isopropylproline (from the previous step, 252 mg, 0.98 mmol), N-[5-chloro-2-(1H-tetraazol-1-yl)benzyl]-L-prolinamide (Example 26, Step B, 300 mg, 0.98 mmol, 1.0 equiv), EDC (282 mg, 1.47 mmol, 1.5 equiv) and HOAt (67 mg, 0.49 mmol, 0.5 equiv) in DMF (1 mL) essentially according to the procedure described in Example 39, Step D. Reverse phase chromatography [95:5 water (+0.1% TFA)/CH$_3$CN (+0.1% TFA) to 5:95 water (+0.1% TFA)/CH$_3$CN (+0.1% TFA)] afforded the four separate diastereomers as clear oils. Each diastereomer was then dissolved in 2:1 CH$_2$Cl$_2$/TFA (3 mL) and stirred for 1 h. All reactions were concentrated to oils. Purification of each by reverse phase chromatography [95:5 water (+0.1% TFA)/CH$_3$CN (+0.1% TFA) to 50:50 water (+0.1% TFA)/CH$_3$CN (+0.1% TFA)] afforded the diastereomers as clear oils. Diastereomer A (most polar): $^1$H NMR (400 MHz, CD$_3$OD): δ 9.54 (s, 1 H), 7.76 (d, J=2.0 Hz, 1 H), 7.55 (dd, J=2.0, 8.4 Hz, 1 H), 7.49 (d, J=8.4 Hz, 1 H), 4.49 (d, J=4.0 Hz, 1 H), 4.44–4.40 (m, 1 H), 4.33 (d, J=16.0 Hz, 1 H), 4.15 (d, J=15.6

Hz, 1 H), 3.80–3.75 (m, 1 H), 3.61–3.49 (m, 2 H), 3.41–3.35 (m, 1 H), 2.44–2.38 (m, 1 H), 2.30–2.22 (m, 1 H), 2.13–2.09 (m, 1 H), 2.04–1.93 (m, 3 H), 1.91–1.82 (m, 1 H), 1.81–1.73 (m, 1 H), 1.06 (d, J=6.8 Hz, 3 H), 1.01 (d, J=6.4 Hz, 3 H). HRMS (APCI) M+H: calculated for $(C_{21}H_{28}N_7O_2Cl)^+$ 446.2066, found 446.2055. Diastereomer B: $^1$H NMR (400 MHz, CD$_3$OD): δ 9.57 (s, 1 H), 8.61 (t, J=5.6 Hz, 1 H), 7.78 (d, J=2.4 Hz, 1 H), 7.54 (dd, J=2.4, 8.4 Hz, 1 H), 7.49 (d, J=8.4 Hz, 1 H), 4.60 (d, J=8.4 Hz, 1 H), 4.45–4.41 (m, 1 H), 4.32 (dd, J=6.0, 16.0 Hz, 1 H), 4.11 (dd, J=5.2, 16.0 Hz, 1 H), 3.81–3.77 (m, 1 H), 3.62–3.50 (m, 2 H), 3.36–3.30 (m, 1 H), 2.48–2.45 (m, 1 H), 2.26–2.11 (m, 4 H), 2.01–1.87 (m, 3 H), 0.97 (d, J=6.4 Hz, 3 H), 0.81 (d, J=6.4 Hz, 3 H). HRMS (APCI) M+H: calculated for $(C_{21}H_{28}N_7O_2Cl)^+$ 446.2066, found 446.2057. Diastereomer C: $^1$H NMR (400 MHz, CD$_3$OD): δ 9.53 (s, 1 H), 7.73 (d, J=2.4 Hz, 1 H), 7.57 (dd, J=2.4, 8.4 Hz, 1 H), 7.50 (d, J=8.4 Hz, 1 H), 4.37–4.34 (m, 2 H), 4.31 (d, J=15.6 Hz, 1 H), 4.19 (d, 16.0 Hz, 1 H), 3.80–3.76 (m, 1 H), 3.62–3.56 (m, 1 H), 3.48–3.43 (m, 1 H), 3.41–3.34 (m, 2 H), 2.37–2.34 (m, 1 H), 2.24–2.19 (m, 1 H), 2.12–1.88 (m, 4 H), 1.79–1.73 (m, 1 H), 1.02 (dd, J=6.8, 8.4 Hz, 6 H). HRMS (APCI) M+H: calculated for $(C_{21}H_{28}N_7O_2Cl)^+$ 446.2066, found 446.2053. Diastereomer D (least polar): $^1$H NMR (400 MHz, CD$_3$OD): δ 9.53 (s, 1 H), 7.76 (d, J=2.0 Hz, 1 H), 7.56 (dd, J=2.4, 8.4 Hz, 1 H), 7.50 (d, J=8.4 Hz, 1 H), 4.56 (d, J=7.6 Hz, 1 H), 4.36–4.31 (m, 2 H), 4.18 (d, J=15.6 Hz, 1 H), 3.80–3.76 (m, 1 H), 3.64–3.58 (m, 1 H), 3.53–3.48 (m, 1 H), 3.33–3.28 (m, 2 H), 2.53–2.49 (m, 1 H), 2.52–2.17 (m, 2 H), 2.13–2.06 (m, 1 H), 2.02–1.89 (m, 2 H), 1.74–1.69 (m, 1 H), 0.96 (d, J=6.8 Hz, 3 H), 0.95 (d, J=6.8 Hz, 3 H). HRMS (APCI) M+H: calculated for $(C_{21}H_{28}N_7O_2Cl)^+$ 446.2066, found 446.2054.

EXAMPLE 43

Preparation of 3-methylprolyl-N-[5-chloro-2-(1H-tetraazol-1yl)benzyl]-L-prolinamide

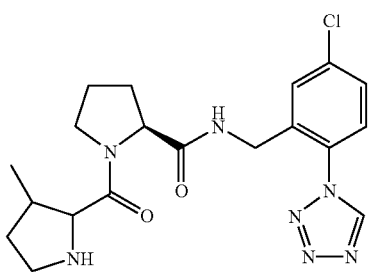

Step A: Diethyl-3-methylpyrrolidine-2,2-dicarboxylate

The title compound was prepared from crotonaldehyde (0.80 mL, 9.7 mmol) essentially according to the procedure described in Morgan, B. A.; Schafer, D. J. U.S. Pat. No. 4,060,603, Nov. 29, 1977, for the preparation of 4-ethyl-5,5-dicarboethoxy-2-pyrroline, with the following exceptions: the intermediate diethyl-3-methylpyrrolidine-2,2-dicarboxylate was carried on crude. LCMS (M+H): 230.0.

Step B: Trans-3-methyl-dl-proline

The title compound was prepared by acidic hydrolysis of diethyl-3-methylpyrrolidine-2,2-dicarboxylate according to the procedure described in Morgan, B. A.; Schafer, D. J. U.S. Pat. No. 4,060,603 for the preparation of 3,3-dimethyl-dl-proline from 2,2-dicarboethoxy-3,3-dimethylpyrrolidine.

Step C: 1-(tert-Butoxycarbonyl)-3-methyl-dl-proline

Trans-3-methyl-dl-proline (2.0 g, 15.5 mmol) was BOC protected according to the procedure described in Example 39, Step C above. Silica gel chromatography (50%-100% EtOAc/hexanes) afforded the title compound as a yellow oil. LCMS (M+H): 230.6. $^1$H NMR (CD$_3$OD, 400 MHz): δ 4.86–4.15 (m, 1 H), 3.72–3.54 (m, 2 H), 2.40–2.25 (m, 1 H), 2.02–1.96 (m, 1 H), 1.71–1.45 (m, 1 H), 1.42 (s, 9 H), 1.18 and 1.07 (rotamers, d, J=6.8 Hz, 3 H).

Step D: 1-(tert-butoxycarbonyl)-3-methylprolyl-N-[5-chloro-2-(1H-tetraazol-1-yl)benzyl]-L-prolinamide The title compound was prepared as a mixture of diastereomers from 1-(tert-butoxycarbonyl-3-methyl-dl-proline (16 mg, 0.07 mmol) and N-[5-chloro-2-(1H-tetraazol-1-yl)benzyl]-L-prolinamide (Example 26, Step B, 21 mg, 0.07 mmol), essentially according to the EDC coupling procedure described in Example 39, Step D. The diastereomeric products were separated by reverse phase HPLC and were carried on directly to deprotection.

Diastereomer A: LCMS (M+H): 518.2.
Diastereomer B: LCMS (M+H): 518.3.

Step E: 3-methylprolyl-N-[5-chloro-2-(1H-tetraazol-1-yl)benzyl]-L-prolinamide

To a stirred solution of diastereomer A of 1-(tert-butoxycarbonyl)-3-methylprolyl-N-[5-chloro-2-(1H-tetraazol-1-yl)benzyl]-L-prolinamide (17 mg, 0.03 mmol) in CH$_2$Cl$_2$ (1.0 mL) at rt was added excess TFA. The solvent was removed in vacuo to afford the TFA salt of the title compound. LCMS (M+H): 418.2. $^1$H NMR (CD$_3$OD, 400 MHz): δ 9.58–9.54 (m, 1 H), 8.59 (m, 1 H), 7.73 (s, 1 H), 7.62–7.48 (m, 2 H), 4.51–4.13 (m, 4 H), 3.73–3.68 (m, 1 H), 3.63–3.39 (m, 3 H), 2.99–2.64 (m, 1 H), 2.33–2.11 (m, 2 H), 2.00–1.73 (m, 4 H), 1.27 and 1.00 (rotamers, d, J=7.2 Hz, 3 H).

Diastereomer B (10 mg, 0.02 mmol) was deprotected in similar fashion to afford the TFA salt of the title compound. LCMS (M+H): 418.2. $^1$H NMR (CD$_3$OD, 400 MHz): δ 9.53 (m, 1 H), 7.73–7.71 (m, 1 H), 7.58–7.49 (m, 2 H), 4.56–4.17 (m, 4 H), 3.75–3.71 (m, 1 H), 3.61–3.41 (m, 3 H), 2.92–2.56 (m, 1 H), 2.33–2.17 (m, 2 H), 2.09–1.74 (m, 4 H), 1.25 and 0.96 (rotamers, d, J=6.8 Hz, 7.2 Hz, 3 H).

EXAMPLE 44

Preparation of (3S)-3-methyl-D-prolyl-N-[5-chloro-2-(1H-tetraazol-1-yl)benzyl]-L-prolinamide

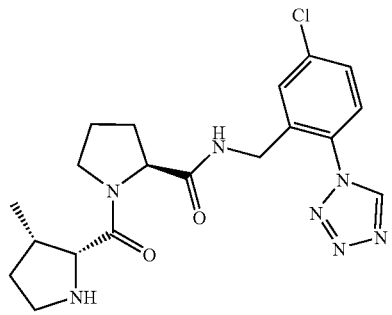

Step A: (R)-But-3-enyl-(1-phenyl-ethyl)-amine

The title compound was prepared essentially according to the procedure described in Lorthiois, E.; Marek, I.; Normant, J. F. J. Org. Chem. 1998, 63, 2442–2450.

Step B: (R)-[But-3-enyl-(1-phenyl-ethyl)-amino]-acetic acid benzyl ester

The title compound was prepared essentially according to the procedure described in Karoyan, P.; Chassaing, G. *Tetrahedron: Asymm*. 1997, 8, 2025–2032.

Step C: Benzyl (3S)-3-methyl-1-(1-phenylethyl)-D-prolinate

The title compound was prepared from (R)-[but-3-enyl-(1-phenyl-ethyl)-amino]-acetic acid benzyl ester essentially according to the cyclization protocol described in Karoyan, P.; Chassaing, G. *Tetrahedron: Asymm*. 1997, 8, 2025–2032 with the following modifications: LDA was added at −40° C., then the solution was warmed to 0° C. for 10 min, then re-cooled to −40° C. for the zinc bromide addition. The transmetallation step was omitted and the anion was quenched directly with 2:1 saturated NH$_4$Cl:ammonium hydroxide. Extractive workup (Et$_2$O) afforded an orange oil which was purified by silica gel chromatography (5–10% EtOAc-hexanes) to give the title compound as a yellow oil.

$^1$H NMR (400 MHz, CDCl$_3$): δ 7.37–7.20 (m, 10 H), 5.10 (d, J=12.3 Hz, 1 H), 5.03 (d, J=12.3 Hz, 1 H), 3.72–3.67 (m, 1 H), 3.38 (d, J=8.3 Hz, 1 H), 3.07–3.02 (m, 1 H) 2.92–2.86 (m, 1 H), 2.45–2.39 (m, 1 H), 1.99–1.94 (m, 1 H), 1.66–1.56 (m, 1 H), 1.33 (d, J=6.6 Hz, 3 H), 0.91 (d, J=8.5 Hz, 3 H).

Step D: (3S)-1-(tert-butoxycarbonyl)-3-methyl-D-proline

A mixture of benzyl (3S)-3-methyl-1-(1-phenylethyl)-D-prolinate (1.39 g, 4.29 mmol), BOC anhydride (2.06 g, 9.43 mmol) and 10% Pd/C (250 mg) in THF (125 mL) was stirred under hydrogen atmosphere (balloon) for 16 h. The mixture was filtered through Celite and the filter cake was washed with MeOH. The filtrate was evaporated to give a viscous pale yellow oil which was re-dissolved in EtOH (50 mL). Pearlman's catalyst (560 mg) was added and the mixture shaken on a Parr hydrogenation apparatus under 40 psi hydrogen for 16 h. The mixture was filtered through Celite and concentrated to an oil which was purified by silica gel chromatography (40% EtOAc-hexanes then 3% AcOH-EtOAc). The fractions which contained product were concentrated and the residue azeotroped with toluene to remove residual acetic acid. The title compound was isolated as a viscous oil. $^1$H NMR (400 MHz, CDCl$_3$): δ 4.28 and 4.21 (d, rotamers, J=7.7 and 8.4 Hz, 1 H), 3.72–3.67 and 3.63–3.58 (m, rotamers, 1 H), 3.37–3.31 (br m, 1 H), 2.00–1.93 (m, 1 H), 1.75–1.70 (m, 1 H), 1.46 and 1.42 (s, Boc rotamers, 9 H), 1.09 (d, J=6.4 Hz, 3 H).

Step E: (3S)-3-methyl-D-prolyl-N-[5-chloro-2-(1H-tetraazol-1-yl)benzyl]-L-prolinamide The title compound was prepared from (3S)-1-(tert-butoxycarbonyl)-3-methyl-D-proline (15 mg, 0.07 mmol), N-[5-chloro-2-(1H-tetraazol-1-yl)benzyl]-L-prolinamide (Example 26, Step B, 20 mg, 0.07 mmol, 1.0 equiv), EDC (19 mg, 0.10 mmol, 1.5 equiv) and HOAt (5 mg, 0.03 mmol, 0.5 equiv) in DMF (1 mL) followed by deprotection in TFA-CH$_2$Cl$_2$ essentially according to the procedure described in Example 27, Step C. Purification by reverse phase chromatography [95:5 water (+0.1% TFA)/CH$_3$CN (+0.1% TFA) to 50:50 water (+0.1% TFA)/CH$_3$CN (+0.1% TFA)] afforded the compound as a clear oil. $^1$H NMR (400 MHz, CDCl$_3$): δ 9.10 (s, 1 H), 8.07–8.01 (m, 1 H), 7.56 (app s, 1 H), 7.41 (dd, J=1.6, 8.4 Hz, 1 H), 7.23 (d, J=8.4 Hz, 1 H), 4.65 (br s, 1 H), 4.57–4.55 (m, 1 H), 4.29 (dd, J=6.0, 15.6 Hz, 1 H), 4.05 (dd, J=5.2, 15.2 Hz, 1 H), 3.83–3.77 (m, 1 H), 3.62 (br s, 1 H), 3.45–3.38 (m, 2 H), 2.97 (br s, 1 H), 2.41–1.88 (m, 7 H), 1.01 (d, J=7.2 Hz, 3 H). HRMS (APCI) M+H: calcd for (C$_{19}$H$_{24}$N$_7$O$_2$Cl)$^+$ 418.1753, found 418.1741.

EXAMPLE 45

Preparation of 3,3-dimethylprolyl-N-[5-chloro-2-(1H-tetraazol-1-yl)benzyl]-L-prolinamide

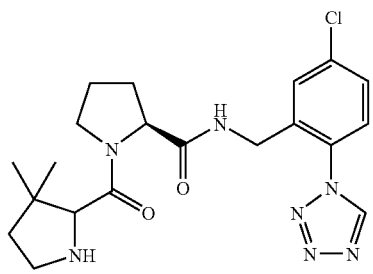

Step A: 3,3-Dimethyl-dl-proline

The procedure for the preparation of 3,3-dimethyl-dl-proline as described in Morgan, B. A.; Schafer, D. J. U.S. Pat. No. 4,060,603, Nov. 29, 1977, was followed, with the following modifications: the intermediate 2,2-dicarboethoxy-3,3-dimethyl-pyrrolidine was chromatographed on a silica gel column eluting with 50% EtOAc/hexanes. Acid hydrolysis of this intermediate as described in U.S. Pat. No. 4,060,603 afforded the crude 3,3-dimethyl-dl-proline as a brown solid. $^1$H NMR (CD$_3$OD, 400 MHz): δ 3.97 (s, 1 H), 3.40 (m, 2 H), 2.00 (m, 2 H), 1.37 (s, 3 H), 1.07 (s, 3 H).

Step B: 1-(tert-Butoxycarbonyl)-3,3-dimethyl-dl-proline 3,3-Dimethyl-dl-proline (1.00 g, 6.98 mmol) was BOC protected according to the procedure described in Example 39, Step C. Silica gel chromatography (gradient elution with 30% EtOAc/hexanes—100% EtOAc—5% AcOH/EtOAc) afforded the product as a brown solid. LCMS (M+H): 244.1. $^1$H NMR (CD$_3$OD, 400 MHz): δ 3.81 and 3.78 (m, rotamers, 1 H), 3.50 (m, 1 H), 3.40 (m, 1 H), 1.85 (m, 1H), 1.62 (m, 1 H), 1.45 and 1.42 (s, Boc rotamers, 9 H), 1.16 (s, 3 H), 1.07 (s, 3 H).

Step C: 1-(tert-butoxycarbonyl)-3,3-dimethylprolyl-N-[5-chloro-2-(1H-tetraazol-yl)-benzyl]-L-prolinamide The title compound was prepared as a mixture of diastereomers from 1-(tert-butoxycarbonyl)-3,3-dimethyl-dl-proline (61 mg, 0.25 mmol) and N-[5-chloro-2-(1H-tetrazol-1-yl)benzyl]-L-prolinamide (Example 26, Step B, 95 mg, 0.25 mmol) essentially according to the EDC coupling procedure described in Example 39, Step D. The diastereomeric products were separated by reverse phase HPLC and were carried on directly to deprotection.

Diastereomer A: LCMS (M+H): 532.3.
Diastereomer B: LCMS (M+H): 532.0.

Step D: 3,3-dimethylprolyl-N-[5-chloro-2-(1H-tetraazol-1-yl)benzyl]-L-prolinamide To a stirred solution of diastereomer A of 1-(tert-butoxycarbonyl)-3,3dimethylprolyl-N-[5-chloro-2-(1H-tetraazol-yl)-benzyl]-L-prolinamide (64 mg, 0.12 mmol) in approximately 1 mL CH$_2$Cl$_2$ at rt was added an excess of TFA. The solvent was removed in vacuo and the residue was purified by reverse phase HPLC to afford the TFA salt of the title compound. LCMS (M+H): 432.2. $^1$H NMR (CD$_3$OD, 400 MHz): δ 9.54 (s, 1 H), 8.63–8.61 (m, 1 H), 7.76 (d, J=2.0 Hz, 1 H), 7.54 (dd, J=2.2 Hz, 8.2 Hz, 1 H), 7.48 (d, J=8.8 Hz, 1 H), 4.45–4.42 (m, 1 H), 4.32 (dd, J=6.0 Hz, 15.6 Hz, 1 H), 4.24 (m, 1 H), 4.13 (dd, J=5.2 Hz, 16.0 Hz, 1 H), 3.78–3.75

(m, 1 H), 3.64–3.58 (m, 1 H), 3.54–3.47 (m, 1 H), 3.42–3.35 (m, 1 H), 2.69–2.22 (m, 1 H), 2.14–2.10 (m, 1 H), 2.01–1.87 (m, 4 H), 1.34 (s, 3 H), 1.05 (s, 3 H).

Diastereomer B was deprotected in similar fashion to afford the TFA salt of the title compound. LCMS (M+H): 432.2. $^1$H NMR (CD$_3$OD, 400 MHz): δ 9.53 (s, 1 H), 7.73, (d, J=2.0 Hz, 1 H), 7.57 (dd, J=2.0 Hz, 8.4 Hz, 1 H), 7.50 (d, J=8.4 Hz, 1 H), 4.37–4.11 (m, 4 H), 3.78–3.72 (m, 1 H), 3.63–3.39 (m, 3 H), 2.26–2.19 (m, 2 H), 2.08–1.88 (m, 4 H), 1.32 (s, 3 H), 1.09 (s, 3 H).

EXAMPLE 46

Preparation of N-[5-Chloro-2-(1H-tetraazol-1-yl) benzyl]-1-[(2-methylazetidin-2-yl)carbonyl]-L-prolinamide

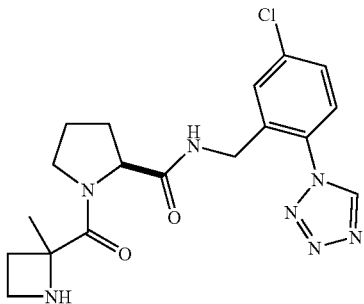

Step A: N-[5-chloro-2-(1H-tetraazol-1-yl)benzyl]-1-[(1-tert-butoxycarbonyl-2-methylazetidin-2-yl)carbonyl]-L-prolinamide EDC (0.104 g, 0.54 mmol), HOAt (24.6 mg, 0.18 mmol), NMM (0.079 mL, 0.72 mmol), and N-[5-chloro-2-(1H-tetraazol-1-yl)benzyl]-L-prolinamide hydrochloride (Example 26, Step B, 0.143 g, 0.42 mmol) were added to a stirred solution of racemic 1-(tert-butoxycarbonyl)-2-methylazetidine-2-carboxylic acid (0.143 g, 0.36 mmol in DMF (1.1 mL). After 3 h at room temperature the reaction was partitioned between EtOAc and water. The organic layer was washed with brine, dried (Na$_2$SO$_4$) and concentrated in vacuo. The two diastereomers were separated and purified by reverse phase HPLC. The more polar diastereomer was concentrated in vacuo. N-[5-chloro-2-(1H-tetraazol-1-yl)benzyl]-1-[(1-tert-butoxycarbonyl-2-methylazetidin-2-yl)carbonyl]-L-prolinamide (diastereomer A) was obtained as a glass. MS m/z=404.6).

The less polar diastereomer was concentrated in vacuo. N-[5-chloro-2-(1H-tetraazol-1-yl)benzyl]-1-[(1-tert-butoxycarbonyl-2-methylazetidin-2-yl)carbonyl]-L-prolinamide (diastereomer B) was obtained as a clear oil. MS m/z=404.6.

Step B: N-[5-Chloro-2-(1H-tetraazol-1-yl)benzyl]-1-[(2-methylazetidin-2-yl)carbonyl]-L-prolinamide TFA (3.0 mL) was added to a stirred solution of N-[5-chloro-2-2(1H-tetraazol-1-yl)benzyl]-1-[(1-tert-butoxycarbonyl-2-methylazetidin-2-yl)carbonyl]-L-prolinamide (diastereomer A, 46 mg, 0.091 mmol) in CH$_2$Cl$_2$ (6.0 mL). After 1 h the mixture was concentrated in vacuo and the residue was purified by reverse phase HPLC (C$_{18}$, eluting with acetonitrile/0.1% TFA/water). N-[5-Chloro-2-(1H-tetraazol-1-yl)benzyl]-1-[(2-methylazetidin-2-yl)carbonyl]-L-prolinamide (diastereomer A) was obtained as the TFA salt as a glass. MS m/z=404.61; $^1$H NMR (CD$_3$OD, 400 MHz), δ 1.83 (m, 1H), 1.89 (s, 3H), 1.95 (m, 1H), 2.06 (m, 1H), 2.24 (m, 1H), 2.59 (m, 1H), 2.97 (m, 1H), 3.49 (m, 2H), 3.75 (m, 1H), 4.08 (m, 1H), 4.20 (m, 1H), 4.33 (m, 1H), 4.44 (dd, J=6.0, 8.2 Hz, 1H), 7.49 (d, J=8.4 Hz, 1H), 7.55 (dd, J=2.3, 8.4 Hz, 1H), 7.74 (d, J=2.3 Hz, 1H), 9.52 (s, 1H).

N-[5-chloro-2-(1H-tetraazol-1-yl)benzyl]-1-[(1-tert-butoxycarbonyl-2-methylazetidin-2-yl)carbonyl]-L-prolinamide (diastereomer B, 61 mg, 0.121 mmol) was deprotected and purified in the same manner. N-[5-chloro-2-(1H-tetraazol-1-yl)benzyl]-1-[(2-methylazetidin-2-yl)carbonyl]-L-prolinamide (diastereomer B) was obtained as the TFA salt as a glass. MS m/z=404.6; $^1$H NMR (CD$_3$OD, 400 MHz), δ 1.83 (obscured m, 1H), 1.86 (s, 3H), 1.95 (m, 1H), 2.05 (m, 1H), 2.22 (m, 1H), 2.56 (m, 1H), 3.12 (q, J=10.1 Hz, 1 H), 3.48 (m, 1H), 3.79 (m, 1H), 4.08 (q, J=9.3 Hz, 1H), 4.21 (d, J=15.5 Hz, 1H), 4.45 (m, 2H), 7.51 (d, J=8.4 Hz, 1H), 7.57 (dd, J=2.0, 8.4 Hz, 1H), 7.75 (d, J=1.7 Hz, 1H), 9.56 (s, 1H).

EXAMPLE 47

Preparation of 1-(Azetidin-2-ylcarbonyl)-N-[5-chloro-2-(1H-tetraazol-1-yl)benzyl]-L-prolinamide

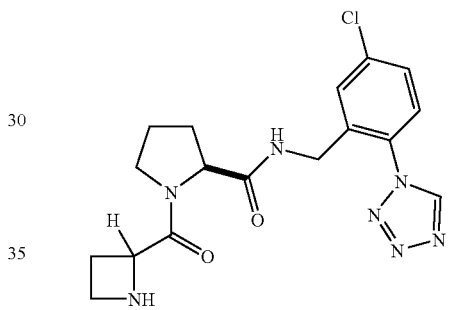

Step A: 1-(1-tert-butoxycarbonylazetidin-2-ylcarbonyl)-N-[5-chloro-2-(1H-tetraazol-1-yl)benzyl]-L-prolinamide N-[5-chloro-2-(1H-tetraazol-1-yl)benzyl]-L-prolinamide hydrochloride (Example 26, Step B, 80.1 mg, 0.23 mmol) was coupled to racemic 1-(tert-butoxycarbonyl)azetidine-2-carboxylic acid (42.5 mg, 0.21 mmol) and then purified using the procedure described in Example 46, Step A. The less polar product diastereomer (A) of 1-(1-tert-butoxycarbonylazetidin-2-ylcarbonyl)-N-[5-chloro-2-(1H-tetraazol-1-yl)benzyl]-L-prolinade by reverse phase HPLC was obtained as a glass. MS m/z=390.6.

The more polar diastereomer (B) by reverse phase HPLC was obtained as a glass. MS m/z=390.6.

Step B: 1-(Azetidin-2-ylcarbonyl)-N-[5-chloro-2-(1H-tetraazol-1-yl)benzyl]-L-prolinamide 1-(1-tert-Butoxycarbonylazetidin-2-ylcarbonyl)-N-[5-chloro-2-(1H-tetraazol-1-yl)benzyl]-L-prolinamide (diastereomer A, 31 mg, 0.063 mmol) was deprotected using the procedure described in Example 46, Step B. 1-(Azetidin-2-ylcarbonyl)-N-[5-chloro-2-(1H-tetraazol-1-yl)benzyl]-L-prolinade (diastereomer A) was obtained as the TFA salt as a glass. MS m/z=390.6; $^1$H NMR (CD$_3$OD, 400 MHz), δ 1.93 (m, 1H), 2.02 (m, 1H), 2.21 (m, 1H), 2.60 (m, 1H), 2.88 (m, 1H), 3.54 (m, 2H), 3.93 (m, 1H), 4.14 (m, 1H), 4.20 (d, J=15.5 Hz, 1H), 4.30 (d, J=15.5 Hz, 1H), 4.40 (m, 1H), 5.28 (t, J=9.0 Hz, 1H), 7.49 (d, J=8.4 Hz, 1H), 7.56 (dd, J=1.3, 8.4 Hz, 1H), 7.71 (s, 1H), 9.54 (s, 1H).

1-(1-tert-Butoxycarbonylazetidin-2-ylcarbonyl)-N-[5-chloro-2-(1H-tetraazol-1-yl)benzyl]-L-prolinamide (diastereomer B, 0.022 g, 0.045 mmol) was deprotected and purified in the same way. 1-(Azetidin-2-ylcarbonyl)-N-[5-chloro-2-(1H-tetraazol-1-yl)benzyl]-L-prolinamide (diastereomer B) was obtained as the TFA salt as a glass. MS m/z=390.6; $^1$H NMR (CD$_3$OD, 400 MHz), δ 1.88 (m, 1H), 1.96 (m, 1H), 2.04 (m, 1H), 2.20 (m, 1H), 2.69 (m, 1H), 2.88 (m, 1H), 3.35 (m, 1H), 3.48 (m, 1H), 4.01 (m, 1H), 4.15 (m, 1H), 4.23 (m, 1H), 4.34 (m, 1H), 4.39 (m, 1H), 5.26 (t, J=8.7 Hz, 17.4 Hz, 1H), 7.51 (d, J=8.6 Hz, 1H), 7.58 (dd, J=2.4, 8.6 Hz, 1H), 7.74 (d, J=2.4 Hz, 1H), 9.55 (s, 1H).

EXAMPLE 48

Preparation of 3-cyclopropyl-D-alanyl-N-[5-fluoro-2-(1H-1,2,4-triazol-1-yl)benzyl}-L-prolinamide

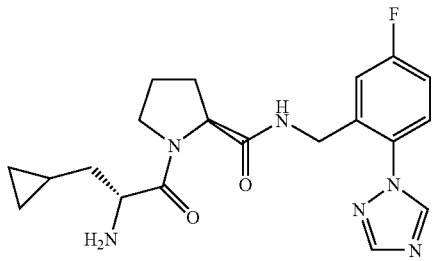

Step A: 5-fluoro-2-(1H-1,2,4-triazol-1-yl)benzonitrile

A mixture of 2,5-difluorobenzonitrile (500 mg, 3.6 mmol), 1,2,4-triazole (273 mg, 3.9 mmol) and Cs$_2$CO$_3$ (1.27 g, 3.9 mmol) in DMF (10 mL) was heated at 80° C. for 2 days. The solvent was removed under reduced pressure. The residue was partitioned between H$_2$O and EtOAc. The layers were separated and the aqueous layer extracted with EtOAc (×3). The combined organic extracts were washed with brine, dried over MgSO$_4$, filtered and concentrated to give the title compound as an off white solid (596 mg) along with a minor bis-alkylated byproduct. $^1$H NMR (400 MHz, CDCl$_3$): δ 8.71 (s, 1H), 8.19 (s, 1H), 7.75–7.98 (m, 1H), 7.48–7.57 (m, 2H).

Step B: 1-[5-fluoro-2-(1H-1,2,4-triazol-1-yl)phenyl]methanamine

A suspension of 5-fluoro-2-(1H-1,2,4-triazol-1-yl)benzonitrile (200 mg, 1.0 mmol) in methanol saturated with ammonia (30 mL) was stirred in the presence of Raney nickel (50% slurry in water, washed with methanol, catalytic amount) under a hydrogen atmosphere (balloon) for 2 days. The reaction mixture was filtered through Celite and concentrated to give the title compound as a light green foam (150 mg). $^1$H NMR (400 MHz, DMSO-d$_6$): δ 8.69 (br, 2H) 7.8 (br s, 1H), 7.42 (s, 1H), 7.29 (s, 1H), 7.17 (s, 1H). 3.98 (br s, 2H)

Step C: N-[5-fluoro-2-(1H-1,2,4-triazol-1-yl)benzyl]-L-prolinamide

To a stirred solution of 1-[5-fluoro-2-(1H-1,2,4-triazol-1-yl)phenyl]methanamine (245 mg, 1.06 mmol), 1-(tert-butoxycarbonyl)-L-proline (236 mg, 1.1 mmol) and HOBt hydrate (143 mg, 1.06 mmol) in DMF (6 mL) was added EDC (203 mg, 1.06 mmol). Diisopropylethylamine was then added in portions (~0.6 mL total) to bring the pH of the solution to 6–7 as measured on wetted E. Merck pH indicator strips. The mixture was stirred at ambient temperature for 4 hours, at which time HPLC analysis indicated complete consumption of the proline starting material. The DMF was removed under reduced pressure and the residue was partitioned between EtOAc and saturated aqueous NaHCO$_3$. The EtOAc layer was separated, dried over anhydrous MgSO$_4$, and filtered. The filtrate solvent was removed under reduced pressure and the oily residue was purified by preparative on a 10 g Redi-Sep column using 5% CH$_3$OH/EtOAc over 40 min. The product fractions were combined and the solvent removed under reduced pressure to give 219 mg of an oil. HPLC-RT=1.71 min (Method A); LCMS (M+H): 390 m/e. This oil was dissolved in 2 ml EtOAc and treated with 1 ml of 5.5 N HCl/EtOAc. The mixture was stirred for 3 days at room temperature. The solvent was removed in vacuo and the residue triturated with EtOAc to give 137 mg of the title compound as the hydrochloride salt (HPLC RT =0.17 min, Method A). LCMS (M+H): 290 m/e.

Step D: N-{tert-butoxycarbonyl}-3-cyclopropyl-D-alanyl-N-[5-fluoro-2-{1H-1,2,4-triazol-1-yl}benzyl]-L-prolinamide To a stirred solution of N-[5-fluoro-2-(1H-1,2,4-triazol-1-yl)benzyl]-L-prolinamide (86 mg, 0.25 mmol), N-(tert-butoxycarbonyl)-3-cyclopropyl-D-alanine (Example 31, Step C, 57 mg, 0.25 mmol) and HOBt hydrate (33 mg, 0.25 mmol) in DMF (2 mL) was added EDC (48 mg, 0.25 mmol). Diisopropylethylamine was then added in portions (0.1 mL total) to bring the pH of the solution to 6–7 as measured on wetted E. Merck pH indicator strips. The mixture was stirred at ambient temperature for 4 hours. The DMF was removed under reduced pressure and the residue was partitioned between EtOAc and saturated aqueous NaHCO$_3$. The EtOAc layer was separated, dried over anhydrous MgSO$_4$, and filtered. The filtrate solvent was removed under reduced pressure and the oily residue was purified by preparative reverse phase HPLC eluting with 95/5 to 5/95 1%TFA H2O/CH3CN in 30 min at a flow rate of 15 mL/min. The product fractions were combined and lyophilized to give 35 mg of the title compound. $^1$H NMR (400 MHz, CDCl$_3$): δ 8.35 (s, 1H), 8.12 (s, 1H), 7.63 (m, 1H), 7.23–7.29 (m, 1H), 7.02–7.06 (m, 1H), 5.17 (d, J=5.5 Hz, 1H 4.62 (d, J=5.6 Hz, 1H), 4.22–4.41 (m, 4H), 3.94 (br, s, 1H), 3.60 (m, 1H), 2.34 (s, 1H), 1.98 (s, 2H), 1.44 (m, 1H), 1.30 (s, 9H), 0.71–0.73 (m, 1H), 0.47–0.51 (m, 2H), 0.12 (br s, 2H).

Step E: 3-Cyclopropyl-D-alanyl-N-[5-fluoro-2-{1H-1,2,4-triazol-1-yl}benzyl]-L-prolinamide A solution of N-{tert-butoxycarbonyl}-3-cyclopropyl-D-alanyl-N-[5-fluoro-2-{1H-1,2,4-triazol-1-yl }benzyl]-L-prolinamide (35 mg, 0.069 mmol) in EtOAc (1 mL) was treated with 1 mL of 3.5N HCl/EtOAc at 0° C. for 1 h and at room temperature for 3 h. The solvent was removed under reduced pressure and the residue triturated with EtOAc to give 22 mg of the title compound as the hydrochloride salt. $^1$H NMR (400 MHz, CDCl$_3$): d 8.9 (s, 1H), 8.73 (br s, 1H), 8.35 (br, 2H), 8.23 (s, 1H), 7.48–7.51 (m, 1H), 7.24–7.29 (m, 2H), 4.27–4.30 (d, J=8.52 Hz, 1H), 4.07–4.14 (m, 3H), 3.55 (m, 2H), 2.09 (m, 1H), 1.84–1.88 (m, 3H), 1.67–1.72 (m, 1H), 1.51–1.55 (m, 1H), 0.78 (m, 1H), 0.42 (m, 2H), 0.06–0.11 (m, 2H).

EXAMPLE 49

Preparation of 3-cyclopropyl-D-alanyl-N-[5-fluoro-2-(1H-tetraazol-1-yl)benzyl]-L-prolinamide

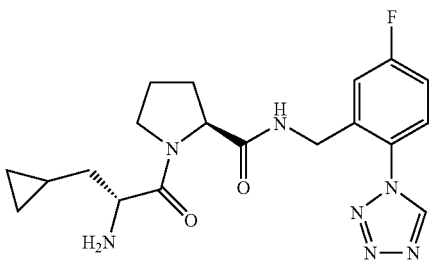

Step A: 1-[5-Fluoro-2-(1H-tetraazol-1-yl)phenyl]methanamine

The title compound was prepared essentially according to the procedures described in Example 1, starting from 2-amino-5-fluorobenzoic acid. $^1$H NMR (400 MHz, CDCl$_3$) δ 9.14 (s, 1H), 7.37–7.42 (m, 2H), 7.17 (td, J=3, 8 Hz, 1H), 3.67 (s, 2H).

Step B: N-[5-fluoro-2-(1H-tetraazol-1-yl)benzyl]-L-prolinamide

The title compound was prepared essentially according to the procedures described in Example 26, Step B, starting from 1-[5-fluoro-2-(1H-tetraazol-1-yl)phenyl]methanamine and Boc-L-proline.

Step C: 3-cyclopropyl-D-alanyl-N-[5-fluoro-2-(1H-tetraazol-1-yl)benzyl]-L-prolinamide The title compound was prepared from N-[5-fluoro-2-(1H-tetraazol-1-yl)benzyl]-L-prolinamide and N-(tert-butoxycarbonyl)-3-cyclopropyl-D-alanine (Example 31, Step C) followed by deprotection with HCl-EtOAc essentially according to the procedures described in Example 31, Steps D and E. HPLC RT=0.93 min (Method B); LCMS (M+H): 402; $^1$H NMR (400 MHz, DMSO-d$_6$): δ 9.86 (s, 1H), 8.66 (t, J=6 Hz, 1H), 8.22–8.35 (m, 2H), 7.64–7.67 (m, 1H), 7.38–7.39 (m, 2H), 4.18–4.30 (m, 1H), 4.00–4.22 (m, 3H), 3.73–3.82 (m, 1H), 3.52–3.58 (m, 1H), 2.0–2.13 (m, 1H), 1.77–1.94 (m, 3H), 1.65–1.74 (m, 1H), 1.52–1.61 (m, 1H), 0.77–0.85 (m, 1H), 0.44–0.48 (m, 2H), 0.05–0.17 (m, 2H).

EXAMPLE 50

Preparation of 4-methyl-D-leucyl-N-[2-(1H-tetraazol-1-yl)-5-(trifluoromethyl)benzyl]-L-prolinamide

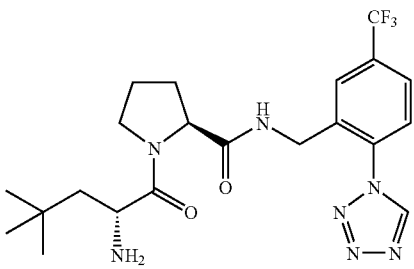

Step A: 2-(1H-tetraazol-1-yl)-5-(trifluoromethyl)benzonitrile and 2-(2H-tetraazol-2-yl)-5-(trifluoromethyl)benzonitrile To a stirred solution of 2-fluoro-5-(trifluoromethyl)benzonitrile (661 mg, 3.5 mmol) and tetrazole (318 mg, 4.5 mmol) in anhydrous DMF (5 mL) was added cesium carbonate (1.48 g, 4.5 mmol). The mixture was immersed in a pre-heated 90° C. oil bath and heated under nitrogen atmosphere behind a blast shield for 1 h. The dark mixture was then cooled to room temperature and poured over crushed ice. The mixture was extracted twice with Et$_2$O. The combined organic layers were dried (anhydrous Na$_2$SO$_4$) and concentrated to an orange oil. Silica gel chromatography (25% EtOAc-hexanes) afforded separation of the two major products, with 2-(2H-tetraazol-2-yl)-5-(trifluoromethyl)benzonitrile eluting first followed by 2-(1H-tetraazol-1-yl)-5-(trifluoromethyl)benzonitrile, both orange-yellow solids: 2-(1H-tetraazol-1-yl)-5-(trifluoromethyl)benzonitrile: $^1$H NMR (400 MHz, CDCl$_3$): δ 9.39 (s, 1H), 8.20 (s, 1H), 8.14–8.11 (m, 2H). 2-(2H-tetraazol-2-yl)-5-(trifluoromethyl)benzonitrile: $^1$H NMR (400 MHz, CDCl$_3$): δ 8.84 (s, 1H), 8.37 (d, J=8.6 Hz, 1H), 8.22 (s, 1H), 8.12–8.09 (m, 1H).

Step B: 1-[2-(1H-tetraazol-1-yl)-5-(trifluoromethyl)phenyl]methanamine

To a solution of 2-(1H-tetraazol-1-yl)-5-(trifluoromethyl)benzonitrile (166 mg, 0.69 mmol) in saturated ethanolic ammonia (12 mL) was added Raney nickel (50% slurry in water; the water was decanted and the catalyst rinsed with EtOH three times before use). The mixture was quickly degassed and purged with Ar, and was then placed under H$_2$ atmosphere (balloon) and stirred for 16 h. The mixture was then filtered through Celite and the filter cake was rinsed thoroughly with EtOH. The filtrate was concentrated to a brown oil. Silica gel chromatography (70% EtOAc-hexanes then 5% MeOH-CHCl$_3$) afforded the title compound as an orange-brown solid. $^1$H NMR (400 MHz, CDCl$_3$): δ 9.41 (s, 1H), 7.93 (br s, 1H), 7.76 (d, J=8.0 Hz, 1H), 7.62 (d, J=8.0 Hz, 1H), 3.81 (s, 2H), 1.57 (br s, 2H). LCMS (M+H): 243.9.

Step C: 1-(tert-Butoxycarbonyl)-N-[2-(1H-tetraazol-1-yl)-5-(trifluoromethyl)benzyl]-L-prolinamide A mixture of 1-(tert-butoxycarbonyl)-L-proline (39 mg, 0.18 mmol), 1-[2-(1H-tetraazol-1-yl)-5-(trifluoromethyl)phenyl]methanamine (42 mg, 0.17 mmol), EDC (49 mg, 0.26 mmol) and HOAt (12 mg, 0.09 mmol) in DMF (1 mL) was stirred at room temperature for 2 h. The crude product was purified by reverse phase HPLC followed by neutralization of an aqueous slurry of the compound with saturated aqueous K$_2$CO$_3$ and repeated extraction of the resulting aqueous mixture with EtOAc (the aqueous layer was saturated with NaCl before each extraction). The combined organic extracts were dried (anhydrous Na$_2$SO$_4$) and concentrated to afford the title compound as an oil which was carried on directly to the deprotection step (Step D below). LCMS (M+H): 441.2.

Step D: N-[2-(1H-tetraazol-1-yl)-5-(trifluoromethyl)benzyl]-L-prolinamide

To a stirred, cold (0° C.) solution of 1-(tert-butoxycarbonyl)-N-[2-(1H-tetraazol-1-yl)-5-(trifluoromethyl)benzyl]-L-prolinamide (92 mg, 0.209 mmol) in EtOAc (1 mL) was added a freshly-prepared, saturated solution of HCl in EtOAc (6 mL). The mixture was stirred at room temperature for 2 h. The solvent was removed in vacuo and the residue azeotroped with diethyl ether to afford the hydrochloride salt of the title compound as an off-white solid. $^1$H NMR (400 MHz, CD$_3$OD): δ 9.66 (s, 1H), 8.83 (s, 1H), 7.98 (s, 1H), 7.91 (d, J=8.0 Hz, 1H), 7.77 (d, J=8.0 Hz, 1 H), 4.66–4.40 (m, 2H), 4.20 (apparent t, J=8.0 Hz, 1H), 3.40–3.35 (m, 2H), 2.41–2.33 (m, 1H), 2.06–1.88 (m, 3H). LCMS (M+H): 341.1.

Step E: N-(tert-butoxycarbonyl)-4-methyl-D-leucyl-N-[2-(1H-tetraazol-1-yl)-5-(trifluoromethyl)benzyl]-L-prolinamide A mixture of N-[2-(1H-tetraazol-1-yl)-5-(trifluoromethyl)benzyl]-L-prolinamide hydrochloride (35 mg, 0.09 mmol), N-(tert-butoxycarbonyl)-4-methyl-D-leucine (24 mg, 0.10 mmol), EDC (27 mg, 0.14 mmol), HOAt (6.3 mg, 0.05 mmol) and Hünig's base (34 mL, 0.20 mmol) in DMF (1.2 mL) was stirred at room temperature for 16 h. The title compound was isolated by extractive workup (EtOAc) and silica gel chromatography (60%-80% EtOAc-hexanes) as an oily foam which was carried on directly to the deprotection step. $^1$H NMR (400 MHz, CDCl$_3$): δ 9.20 (s, 1H), 7.88 (s, 1H), 7.78 (br m, 1H), 7.71 (d, J=8.2 Hz, 1H), 7.45 (d, J=8.0 Hz, 1H), 4.97 (d, J=6.0 Hz, 1H), 4.59 (d, J=6.4 Hz, 1H), 4.32–4.20 (m, 2H), 3.99–3.95 (m, 1H), 3.51–3.45 (m, 1H), 2.31–2.29 (m, 1H), 2.05–1.92 (m, 3H), 1.62–1.52 (m, 2H), 1.28 (s, 9H), 1.01 (s, 9H). LCMS (M+H): 568.3.

Step F: 4-Methyl-D-leucyl-N-[2-(1H-tetraazol-1-yl)-5-(trifluoromethyl)benzyl]-L-prolinamide TFA (1 mL) was added to a solution of N-(tert-butoxycarbonyl)-4-methyl-D-leucyl-N-[2-(1H-tetraazol-1-yl)-5-(trifluoromethyl)benzyl]-L-prolinamide (32 mg, 0.06 mmol) in dry CH$_2$Cl$_2$ (3 mL). The solution was stirred at room temperature for 30 min and was then concentrated in vacuo. The title compound was isolated by reverse phase HPLC as a white foam. $^1$H NMR (400 MHz, CD$_3$OD): δ 9.62 (s, 1H), 8.03 (s, 1H), 7.89 (dd, J=1.5, 8.2 Hz, 1H), 7.74 (d, J=8.3 Hz, 1H), 4.42 (d, J=15.6 Hz, 1H), 4.35 (d, J=15.6 Hz, 1H), 4.30 (dd, J=3.7, 8.6 Hz, 1H), 4.17 (apparent t, J=6.4 Hz, 1H), 3.83–3.78 (m, 1H), 3.62–3.56 (m, 1H), 2.25–2.18 (m, 1H), 2.15–1.85 (m, 4H), 1.64 (dd, J=6.8, 14.8 Hz, 1H), 1.01 (s, 9H). HRMS (ESI, M+H): 468.2324 (found); 468.2335 (calculated).

EXAMPLE 51

Preparation of 4-methyl-D-leucyl-N-[2-(2H-tetraazol-2-yl)-5-(trifluoromethyl)benzyl]-L-prolinamide

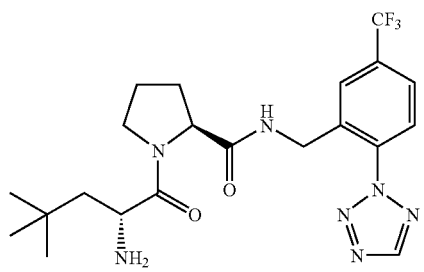

The title compound was prepared from 2-(2H-tetraazol-2-yl)-5(trifluoromethyl)benzonitrile (Example 50, Step A) essentially according to the procedures described in Example 50 above and was isolated as a white foam. $^1$H NMR (400 MHz, CD3OD): δ 9.03 (s, 1H), 8.04 (s, 1H), 8.01 (d, J=8.4 Hz, 1H), 7.89 (dd, J=1.6, 8.4 Hz, 1H), 4.64 (d, J=15.6 Hz, 1H), 4.59 (d, J=15.6 Hz, 1H), 4.37 (dd, J=3.6, 8.8 Hz, 1H), 4.17 (apparent t, J=6.0 Hz, 1H), 3.83–3.78 (m, 1H), 3.62–3.56 (m, 1H), 2.26–2.17 (m, 1H), 2.10–2.01 (m, 2H), 1.93 (dd, J=6.0, 14.8 Hz, 1H), 1.91–1.86 (m, 1H), 1.65 (dd, J=6.8, 14.8 Hz, 1H), 1.01 (s, 9H). HRMS (ESI, M+H): 468.2325 (found); 468.2335 (calculated).

EXAMPLE 52

Preparation of 1-[(2R)-2-amino-2-cyclohexylethanoyl]-N-[5-chloro-2-(4-chloro-1,2,5-thiadiazol-3-yl)benzyl]-L-prolinamide

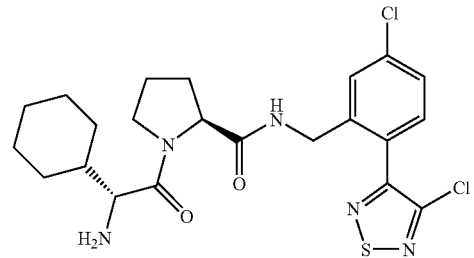

Step A: 4-Chloro-2-methylbenzaldehyde

To a stirred −78° C. solution of 4-chloro-2-methylbenzonitrile (5.00 g, 32.98 mmol) in Et$_2$O (190 mL) was added 1 M DIBAL in THF (66.0 mL) over 10 min. After 5 h additional 1M DIBAL in THF (3.30 mL) was added dropwise and the solution was stirred for 1 hour. The reaction was quenched with water followed by concentrated H$_2$SO$_4$ and stirred at ambient temperature for 16 h. The solution was extracted into Et$_2$O, dried (Na$_2$SO$_4$) and reduced in vacuo. 4-Chloro-2-methylbenzaldehyde was isolated as a yellow oil. $^1$H NMR (CDCl$_3$, 400 MHz) δ 2.59 (s, 3H), 7.19 (s, 1H), 7.26 (d, J=8.2 Hz, 1H), 7.66 (d, J=8.2 Hz, 1H), 10.15 (s, 1H).

Step B: Amino-(4-chloro-2-methylphenyl)acetonitrile

A solution of sodium metabisulfite (2.07 g, 10.9 mmol) in water (20 mL) was added to 4-chloro-2-methylbenzaldehyde (3.37 g, 21.8 mmol). Concentrated ammonium hydroxide (4.25 mL, 62.9 mmol) was added and the solution was stirred for 15 min. Sodium cyanide (1.07 g, 21.8 mmol) was added and the solution was stirred at for 16 h. Methanol (20 mL) was added and the resulting solution was stirred at ambient temperature for 16 h. The solution was extracted into EtOAc and the organic layer was washed with 10% aqueous ammonium hydroxide and then was extracted into 1 M HCl. The aqueous layer was basified with solid sodium carbonate and extracted into EtOAc. The organic phase was dried (Na$_2$SO$_4$) and reduced in vacuo. To a solution of the resulting solid in EtOAc was added 4 M HCl in dioxane (2.1 mL). Amino-(4-chloro-2-methylphenyl)acetonitrile was isolated as the hydrochloride salt. $^1$H NMR (CDCl$_3$, 400 MHz) δ 2.42 (s, 3H), 4.97 (t, J=7.6 Hz, 1H), 7.25 (d, J=8.2 Hz, 1H), 7.26 (s, 1H), 7.51 (d, J=8.2 Hz, 1H).

Step C: 3-Chloro-4-(4-chloro-2-methylphenyl)-1,2,5-thiadiazole

To a stirred solution of sulfur monochloride (1.93 mL, 24.10 mmol) in DMF (3.6 mL) was added dropwise a solution of amino-(4-chloro-2-methylphenyl)acetonitrile hydrochloride (1.744 g, 8.03 mmol) in a minimum volume of DMF. After 16 h the solution was quenched with water and extracted into ether. The organic phase was dried (Na$_2$SO$_4$) and reduced in vacuo. The resulting solid was purified by flash chromatography on silica (eluting with EtOAc/hexanes gradient, 1–4% EtOAc). 3-Chloro-4-(4-chloro-2-methylphenyl)-1,2,5-thiadiazole was isolated as a solid. ¹H NMR (CDCl₃, 400 MHz) δ 2.25 (s, 3H), 7.33 (m, 3H).

Step D: 3-[2-(Bromomethyl)-4-chlorophenyl]-4-chloro-1,2,5-thiadiazole

A mixture of 3-chloro-4-(4-chloro-2-methylphenyl)-1,2,5-thiadiazole (0.211 g, 0.86 mmol), NBS (0.153 g, 0.86 mmol) and benzoyl peroxide (10.4 mg, 0.04 mmol) in carbon tetrachloride (5.0 mL) were refluxed for 1 h. More benzoyl peroxide (10.4 mg, 0.04 mmol) was added and the solution was refluxed for a further 16 h. The resulting suspension was filtered, rinsing with ether. The filtrate was washed with 10% aqueous sodium sulfite, saturated aqueous sodium bicarbonate solution and brine. The ether layer was separated, dried (Na₂SO₄) and reduced in vacuo. The residue was purified by flash chromatography on silica (eluting with EtOAc/hexanes gradient, 1–3% EtOAc). 3-[2-(Bromomethyl)-4-chlorophenyl]-4-chloro-1,2,5-thiadiazole was isolated as a yellow oil. ¹H NMR (CDCl₃, 400 MHz) δ 4.51 (s, 2H), 7.43 (s, 2H), 7.55 (s, 1H).

Step E: 3-[2-(Azidomethyl)-4-chlorophenyl]-4-chloro-1,2,5-thiadiazole

A solution of 3-[2-(bromomethyl)-4-chlorophenyl]-4-chloro-1,2,5-thiadiazole (0.193 g, 0.60 mmol) and sodium azide (38.7 mg, 0.60 mmol) in DMF (0.6 mL) was stirred at 60° C. for 16 h. The solution was partitioned between water and ether. The organic phase was separated, washed with brine, dried (Na₂SO₄) and reduced in vacuo. 3-[2-(Azidomethyl)-4-chlorophenyl]-4-chloro-1,2,5-thiadiazole was isolated as an oil. MS m/z=258.5.

Step F: 1-[5-Chloro-2-(4-chloro-1,2,5-thiadiazol-3-yl)phenyl]methanamine

To a stirred solution of 3-[2-(azidomethyl)-4-chlorophenyl]-4-chloro-1,2,5-thiadiazole (0.205 g, 0.72 mmol) and water (0.01 mL, 0.72 mmol) in THF (1.5 mL) was added triphenyl phosphine (0.188 g, 0.72 mmol). The solution was refluxed 1 h then stirred at ambient temperature for 16 h. The solution was reduced in vacuo and the residue was dissolved in MeOH. KOH (1 pellet) was added and the solution was refluxed 5 min. The solution was reduced in vacuo and partitioned between 1 M HCl and EtOAc. The aqueous phase was separated, basified with 1 M NaOH and extracted into ether. The organic phase was separated, dried (Na₂SO₄) and reduced in vacuo. The residue was purified by flash chromatography on silica (eluting with EtOAc/hexanes gradient, 5–10% EtOAc followed by 0.9% MeOH/0.1% NH₄OH/chloroform). 1-[5-Chloro-2-(4-chloro-1,2,5-thiadiazole-3-yl)phenyl]methanamine was isolated as a yellow oil. MS m/z=260.5.

Step G: 1-{(2R)-2-[(tert-Butoxycarbonyl)amino]-2-cyclohexylethanoyl}-N-[5-chloro-2-(4-chloro-1,2,5-thiadiazol-3-yl)benzyl]-L-prolinamide To a stirred solution of 1-[5-chloro-2-(4-chloro-1,2,5-thiadiazol-3-yl)phenyl]methanamine (28.1 mg, 0.11 mmol), 1-{(2R)-2-[(tert-butoxycarbonyl)amino]-2-cyclohexylethanoyl}-L-proline (prepared by standard peptide coupling protocols, 38.3 mg, 0.11 mmol) and HOAt (19.1 mg, 0.14 mmol) in DMF (1.0 mL) was added EDC (26.9 g, 0.14 mmol). After 16 h the mixture was partitioned between EtOAc and water. The organic phase was washed with brine dried (Na₂SO₄) and reduced in vacuo. The residue was purified by HPLC (C₁₈ eluting with an acetonitrile/water/0.1% TFA gradient). 1-{(2R)-2-[(tert-Butoxycarbonyl)amino]-2-cyclohexylethanoyl}-N-[5-chloro-2-(4-chloro-1,2,5-thiadiazol-3-yl)benzyl]-L-prolinamide was obtained as a solid. LCMS m/z=596.5.

Step H: 1-[(2R)-2-amino-2-cyclohexylethanoyl]-N-[5-chloro-2-(4-chloro-1,2,5-thiadiazol-3-yl)]-L-prolinamide HCl gas was bubbled through a stirred 0° C. solution of 1-{(2R)-2-[(tert-butoxycarbonyl)amino]-2-cyclohexylethanoyl}-N-[5-chloro-2-(4-chloro-1,2,5-thiadiazol-3-yl)benzyl]-L-prolinamide (41.1 mg, 0.07 mmol) CH₂Cl₂ (1.0 mL) for 15 min. The solution was reduced in vacuo. 1-[(2R)-2-amino-2-cyclohexylethanoyl]-N-[5-chloro-2-(4-chloro-1,2,5-thiadiazol-3-yl)benzyl]-L-prolinamide hydrochloride was isolated as a solid. LCMS m/z=496.5.

EXAMPLE 53

Preparation of 1-[(2R)-2-amino-2-cyclohexylethanoyl]-N-[5-chloro-2-(1,2,5thiadiazol-3-yl)benzyl]-L-prolinamide

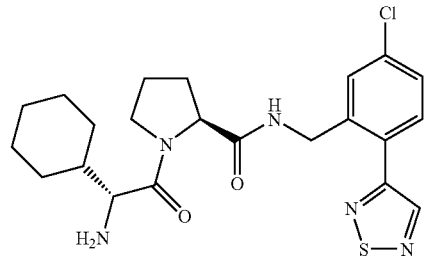

Step A: 3-(4-Chloro-2-methylphenyl)-1,2,5-thiadiazole

To a stirred solution of 3-chloro-4-(4-chloro-2-methylphenyl)-1,2,5-thiadiazole (0.503 g, 2.05 mmol) in THF (5.0 mL) was added 2 M lithium borohydride in THF (2.05 mL, 4.10 mmol). The reaction was stirred at ambient temperature for 15 min then was quenched with water and extracted into EtOAc. The organic phase was dried (Na₂SO₄) and reduced in vacuo. The residue was purified by flash chromatography (eluting with CH₂Cl₂/hexanes gradient, 1–15% CH₂Cl₂). 3-(4-Chloro-2-methylphenyl)-1,2,5-thiadiazole was isolated as a solid. ¹H NMR (CDCl₃, 400 MHz) δ 2.49 (s, 3H), 7.30 (d, J=8.2 Hz, 2H), 7.34 (s, 1H), 7.53 (d, J=8.2 Hz, 1H), 8.71 (s, 1H); MS m/z=211.4.

Step B: 3-[4-Chloro-2-(dibromomethyl)phenyl]-1,2,5-thiadiazole

A mixture of 3-(4-chloro-2-methylphenyl)-1,2,5-thiadiazole (0.278 g, 1.32 mmol), NBS (0.235 g, 1.32 mmol) and benzoyl peroxide (16.0 mg, 0.07 mmol) in carbon tetrachloride (5.0 mL) was refluxed for 1 h. More benzoyl peroxide (16.0 mg, 0.07 mmol) was added and the solution was refluxed for 16 h. More NBS (0.235 g, 1.32 mmol) and benzoyl peroxide (32.0 mg, 0.14 mmol) were added and the solution was refluxed for a further 16 h. The resulting suspension was filtered, rinsing with ether. The filtrate was washed with 10% aqueous sodium sulfite, saturated aqueous sodium bicarbonate and brine. The organic layer was separated, dried (Na₂SO₄) and reduced in vacuo. 3-[4-Chloro-2-(dibromomethyl)phenyl]-1,2,5-thiadiazole was isolated as a yellow solid. ¹H NMR (CDCl₃. 400 MHz) δ 7.42 (dd, J=2.1, 8.5 Hz, 1H), 7.49 (d, J=8.5 Hz, 1H), 7.53 (s, 1H), 8.20 (s, 1H), 8.80 (s, 1H); MS m/z=287.7.

Step C: 5-Chloro-2-(1,2,5-thiadiazol-3-yl)benzaldehyde

A stirred solution of 3-[4-chloro-2-(dibromomethyl)phenyl]-1,2,5-thiadiazole (0.452 g, 1.23 mmol) and potassium sulfate (0.334, 2.45 mmol) in concentrated $H_2SO_4$ (20.0 mL) was heated to 90° C. for 1.5 h. The solution was poured into ice water, basified with saturated aqueous sodium carbonate and extracted into EtOAc. The organic phase was dried ($Na_2SO_4$) and reduced in vacuo. 5-Chloro-2-(1,2,5-thiadiazol-3-yl)benzaldehyde was isolated as a solid. $^1$H NMR ($CDCl_3$, 400 MHz) δ 7.70 (s, 2H), 8.05 (s, 1H), 8.82 (s, 1H), 10.28 (s, 1H).

Step D: N-[5-Chloro-2-(1,2,5-thiadiazol-3-yl)benzyl]-N-(4-methoxybenzyl)amine

To a stirred solution of 5-chloro-2-(1,2,5-thiadiazol-3-yl)benzaldehyde (0.155 g, 0.69 mmol), 4-methoxybenzylamine (0.09 mL, 0.69 mmol) and acetic acid (0.05 mL, 0.83 mmol) in 1,2-dichloroethane (5.2 mL) was added sodium triacetoxyborohydride (0.731 g, 3.45 mmol). The solution was stirred at ambient temperature for 16 h then partitioned between $CH_2Cl_2$ and saturated aqueous sodium bicarbonate. The organic phase was dried ($Na_2SO_4$) and reduced in vacuo. The residue was purified by automated preparative chromatography on silica (eluting with 5% $CH_2Cl_2$/EtOAc/ hexanes gradient, 5–50% EtOAc). N-[5-Chloro-2-(1,2,5-thiadiazol-3-yl)benzyl]-N-(4-methoxybenzyl)amine was isolated as an oil. $^1$H NMR ($CDCl_3$, 400 MHz) δ 3.74 (s, 2H), 3.81 (s, 3H), 3.82 (s, 2H), 6.86 (d, J=8.6 Hz, 1H), 7.22 (d, J=8.4 Hz, 1H), 7.55 (d, J=8.4 Hz, 1H), 8.84 (s,1H); MS m/z=346.5.

Step E: 5-Chloro-2-(1.2,5-thiadiazol-3-yl)benzylammonium trifluoroacetate

To a stirred 0° C. solution of N-[5-chloro-2-(1,2,5-thiadiazol-3-yl)benzyl]-N-(4methoxybenzyl)amine (0.104 g, 0.30 mmol) in $CH_3CN$ (5.0 mL) was added a solution of CAN (0.990 g, 1.81 mmol) in water (10.0 mL). The solution was stirred at ambient temperature for 1 h then was partitioned between EtOAc and 10% aqueous $NH_4OH$. The resulting suspension was filtered, and the EtOAc layer was separated, washed with 10% sodium sulfite and brine, dried ($Na_2SO_4$) and reduced in vacuo. The resulting solid was purified by HPLC ($C_{18}$ eluting with an acetonitrile/water/ 0.1% TFA gradient). 5-Chloro-2-(1,2,5-thiadiazol-3-yl)benzylammonium trifluoroacetate was isolated as a solid. $^1$H NMR ($CD_3OD$, 400 MHz) δ 4.36 (s, 2H), 6.67 (dd, J=2.3, 8.3 Hz, 1H), 7.72 (s, 1H), 8.06 (d, J=8.4 Hz, 1H), 9.17 (s,1H); MS m/z=226.5.

Step F: 1-{(2R)-2-[(tert-Butoxycarbonyl)amino]-2-cyclohexylethanoyl}-N-[5-chloro-2-(1,2,5-thiadiazol-3-yl)benzyl]-L-prolinamide To a stirred solution of 5-chloro-2-(1,2,5-thiadiazol-3-yl) benzylammonium trifluoroacetate (40.9 mg, 0.13 mmol), 1-{(2R)-2-[(tert-butoxycarbonyl)amino]-2-cyclohexylethanoyl}-L-proline (prepared by standard peptide coupling protocols, 45.0 mg, 0.13 mmol), HOAt (22.5 mg, 0.17 mmol) and N-methylmorpholine (0.03 mL, 0.25 mmol) in DMF (0.5 mL) was added EDC (31.7 mg, 0.17 mmol). After 16 h the solution was partitioned between EtOAc and water. The organic phase was washed with brine, dried ($Na_2SO_4$) and reduced in vacuo. 1-{(2R)-2-[(tert-Butoxycarbonyl) amino]-2-cyclohexylethanoyl}-N-[5-chloro-2-(1,2,5-thiadiazol-3-yl)benzyl]-L-prolinamide was obtained as an oil. MS m/z=562.6.

Step G: 1-[(2R)-2-Amino-2-cyclohexylethanoyl]-N-[5-chloro-2-(1,2,5-thiadiazol-3-yl)benzyl]-L-prolinamide HCl gas was bubbled through a stirred 0° C. solution of 1-{(2R)-2-[(tert-butoxycarbonyl)amino]-2-cyclohexylethanoyl}-N-[5-chloro-2-(4-chloro-1,2,5-thiadiazol-3-yl)benzyl]-L-prolinamide (41.1 mg, 0.07 mmol) in $CH_2Cl_2$ (1.0 mL) for 15 min. The solution was reduced in vacuo. The resulting solid was triturated with EtOAc and filtered. 1-[(2R)-2-Amino-2-cyclohexylethanoyl]-N-[5-chloro-2-(1, 2,5-thiadiazol-3-yl)benzyl]-L-prolinamide hydrochloride was isolated as a solid. $^1$H NMR ($CD_3OD$ 400 MHz) δ 1.30 (m, 6H), 1.74 (m, 2H), 1.86 (m, 4H), 2.02 (m, 2H), 2.23 (m, 1H), 3.62 (m, 1H), 3.75 (m,1H), 3.98 (d, J=6.0 Hz, 1H), 4.42 (m, 1H), 4.64 (s, 2H), 7.46 (dd, J=2.2, 8.2 Hz, 1H), 7.62 (s, 1H), 7.74 (d, J=8.2 Hz, 1H), 8.99 (s, 1H): MS m/z=462.6.

EXAMPLE 54

Preparation of 1-[(2R)-2-Amino-2-cyclohexylethanoyl]-N-[5-chloro-2-(1,2,3-thiadiazol-4-yl)benzyl]-L-prolinamide

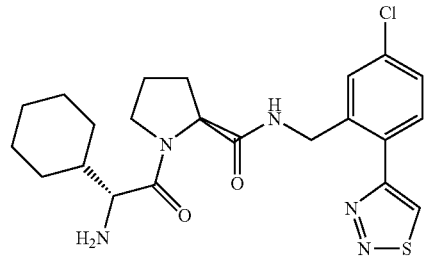

Step A: 1-(4-Chloro-2-methylphenyl)ethanone

Methylmagnesium bromide (6.29 g, 52.8 mmol) was added to a stirred solution of 4-chloro-2-methyl-benzonitrile (5.00 g, 33.0 mmol) in diethyl ether (44 mL). The mixture was heated to 40° C. After 72 h the mixture was cooled to room temperature and poured into a stirred mixture of anhydrous diethyl ether (120 mL), ice water (100 mL), and 10% aqueous HCl (100 mL). The aqueous layer was separated, stirred at reflux for 1 h, then was cooled to room temperature and was extracted into diethyl ether (4×50 mL). The organic layers were combined, washed with saturated $NaHCO_3$ and brine, dried ($Na_2SO_4$) and concentrated in vacuo. 1-(4-Chloro-2-methylphenyl)ethanone was obtained as an oil. $^1$H NMR ($CDCl_3$, 400 MHz) δ 2.52 (s, 3H), 2.56 (d, J=0.7 Hz, 3H), 7.24 (m, 2H), 7.65 (d, J=8.8 Hz, 1H).

Step B: Ethyl (2E)-2-[1-(4-chloro-2-methylphenyl)ethylidene]hydrazine carboxylate Ethyl carbazate (2.970 g, 28.53 mmol) and p-toluenesulfonic acid monohydrate (4.456 g, 28.53 mmol) were added to a stirred solution of 1-(4-chloro-2-methylphenyl) ethanone (4.81 g, 28.53 mmol) in toluene (50 mL). The mixture was heated to relux in a Dean-Stark apparatus. After 2 h the solution was evaporated and the viscous red-orange oil was purified by flash chromatography on silica (eluting with an EtOAc/hexanes gradient, 5–40% EtOAc). Ethyl (2E)-2-[1-(4-chloro-2-methylphenyl)ethylidene]hydrazine carboxylate was obtained as white crystals. MS m/z=255.6; $^1$H NMR ($CDCl_3$, 400 MHz) δ 1.34 (t, J=6.8 Hz, 3H), 2.20 (s, 3H), 2.35 (s, 3H), 4.31 (q, J=6.8 Hz, 2H), 7.19 (m, 3H), 7.72 (s, 1H).

Step C: 4-(4-Chloro-2-methylphenyl)-1,2,3-thiadiazole

Ethyl (2E)-2-[1-(4-chloro-2-methylphenyl)ethylidene] hydrazine carboxylate (0.63 g, 2.45 mmol) was stirred with thionyl chloride (1 mL, 13.70 mmol) at 60° C. for 1 h. The mixture was cooled to room temperature and concentrated in vacuo. 4-(4-Chloro-2-methylphenyl)-1,2,3-thiadiazole was obtained as a red solid. MS m/z=211.5; $^1$H NMR (CDCl$_3$, 400 MHz) δ 2.45 (s, 3H), 7.31 (dd, J=2.2, 8.2 Hz, 1H), 7.36 (d, J=1.8 Hz, 1H), 7.60 (d, J=8.2 Hz, 1H), 8.51 (s, 1H).

Step D: 4-[2-(Bromomethyl)-4-chlorophenyl]-1 2.3-thiadiazole

NBS (0.82 g, 5.62 mmol) and AIBN (0.077g, 0.47 mmol) were added to a stirred mixture of 4-(4-chloro-2-methylphenyl)-1,2,3-thiadiazole (0.82 g, 3.89 mmol) in CHCl$_3$ (82 mL) and the mixture was heated to reflux. After 16 h more AIBN (0.154 g, 0.94 mmol) and NBS (0.82 g, 5.62 mmol) were added and after a further 2 h, the mixture was cooled to room temperature, diluted with CHCl$_3$ and washed with water, 5% sodium thiosulfate and brine, dried, (Na$_2$SO$_4$) and concentrated in vacuo. The product was purified by flash chromatography on silica (eluting with an EtOAc/hexanes gradient, 1–20% EtOAc) to give a pale yellow solid which was carried forward to the next step.

Step E: 4-[2-(Azidomethyl)-4-chlorophenyl]-1,2,3-thiadiazole

Sodium azide (0.56 g, 8.61 mmol) was added to a stirred solution of the product of Step D in DMF (22 mL). After 16 h the mixture was partitioned between EtOAc and water. The organic layer was washed with brine, dried (Na$_2$SO$_4$) and concentrated in vacuo. The product was purified by flash chromatography on silica (eluting with an EtOAc/hexanes gradient, 1–10% EtOAc) to give a pale yellow solid which was carried forward to the next step.

Step F: 1-[5-chloro-2-(1,2,3-thiadiazol-4-yl)phenyl]methanamine

Triphenylphosphine (0.390 g, 1.49 mmol) and deionized water (0.02 mL, 1.18 mmol) were added to a stirred solution of the product from Step E in anhydrous THF (8.8 mL). After 16 h the mixture was concentrated in vacuo and the residue was purified by flash chromatography on silica (eluting with chloroform/10% NH$_4$OH, MeOH). 1-[5-Chloro-2-(1,2,3-thiadiazole-4-phenyl]methanamine was obtained as an orange glass. MS m/z=226.5; $^1$H NMR (CDCl$_3$, 400 MHz), δ 3.87 (s, 2H), 7.39 (dd, J=2.0, 8.2 Hz, 1H), 7.57 (d, J=2.0 Hz, 1H), 7.61 (d, J=8.2 Hz, 1H), 8.87 (s, 1H).

Step G: 1-{(2R)-2-[(tert-Butoxycarbonyl)amino]-2-cyclohexylethanoyl}-N-[5-chloro-2-(1,2,3-thiadiazol-4-yl)benzyl]-L-prolinamide EDC (0.388 g, 2.02 mmol), HOAt (0.275 g, 2.02 mmol), and 1-{(2R)-2-[(tert-butoxycarbonyl)amino]-2-cyclohexylethanoyl}-L-proline (prepared by standard peptide coupling protocols, 0.551 g, 1.55 mol) were added to a stirred solution of 1-[5-Chloro-2-(1,2,3-thiadiazol-4-yl)phenyl]methanamine (0.351 g, 1.555 mmol) in DMF (7.8 mL). After 16 h the mixture was partitioned between EtOAc and water. The organic layer was washed with brine, dried (Na$_2$SO4) and concentrated in vacuo. The product was purified by flash chromatography on silica (eluting with an EtOAc/hexanes gradient, 1–100% EtOAc). 1-{(2R)-2-[(tert-Butoxycarbonyl)amino]-2-cyclohexylethanoyl}-N-[5-chloro-2-(1,2,3-thiadiazol-4-yl)benzyl]-L-prolinamide was obtained as a solid. MS m/z=562.6.

Step H: 1-[(2R)-2-Amino-2-cyclohexylethanoyl]-N-[5-chloro-2-(1,2,3-thiadiazol-4-yl)benzyl]-L-prolinamide HCl gas was bubbled through a stirred solution of 1-{(2R)-2-[(tert-butoxycarbonyl)amino]-2-cyclohexylethanoyl}-N-[5-chloro-2-(1,2,3-thiadiazol-4-yl)benzyl]-L-prolinamide (0.25 g, 0.445 mmol) in CH$_2$Cl$_2$ at 0° C. After 15 min the solution was degassed with nitrogen and was concentrated in vacuo. The residue was purified by reverse phase HPLC (C$_{18}$, eluting with acetonitrile/0.1% TFA/water gradient). 1-[(2R)-2-Amino-2-cyclohexylethanoyl]-N-[5-chloro-2-(1,2,3-thiadiazol-4-yl)benzyl]prolinamide was obtained as the TFA salt as a glass. MS m/z=462.6; $^1$H NMR (CD$_3$OD, 400 MHz), δ 1.22 (m, 5H), 1.74 (m, 2H), 1.85 (m, 5H), 1.99 (m, 2H), 2.22 (m, 1H), 3.68 (m, 1H), 3.76 (m, 1H), 3.99 (d, J=7.0 Hz, 1H), 4.42 (dd, J=3.8, 8.6 Hz, 1H), 4.48 (d, J=15.5 Hz, 1H), 4.55 (d, J=15.5 Hz, 1H), 7.45 (dd, J=2.2, 8.3 Hz, 1H), 7.63 (s, 1H), 7.64 (d, J=8.3 Hz, 2H), 9.16 (s, 1H).

EXAMPLE 55

Preparation of 4-methyl-D-leucyl-N-[5-chloro-2-(1H-tetraazol-1-yl)benzyl]-L-azetidinamide

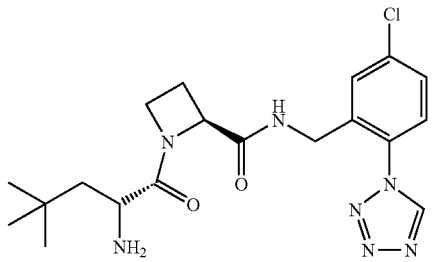

Step A: tert-Butyl(2S)-2-({[5-chloro-2-(1H-tetraazol-1-yl)benzyl]amino}carbonyl)azetidine-1-carboxylate The title compound was prepared from (2S)-1-(tert-butoxycarbonyl)azetidine-2-carboxylic acid (240 mg, 1.19 mmol) and N-5-chloro-2-(1H-tetraazol-1-yl)benzylamine (250 mg, 1.19 mmol) essentially according to the EDC coupling procedure described in Example 26, Step B (omitting the HCl deprotection step). Water and saturated aqueous K$_2$CO$_3$ were added to the mixture. The aqueous layer was extracted with EtOAc. The organic layer was washed with brine. The combined aqueous layers were extracted with CH$_2$Cl$_2$. The combined organic extracts were dried over Na$_2$SO$_4$, and concentrated to a yellow oil. Silica gel chromatography (50%–80% EtOAc/hexanes) afforded the title compound as a yellow oil. LCMS (M+H): 393.1. $^1$H NMR (CDCl$_3$, 400 MHz): δ 9.02 (s, 1 H), 7.62 (d, J=2.0 Hz, 1 H), 7.45 (dd, J=2.4 Hz, 8.4 Hz, 1 H), 7.18–7.14 (m, 1 H), 4.65 (apparent t, J=8.2 Hz, 1 H), 4.33–4.28 (m, 1H), 4.23–4.18 (m, 1 H), 3.91 (m, 1 H), 3.82–3.78 (m, 1 H), 2.46–2.35 (m, 2 H), 1.45 (s, 9 H).

Step B: 4-[2-({[(2S)-azetidinium-2-ylcarbonyl]amino}methyl)-4-chlorophenyl]-4H-tetraazol-1-ium dichloride Through a solution of tert-butyl (2S)-2-({[5-chloro-2-(1H-tetraazol-1-yl)benzyl]amino}carbonyl)azetidine-1-carboxylate (467 mg, 1.19 mmol) in EtOAc (24.0 mmol) at 0° C. was bubbled HCl (g) for 10 min. The solvent was removed in vacuo to give the title compound as a yellow solid. LCMS (M+H): 293.0. $^1$H NMR (CD$_3$OD, 400 MHz):

δ 9.57 (s, 1 H), 7.72–7.70 (m, 1 H), 7.64–7.59 (m, 1 H), 7.54–7.52 (m, 1 H), 4.96–4.92 (m, 1 H), 4.34–4.21 (m, 2 H), 4.13–4.06 (m, 1 H), 3.97–3.90 (m, 1 H), 2.81–2.75 (m, 1 H), 2.51–2.45 (m, 1 H).

Step C: $N^1$-tert-Butoxycarbonyl-4-methyl-D-leucyl-$N^2$-[5-chloro-2-1H-tetraazol-1-yl)benzyl]-L-azetidinamide The title compound was prepared from 4-[2-({[(2S)-azetidinium-2-ylcarbonyl]amino}methyl)-4-chlorophenyl]-4H-tetraazol-1-ium dichloride (44 mg, 0.12 mmol) and Boc-D-t-Bu-Ala (29 mg, 0.12 mmol) essentially according to the EDC coupling procedure described in Example 39, Step D. The reaction mixture was purified by reverse phase HPLC to afford a foamy white solid which was carried on directly to deprotection. LCMS (M+H): 520.3.

Step D: 4-methyl-D-leucyl-N-[5-chloro-2-1H-tetraazol-1-yl)benzyl]-L-azetidinamide $N^1$-tert-butoxycarbonyl-4-methyl-D-leucyl-$N^2$-[5-chloro-2-1H-tetraazol-1-yl)benzyl]-L-azetidinamide was taken up in 2.0 mL of $CH_2Cl_2$ and TFA (1.0 mL) was added in excess. The solvent was removed in vacuo and the residual oil was purified by reverse phase HPLC to afford the TFA salt of the title compound as a white foamy solid. LCMS (M+H): 420.1. $^1$H NMR ($CD_3OD$, 400 MHz): δ 9.54 (s, 1 H), 7.73 (d, J=2 Hz, 1 H), 7.60–7.51 (m, 2 H), 4.71–4.67 (m, 1 H), 4.42–4.24 (m, 4 H), 3.91–3.88 (m, 1 H), 2.61–2.57 (m, 1 H), 2.29–2.24 (m, 1 H), 1.99–1.92 (m, 1 H), 1.64–1.59 (m, 1H), 1.01 (s, 9 H).

EXAMPLE 56

Preparation of 4-methyl-D-leucyl-N-[5-chloro-2-(1H-tetraazol-1-yl)benzyl]-L-piperidinamide

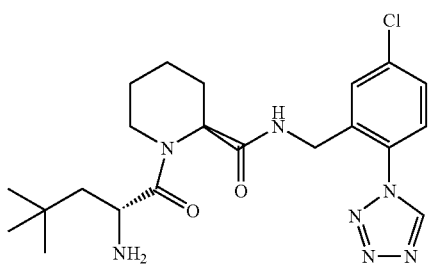

Step A: tert-Butyl (2S)-2-({[5-chloro-2-(1H-tetraazol-1-yl)benzyl]amino}carbonyl)piperidine-1-carboxylate A mixture of (2S)-1-(tert-butoxycarbonyl)piperidine-2-carboxylic acid (299 mg, 1.30 mmol), 1-[5-chloro-2-(1H-tetraazol-1-yl)phenyl]methanamine (293 mg, 1.40 mmol), EDC (376 mg, 1.96 mmol) and HOAt (89 mg, 0.65 mmol) in DMF (7 mL) was stirred at room temperature for 16 h. Water and saturated aqueous $K_2CO_3$ were added and the mixture was extracted with EtOAc. The organic layer was washed with brine and the combined aqueous layers were extracted once with $CH_2Cl_2$. The combined organic extracts were dried ($Na_2SO_4$) and concentrated to a yellow oil. Silica gel chromatography (65% EtOAc-hexanes) afforded the title compound as a light yellow foam. $^1$H NMR (400 MHz, $CDCl_3$): δ 8.99 (s, 1 H), 7.60 (d, J=1.8 Hz, 1 H), 7.46 (dd, J=1.8, 8.4 Hz, 1 H), 7.29–7.26 (m, 1 H), 6.84 (br m, 1 H), 4.74 (br m, 1 H), 4.29–4.16 (m, 2 H), 4.04 (br m, 1 H), 2.76–2.70 (m, 1 H), 2.24–2.04 (m, 1 H), 1.64–1.32 (br m, 5 H), 1.48 (s, 9 H).

Step B: (2S)-N-[5-chloro-2-(1H-tetraazol-1-yl)benzyl]piperidine-2-carboxamide

HCl gas was bubbled through a cold (0° C.) solution of tert-butyl (2S)-2-({[5-chloro-2-(1H-tetraazol-1-yl)benzyl]amino}carbonyl)piperidine-1-carboxylate (506 mg, 1.20 mmol) in EtOAc (24 mL) for 5 min. The mixture was stirred at 0° C. for 15 min and the solvent was removed in vacuo. Repeated concentration from $Et_2O$ afforded the hydrochloride salt of the title compound as a light yellow foam. $^1$H NMR (400 MHz, $CD_3OD$): δ 9.58 (s, 1 H), 8.71 (br m, 1 H), 7.67 (d, J=2.4 Hz, 1 H), 7.60–7.51 (m, 2 H), 4.34–4.24 (m, 2 H), 3.78 (br m, 1 H), 3.39–3.36 (m, 1 H), 3.03–2.97 (m, 1 H), 2.16–2.13 (m, 1 H), 2.00–1.85 (m, 2 H), 1.70–1.60 (m, 3 H).

Step C: 4-methyl-D-leucyl-N-[5-chloro-2-(1H-tetraazol-1-yl)benzyl]-L-piperidinamide The title compound was prepared from (2S)-N-[5-chloro-2-(1H-tetraazol-1-yl)benzyl]piperidine-2-carboxamide and Boc-D-t-Bu-Ala essentially according to the coupling procedure described in Example 39, Step D followed by the deprotection procedure described in Example 55, Step D. Purification of the crude product by reverse phase HPLC gave the TFA salt of the title compound as a foamy white solid. LCMS (M+H): 448.2. $^1$H NMR ($CD_3O$, 400 MHz): δ 9.54 (s, 1 H), 8.43 (m, 1 H), 7.65 (d, J=2.0 Hz, 1 H), 7.57 (dd, J=2.0 Hz, 8.4Hz, 1 H), 7.50 (d, J=8.4 Hz, 1 H), 4.98–4.97 (m, 1 H), 4.47–4.44 (m, 1 H), 4.28 (app d, J=3.6 Hz, 2 H), 3.76–3.73 (m, 1 H), 3.50–3.39 (m, 1 H), 2.12–2.09 (m, 1 H), 1.87–1.70 (m, 5 H), 1.56–1.53 (m, 1 H), 1.46–1.40 (m, 1 H), 1.04 (s,9 H).

EXAMPLE 57

Preparation of 4-methyl-D-leucyl-$N^1$-[5-chloro-2-(1H-tetraazol-1-yl)benzyl]-$N^2$-cyclopropylglycinamide

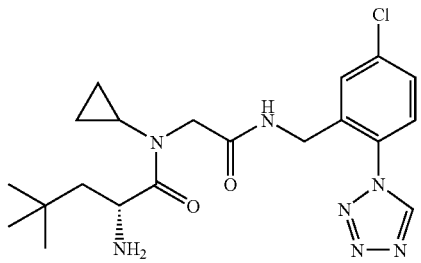

Step A: 2-Bromo-N-[5-chloro-2-(1H-tetraazol-1-yl)benzyl]acetamide

To a stirred solution of 1-[5-chloro-2-(1H-tetraazol-1-yl)phenyl]methanamine (150 mg, 0.72 mmol) and Hünig's base (137 μL, 0.79 mmol) in anhydrous THF (3.3 mL) at 0° C. was added dropwise bromoacetyl bromide (69 μL, 0.79 mmol). The resulting orange-yellow suspension was stirred under $N_2$ atmosphere at 0° C. for 20 min. The mixture was diluted with EtOAc and washed twice with $H_2O$, twice with saturated aqueous $NaHCO_3$ and once with brine. The organic layer was dried (anhydrous $Na_2SO_4$), filtered and concentrated to a brown oil. Silica gel chromatography (70% EtOAc-hexanes) afforded the title compound as a yellow oil which slowly formed a tan foam after drying in vacuo. $^1$H NMR (400 MHz, $CDCl_3$): δ 8.95 (s, 1 H), 7.70 (d, J=2.2 Hz, 1 H), 7.50 (dd, J=2.0, 8.4 Hz, 1 H), 7.30 (d, J=8.4 Hz, 1 H), 7.21 (br s, 1 H), 4.29 (d, J=6.4 Hz, 2 H), 3.88 (s, 2 H).

Step B: N¹-[5-chloro-2-(1H-tetraazol-1-yl)benzyl]-N²-cyclopropylglycinamide

To a stirred solution of 2-bromo-N-[5-chloro-2-(1H-tetraazol-1-yl)benzyl]acetamide (206 mg, 0.62 mmol) in CH$_2$Cl$_2$ (2.5 mL) at room temperature was added cyclopropylamine (500 μL, 7.22 mmol). The resulting yellow solution was stirred under N$_2$ atmosphere for 1 h. The solvent was removed in vacuo and the residue was purified by silica gel chromatography (gradient elution with EtOAc then with 10% MeOH-EtOAc) to afford the title compound as a yellow solid after drying in vacuo. ¹H NMR (400 MHz, CDCl$_3$): δ 8.97 (s, 1 H), 7.62–7.58 (m, 2 H), 7.46 (dd, J=1.8, 8.6 Hz, 1 H), 7.29–7.27 (m, 1 H), 4.24 (d, J=6.4 Hz, 2 H), 3.37 (s, 2 H), 2.23–2.18 (m, 1 H), 1.63 (br m, 1 H), 0.49–0.40 (m, 2 H), 0.37–0.36 (m, 2 H).

Step C: N-(tert-butoxycarbonyl)-4-methyl-D-leucyl-N¹-[5-chloro-2-(1H-tetraazol-1-yl)benzyl]-N²-cyclopropylglycinamide A mixture of N¹-[5-chloro-2-(1H-tetraazol-1-yl)benzyl]-N²-cyclopropylglycinamide (50 mg, 0.16 mmol), N-(tert-butoxycarbonyl)-4-methyl-D-leucine (42 mg, 0.17 mmol), EDC (49 mg, 0.26 mmol) and HOAt (16 mg, 0.12 mmol) in DMF (1.4 mL) was stirred for 16 h at room temperature. The title compound was isolated by reverse phase HPLC as a white foam and was carried on directly to deprotection. LCMS (M+H): 534.1.

Step D: 4-methyl-D-leucyl-N¹-[5-chloro-2-(1H-tetraazol-1-yl)benzyl]-N²-cyclopropylglycinamide TFA (3 mL) was added to a solution of N-(tert-butoxycarbonyl)-4-methyl-D-leucyl-N¹-[5-chloro-2-(1H-tetraazol-1-yl)benzyl]-N²-cyclopropylglycinamide (80 mg, 0.15 mmol) in CH$_2$Cl$_2$ (6 mL). The solution was stirred at room temperature for 30 min and the solvent was then removed in vacuo. The residue was taken up in DMF and purified by reverse phase HPLC. The product fractions were combined and reduced in vacuo and the residual oil was concentrated repeatedly from Et$_2$O to give the title compound as a white foam. ¹H NMR (500 MHz, CD$_3$O): δ 9.52 (s, 1 H), 8.50 (m, 1 H), 7.68 (d, J=2.5 Hz, 1 H), 7.57 (dd, J=2.5, 8.5 Hz, 1 H), 7.50 (d, J=8.0 Hz, 1 H), 4.72 (dd, J=3.5, 8.5 Hz, 1 H), 4.28 (d, J=16.0 Hz, 1 H), 4.24 (d, J=15.5 Hz, 1 H), 4.10 (d, J=16.0 Hz, 1 H), 3.99 (d, J=16.0 Hz, 1 H), 2.91–2.86 (m, 1 H), 2.02 (dd, J=3.5, 15.5 Hz, 1 H), 1.70 (dd, J=8.5, 15.0 Hz, 1 H), 1.06 (s, 9 H), 1.03–0.86 (m, 4 H). HRMS (APCI, M+H): 434.2055 (found); 434.2066 (calculated).

EXAMPLE 58

Preparation of N¹-[(1S)-1-({[5-chloro-2-(1H-1,2,4-triazol-1-yl)benzyl]amino}-carbonyl)propyl]-4-methyl-D-leucinamide

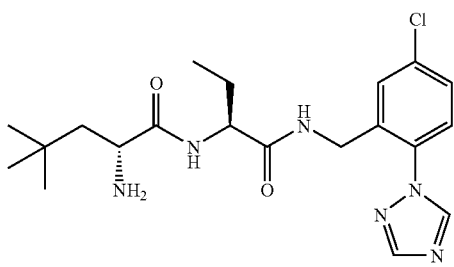

Step A: tert-Butyl(1S)-1-({[5-chloro-2-(1H-1,2,4-triazol-1-yl)benzyl]amino}carbonyl)propylcarbamate The title compound was prepared from N-Boc-L-α-aminobutyric acid (107 mg, 0.53 mmol) and 1-[5-chloro-2-(1H-1,2,4-triazol-1-yl)phenyl]methanamine (111 mg, 0.53 mmol) essentially according to the EDC coupling procedure described in Example 56, Step A. Silica gel chromatography (50%-80% EtOAc/hexanes) afforded a pale yellow oil. LCMS (M+H): 394.1. ¹H NMR (400 MHz, CD$_3$O): δ 8.80 (s, 1 H), 8.21 (s, 1 H), 7.62 (s, 1 H), 7.48–7.42 (m, 2 H), 4.33–4.23 (m, 2 H), 3.91–3.88 (m, 1 H), 1.78–1.72 (m, 1 H), 1.63–1.56 (m, 1 H), 1.44 (s, 9 H), 0.94 (t, J=7.4Hz,3 H).

Step B: (2S)-2-amino-N-[5-chloro-2-(1H-1,2,4-triazol-1-yl)benzyl]butanamide

To a stirred solution of tert-butyl (1S)-1-({[5-chloro-2-(1H-1,2,4-triazol-1-yl)benzyl]amino}carbonyl)propylcarbamate (208 mg, 0.53 mmol) in 2.6 mL of EtOAc was added 4 M HCl in dioxane (0.5 mL, excess) and the mixture stirred overnight at rt. Solvent was removed in vacuo to give the hydrochloride salt of the title compound as a white foamy solid. LCMS (M+H): 294.0. ¹H NMR (400 MHz, CD$_3$OD): δ 9.44 (s, 1 H), 8.62 (s, 1 H), 7.65 (s, 1 H), 7.55 (m, 2 H), 4.40–4.39 (m, 2 H), 3.83 (app t, J=6.2 Hz, 1 H), 1.89–1.83 (m, 2 H), 0.98 (t, J=7.4 Hz, 3 H).

Step C: N²-(tert-butoxycarbonyl)-N¹-[(1S)-1-({[5-chloro-2-(1H-1,2,4-triazol-1-yl)benzyl]amino}carbonyl)propyl]-4-methyl-D-leucinamide A mixture of Boc-D-t-butyl-alanine (49 mg, 0.20 mmol), (2S)-2-amino-N-[5-chloro-2-(1H-1,2,4-triazol-1-yl)benzyl]butanamide (66 mg, 0.20 mg), HOAt (27 mg, 0.20 mmol), EDC (57 mg, 0.30 mmol), and Et$_3$N (28 μL, 0.20 mmol) in 1.0 mL of DMF was stirred at rt overnight. A small amount of MeOH was used to aid in dissolution. Solvent was removed in vacuo to give the title compound, which was carried on directly to deprotection. LCMS (M+H): 521.2.

Step D: N¹-[(1S)-1-({[5-chloro-2-(1H-1,2,4-triazol-1-yl)benzyl]amino}carbonyl)propyl]-4-methyl-D-leucinamide To a stirred solution of N²-(tert-butoxycarbonyl)-N¹-[(1S)-1-({[5-chloro-2-(1H-1,2,4-triazol-1-yl)benzyl]amino}carbonyl)propyl]-4-methyl-D-leucinamide (104 mg, 0.20 mmol) in 1.0 mL CH$_2$Cl$_2$ at rt was added TFA (0.5 mL, excess) and the mixture allowed to stir overnight. Solvent was removed in vacuo and the remaining yellow oil was purified by reverse phase HPLC to afford the TFA salt of the title compound as a white solid. LCMS (M+H): 421.2. ¹H NMR (400 MHz, CD$_3$OD): δ 8.78 (s, 1 H), 8.22 (s, 1 H), 7.62 (d, J=2.0 Hz, 1 H), 7.51 (dd, J=2.0 Hz, 8.4 Hz, 1 H), 7.45 (d, J=8.4 Hz, 1 H), 4.40 (d, J=15.6 Hz, 1 H), 4.24 (d, J=15.6 Hz, 1 H), 4.13–4.10 (m, 1 H), 3.87 (dd, J=4.0 Hz, 9.2 Hz, 1 H), 2.03–1.98 (m, 1 H), 1.76–1.69 (m, 2 H), 1.56 (dd, J=4.4 Hz, 14.0 Hz, 1 H), 0.99 (s, 9 H), 0.97 (t, J=7.4 Hz, 3 H).

EXAMPLE 59

Preparation of N$^1$-[(1S)-1-({[5-chloro-2-(1H-tetraazol-1-yl)benzyl]amino}carbonyl)propyl]-4-methyl-D-leucinamide

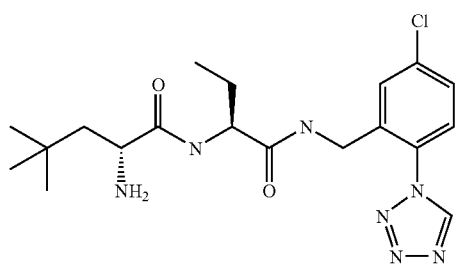

Step A: tert-butyl(1S)-1-({[5-chloro-2-(1H-tetraazol-1-yl)benzyl]amino}carbonyl)propylcarbamate The title compound was prepared from IV-Boc-L-α-aminobutyric acid (122 mg, 0.60 mmol) and 1-[5-chloro-2-(1H-tetraazol-1-yl)phenyl]methanamine (126 mg, 0.60 mmol) essentially according to the EDC coupling procedure described in Example 56, Step A. Silica gel chromatography (50% EtOAc/hexanes) afforded the title compound as a colorless oil. LCMS (M+H): 394.9. $^1$H NMR (400 MHz, CD$_3$OD): δ 9.54 (s, 1 H), 7.68 (s, 1 H), 7.54–7.46 (m, 2 H), 4.20 (app s, 2 H), 3.88–3.86 (m, 1 H), 1.76–1.67 (m, 1 H), 1.64–1.53 (m, 1 H), 1.44 (s, 9 H), 0.93 (t, J=7.4 Hz, 3 H).

Step B: (2S)-2-amino-N-[5-chloro-2-(1H-tetraazol-1-yl)benzyl]butanamide

To a stirred solution of tert-butyl (1S)-1-({[5-chloro-2-(1H-tetraazol-1-yl)benzyl]amino}carbonyl)propylcarbamate (237 mg, 0.60 mmol) in EtOAc (3.5 mL) at rt was added 4 M HCl in dioxane (0.6 mL, excess). After 30 min, a small amount of MeOH was added to keep product in solution. After 3 h, another 0.6 mL of 4 M HCl/dioxane was added and continued to stir overnight at rt. Solvent was removed in vacuo to give the title compound as a foamy yellow solid. LCMS (M+H): 295.0. $^1$H NMR (400 MHz, CD$_3$OD): δ 9.58 (s, 1 H), 8.79 (m, 1 H), 7.68 (d, J=2.4 Hz, 1 H), 7.58 (dd, J=2.0 Hz, 8.4 Hz, 1 H), 7.52 (d, J=8.4 Hz, 1 H), 4.30–4.29 (m, 2 H), 3.79 (app t, J=6.2 Hz, 1 H), 1.87–1.80 (m, 2 H), 0.97 (t, J=7.6 Hz, 3 H).

Step C. N$^2$-(tert-butoxycarbonyl)-N$^1$-[(1S)-1-({[5-chloro-2-(1H-tetraazol-1-yl)benzyl]amino}carbonyl)propyl]-4-methyl-D-leucinamide A mixture of Boc-D-tert-butyl-alanine (74 mg, 0.30 mmol), (2S)-2-amino-N-[5-chloro-2-(1H-tetraazol-1-yl)benzyl]butanamide (99 mg, 0.30 mmol), HOAt (41 mg, 0.30 mmol), EDC (86 mg, 0.45 mmol), and Et$_3$N (42 µL, 0.30 mmol) in DMF (1.0 mL) was stirred at rt overnight. A small amount of MeOH was added to aid in dissolution. Solvent was removed in vacuo to give the title compound, which was carried on directly to deprotection. LCMS (M+H): 522.0.

Step D: N$^1$-[(1S)-1-({[5-chloro-2-(1H-tetraazol-1-yl)benzyl]amino}carbonyl)propyl]-4-methyl-D-leucinamide To a stirred solution of N$^2$-(tert-butoxycarbonyl)-N$^1$-[(1S)-1-({[5-chloro-2-(1H-tetraazol-1-yl)benzyl]amino}carbonyl)propyl]-4-methyl-D-leucinamide in CH$_2$Cl$_2$ (1.0 mL) at 0° C. was added TFA (1.0 mL, excess). The reaction was allowed to warm to rt while stirring overnight. Solvent was removed in vacuo. The remaining residue was taken up in DMF and purified by reverse phase HPLC to afford the TFA salt of the title compound as a yellow solid. LCMS (M+H): 422.0. $^1$H NMR (400 MHz, CD$_3$OD): δ 9.53 (s, 1 H), 7.69 (d, J=2.4 Hz, 1 H), 7.57 (dd, J=2.4 Hz, 8.4 Hz, 1 H), 7.50 (d, J=8.8 Hz, 1 H), 4.33 (d, J=15.6 Hz, 1 H), 4.20 (d, J=15.6 Hz, 1 H), 4.07 (dd, J=5.8 Hz, 8.8 Hz, 1 H), 3.87 (dd, J=4.0 Hz, 9.2 Hz, 1 H), 2.00 (dd, J=9.0 Hz, 14.4 Hz, 1 H), 1.75–1.67 (m, 2 H), 1.56 (dd, J=4.0 Hz, 14.0 Hz, 1 H), 0.99 (s, 9 H), 0.95 (t, J=7.4 Hz, 3 H).

EXAMPLE 60

Preparation of 4-methyl-D-leucyl-N$^1$-[5-chloro-2-(1H-1,2,4-triazol-1-yl)benzyl]-L-valinamide

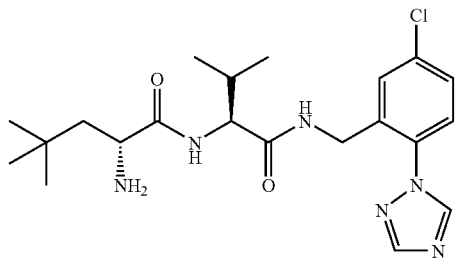

The title compound was prepared essentially according to the procedures described in Example 58, starting from Boc-L-valine. $^1$H NMR (300 MHz, CD$_3$OD): δ 8.78 (s, 1 H), 8.21 (s, 1 H), 7.65 (d, J=2.4 Hz, 1 H), 7.51 (dd, J=2.1, 8.4 Hz, 1 H), 7.46 (d, J=8.7 Hz, 1 H), 4.41 (d, J=15.3 Hz, 1 H), 4.23 (d, J=15.6 Hz, 1 H), 4.01 (d, J=6.9 Hz, 1 H), 3.94 (dd, J=4.2, 8.4 Hz, 1 H), 2.05–1.97 (m, 2 H), 1.57 (dd, J=4.5, 14.1 Hz, 1 H), 1.00 (s, 9 H), 0.97 (d, J=7.2 Hz, 3 H), 0.94 (d, J=7.2 Hz, 3 H). HRMS (FAB) M+H: calculated for (C$_{21}$H$_{31}$N$_6$O$_2$Cl)$^+$ 435.2197, found 435.2271.

EXAMPLE 61

HPLC Conditions

HPLC methods are defined as follows:

| Method A or X: | |
| --- | --- |
| Stationary Phase: | Hewlett-Packard Zorbax SB-C8 column<br>75 × 4.6 mm, 3.5 micron |
| Mobile Phase: | A = H$_2$O containing 0.1% by volume TFA<br>B = CH$_3$CN containing 0.1% by volume TFA<br>Gradient: 95:5 A:B to 0:100 A:B over 4.5 minutes<br>Flow Rate: 3.0 mL/min |
| UV Detection at 215 nm | |
| Method B: | |
| Stationary Phase: | Waters Xterra RP18 column<br>50 × 4.6 mm, 3.5 micron |
| Mobile Phase: | A = H$_2$O containing 0.1% by volume H$_3$PO$_4$<br>B = CH$_3$CN<br>Gradient: 95:5 A:B to 5:95 A:B over 4.0 minutes<br>Flow Rate: 4.0 mL/min |
| UV Detection at 215 nm | |

Typical tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

In Vitro Assay for Determining Proteinase Inhibition

Assays of human α-thrombin and human trypsin were performed by the methods substantially as described in Thrombosis Research, Issue No. 70, page 173 (1993) by S. D. Lewis et al.

The assays were carried out at 25° C. in 0.05 M TRIS buffer pH 7.4, 0.15 M NaCl, 0.1% PEG. Trypsin assays also contained 1 mM $CaCl_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin ($K_m$=125 μM) and bovine trypsin ($K_m$=125 μM). p-Nitroanilide substrate concentration was determined from measurements of absorbance at 342 nm using an extinction coefficient of 8270 $cm^{-1}M^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≦0.1 Km into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [1], and e respectively represent the total concentrations, of substrate, inhibitor and enzyme), the equilibrium constant ($K_i$) for dissociation of the inhibitor from the enzyme can be obtained from the dependence of $V_{o/Vi}$ on [I1] shown in the following equation.

$$V_o/V_i = 1 + [I]/K_i$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

EXAMPLE 62

Tablet Preparation

Tablets containing 25.0, 50.0, and 100.0 mg., respectively, of the following active compounds are prepared as illustrated below (compositions A-C). Active I is compound D-Phenylalanyl-N-[2-(1H-tetraazol-1-yl)benzyl]-L-prolinamide hydrochloride.

| Component | Amount-(mg) | | |
|---|---|---|---|
| | A | B | C |
| Active I | 25 | 50 | 100 |
| Microcrystalline cellulose | 37.25 | 100 | 200 |
| Modified food corn starch | 37.25 | 4.25 | 8.5 |
| Magnesium stearate | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 63

Tablet Preparation

Exemplary compositions of compound D-Phenylalanyl-N-[2-(1H-tetraazol-1-yl)benzyl]-L-prolinamide hydrochloride (Active I) tablets are shown below:

| Component | 0.25 mg | 2 mg | 10 mg | 50 mg |
|---|---|---|---|---|
| Active I | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet Preparation Via Direct Compression

Active I, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation Via Dry Granulation

Alternatively, a dry powder blend is compacted under modest forces and remilled to afford granules of specified particle size. The granules are then mixed with magnesium stearate and tabletted as stated above.

EXAMPLE 64

Intravenous Formulations

Intravenous formulations of compound D-Phenylalanyl-N-[2-(1H-tetraazol-1-yl)benzyl]-L-prolinamide hydrochloride (Active I) were prepared according to general intravenous formulation procedures.

| Component | Estimated range |
|---|---|
| Active I | 0.12–0.61 mg |
| D-glucuronic acid* | 0.5–5 mg |
| Mannitol NF | 50–53 mg |
| 1 N Sodium Hydroxide | q.s. pH 3.9–4.1 |
| Water for injection | q.s. 1.0 mL |

Exemplary compositions A–C are as follows:

| Component | A | B | C |
|---|---|---|---|
| Active I | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1 N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base
**0.25 mg free base
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound of the general formula,

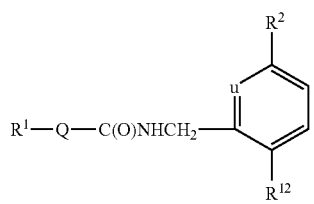

wherein
u is CH or N;
Q is
1) —N(R$^{25}$)CH(R$^{30}$)—
   wherein
   the nitrogen atom is attached to R$^1$, and
   R$^{25}$ and R$^{30}$ are independently selected from the group consisting of hydrogen, C$_{3-6}$cycloalkyl, and C$_{1-6}$alkyl, or

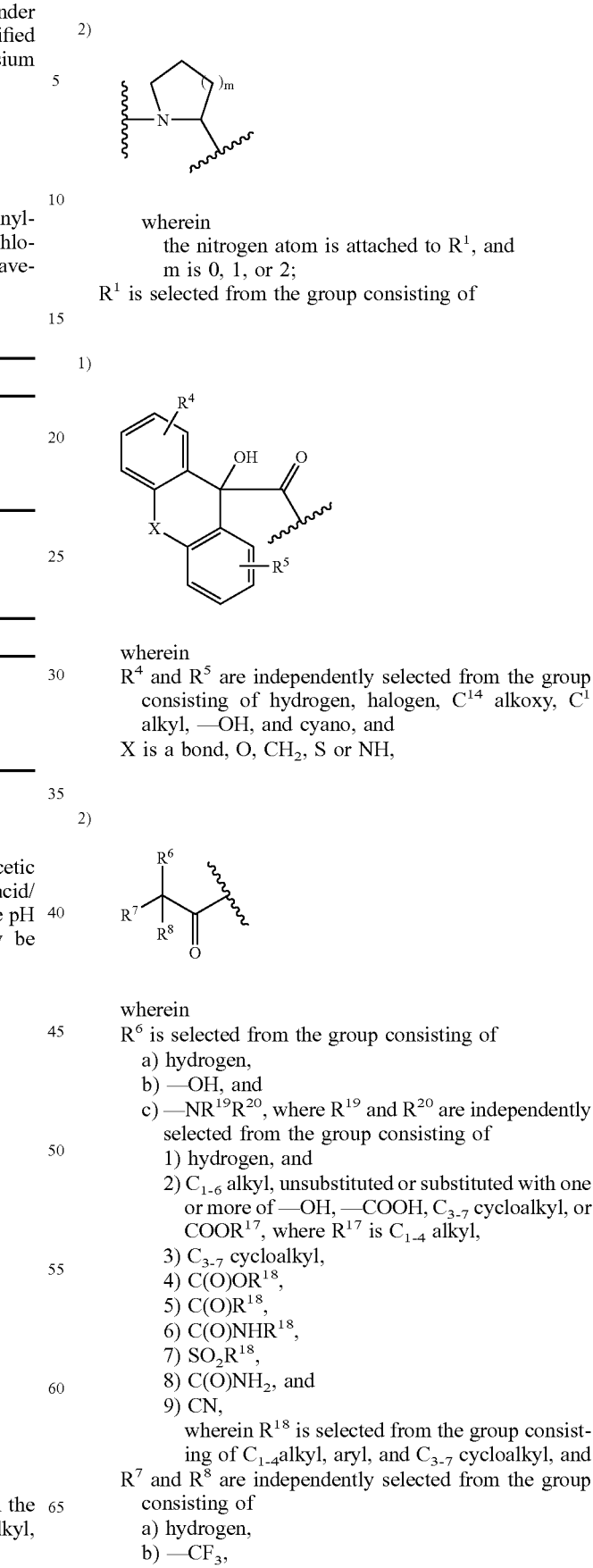

wherein
the nitrogen atom is attached to R$^1$, and
m is 0, 1, or 2;
R$^1$ is selected from the group consisting of

1)

wherein
R$^4$ and R$^5$ are independently selected from the group consisting of hydrogen, halogen, C$^{14}$ alkoxy, C$^1$ alkyl, —OH, and cyano, and
X is a bond, O, CH$_2$, S or NH,

2)

wherein
R$^6$ is selected from the group consisting of
a) hydrogen,
b) —OH, and
c) —NR$^{19}$R$^{20}$, where R$^{19}$ and R$^{20}$ are independently selected from the group consisting of
1) hydrogen, and
2) C$_{1-6}$ alkyl, unsubstituted or substituted with one or more of —OH, —COOH, C$_{3-7}$ cycloalkyl, or COOR$^{17}$, where R$^{17}$ is C$_{1-4}$ alkyl,
3) C$_{3-7}$ cycloalkyl,
4) C(O)OR$^{18}$,
5) C(O)R$^{18}$,
6) C(O)NHR$^{18}$,
7) SO$_2$R$^{18}$,
8) C(O)NH$_2$, and
9) CN,
   wherein R$^{18}$ is selected from the group consisting of C$_{1-4}$alkyl, aryl, and C$_{3-7}$ cycloalkyl, and
R$^7$ and R$^8$ are independently selected from the group consisting of
a) hydrogen,
b) —CF$_3$, c) unsubstituted $C_{1-6}$ alkyl,
d) a ring slected from the group consisting of

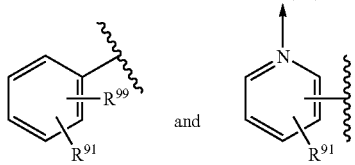
and wherein $R^{91}$ and $R^{99}$ are independently selected from the group consisting of
1) hydrogen,
2) halogen,
3) $C_{1-4}$ alkoxy,
4) $C_{1-4}$ alkyl,
5) hydroxy,
6) $CF_3$, and
7) cyano,
e) $C_{3-6}$ cycloalkyl,
f) $C_{1-6}$ alkyl substituted with one of the group consisting of
1) $C_{3-6}$ cycloalkyl,
2) —COOH,
3) —OH, 4)
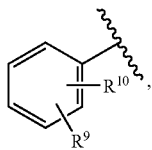, 5)
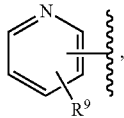, 6)
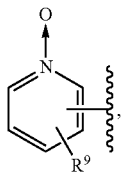

wherein $R^9$ and $R^{10}$ are independently selected from the group consisting of
aa) hydrogen,
bb) halogen,
cc) $C_{1-4}$ alkoxy,
dd) $C_{1-4}$ alkyl,
ee) hydroxy,
ff) $CF_3$ and
gg) cyano, and 3)
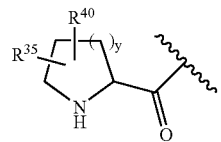

wherein
y is 0, 1 or 2, and
$R^{35}$ and $R^{40}$ are independently selected from the group consisting of hydrogen and $C_{1-6}$ alkyl;
$R^2$ is selected from the group consisting of
1) hydrogen,
2) halogen,
3) $C_{1-4}$ alkyl,
4) $C_{3-7}$ cycloalkyl,
5) $CF_3$,
6) $OCF_3$,
7) $C_{1-4}$ alkoxy, and
8) cyano; and
$R^{12}$ is
1) a 5-membered heteroaryl ring having 2, 3, or 4 heteroatoms, provided that at least 2 heteroatoms are N, and at most 1 of the heteroatoms is S or O, said ring being unsubstituted or substituted, at any one ring atom, with $C_{1-6}$ alkyl or halogen, or
2) a 6-membered heteroaryl ring with 1–2 nitrogen atoms, said ring being unsubstituted or substituted with with $C_{1-6}$ alkyl or halogen,
or a pharmaceutically acceptable salt thereof.

2. A compound of claim 1, or pharmaceutically acceptable salt thereof, wherein Q is selected from the group consisting of

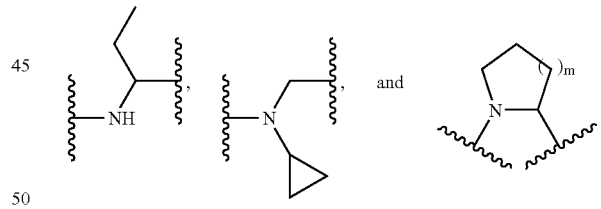

where the nitrogen atom is attached to $R^1$;
X is a bond;
$R^2$ is hydrogen, Cl or F;
y is 1 or 2.

3. A compound of claim 2, or pharmaceutically acceptable salt thereof, wherein
$R^{12}$ is independently selected from the group consisting of

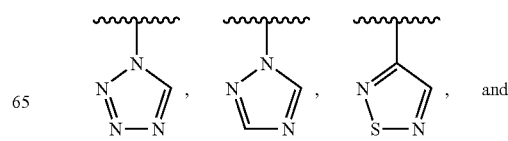

-continued
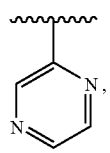
4. A compound of claim 3, or pharmaceutically acceptable salt thereof, wherein
R$^1$ is selected from the group consisting of
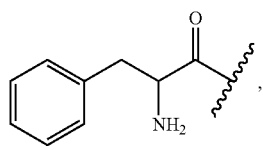
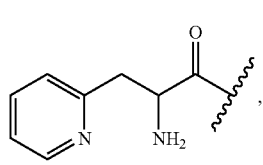
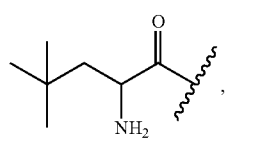
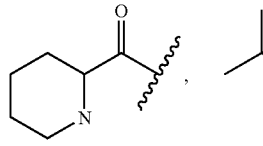
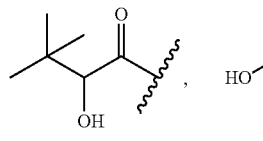
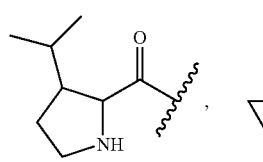
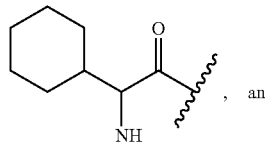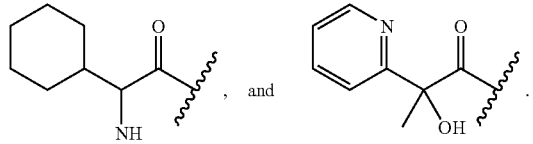
5. A compound of claim 4, or pharmaceutically acceptable salt thereof, selected from the group consisting of
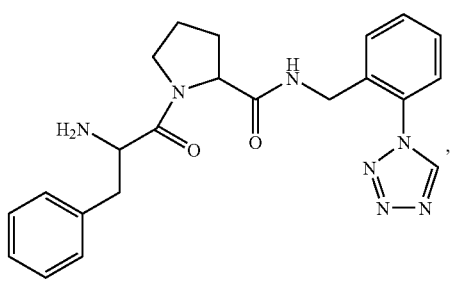
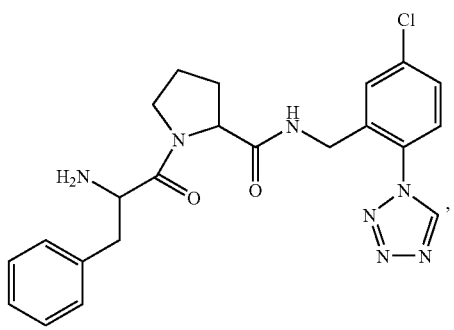
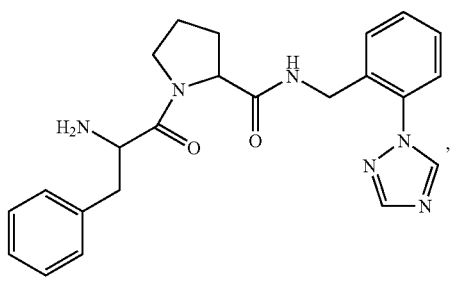
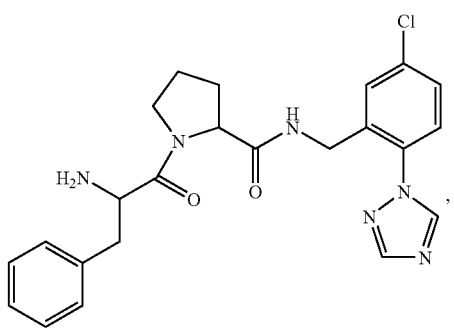
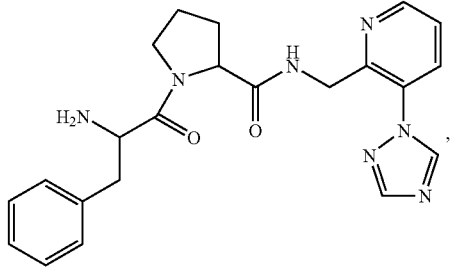

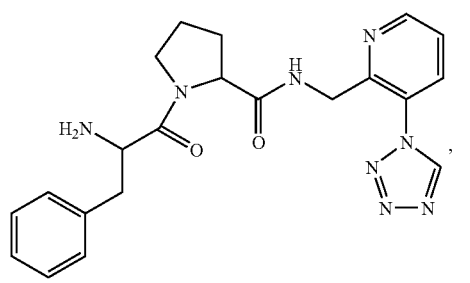,
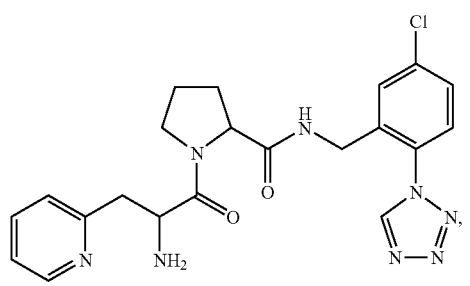,
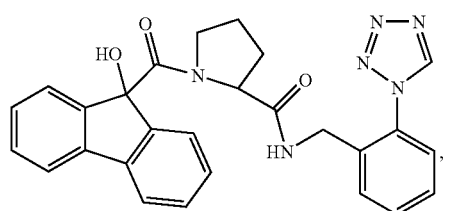,
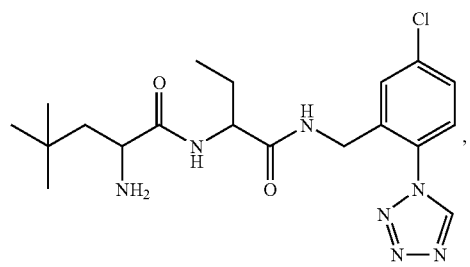,
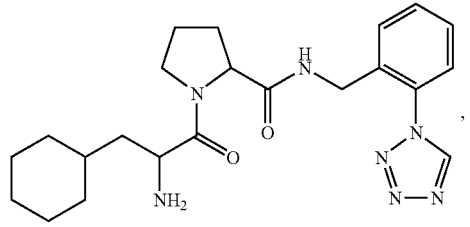,
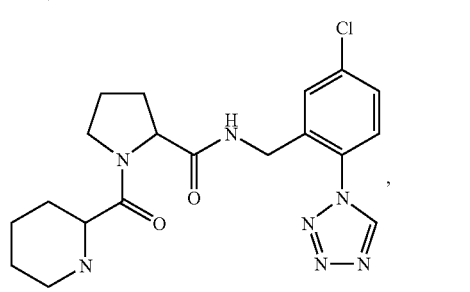,
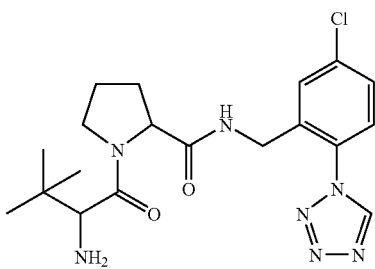,
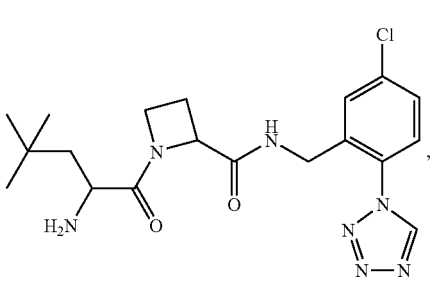,
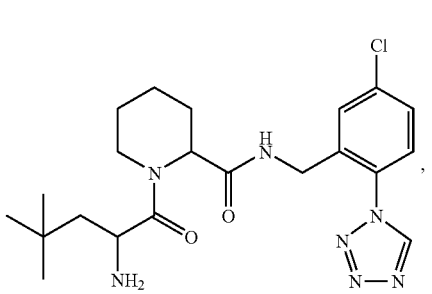,
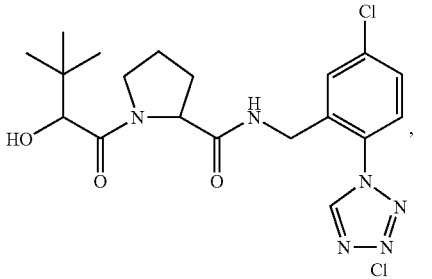,
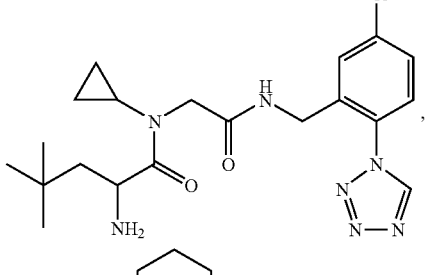,
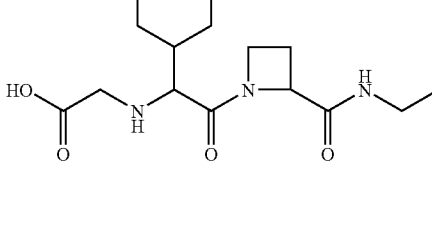, -continued

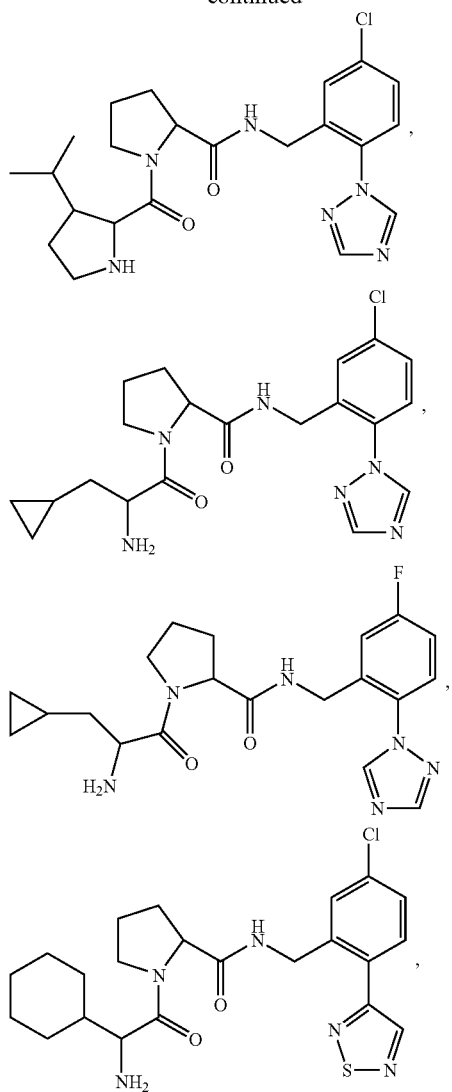

-continued

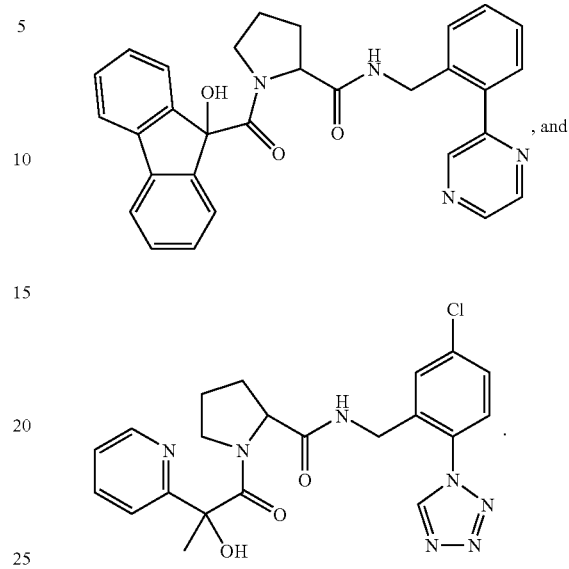

6. A composition for inhibiting thrombus formation in blood comprising a compound of claim 1 and a pharmaceutically acceptable carrier.

7. A method for inhibiting thrombus formation in a patient comprising administering to the patient a therapeutically effective amount of a compound of claim 5.

8. A method for inhibiting formation of blood platelet aggregates in a pateient comprising administering to the patient a therapeutically effective amount of a compound of claim 1.

9. A method for inhibiting thrombus formation in a pateient comprising administering to the patient a therapeutically effective amount of a compound of claim 1.

* * * * *